(12) United States Patent
Yasuda et al.

(10) Patent No.: US 7,160,877 B2
(45) Date of Patent: Jan. 9, 2007

(54) ALIPHATIC NITROGEN-CONTAINING 5-MEMBERED RING COMPOUND

(75) Inventors: Kosuke Yasuda, Saitama (JP); Hiroshi Morimoto, Saitama (JP); Saburo Kawanami, Saitama (JP); Masataka Hikota, Shiki (JP); Takeshi Matsumoto, Saitama (JP); Kenji Arakawa, Saitama (JP)

(73) Assignee: Tanabe Seiyaku Co., Ltd., Osaka (JP)

( * ) Notice: Subject to any disclaimer, the term of this patent is extended or adjusted under 35 U.S.C. 154(b) by 247 days.

(21) Appl. No.: 10/872,442

(22) Filed: Jun. 22, 2004

(65) Prior Publication Data

US 2004/0229926 A1    Nov. 18, 2004

Related U.S. Application Data

(62) Division of application No. 10/398,486, filed as application No. PCT/JP01/08803 on Oct. 5, 2001, now Pat. No. 6,849,622.

(30) Foreign Application Priority Data

| Oct. 6, 2000 | (JP) | ............................ 2000/308528 |
| Oct. 12, 2000 | (JP) | ............................ 2000/312562 |
| Mar. 30, 2001 | (JP) | ............................ 2001/099251 |

(51) Int. Cl.
*A61K 31/55* (2006.01)
*C07D 207/00* (2006.01)

(52) U.S. Cl. ................. 514/217.08; 514/269; 514/274; 514/365; 514/422; 514/300; 514/301; 514/342; 514/339; 548/538; 548/529; 548/525; 548/526; 544/349; 544/365; 544/121; 544/124; 546/114; 546/146

(58) Field of Classification Search ........... 514/217.08, 514/269, 274, 365, 422, 300, 301, 342, 339; 548/538, 529, 525, 526

See application file for complete search history.

(56) References Cited

U.S. PATENT DOCUMENTS

| 6,011,155 A | 1/2000 | Villhauer |
| 6,107,317 A | 8/2000 | Villhauer |
| 6,110,949 A | 8/2000 | Villhauer |
| 6,432,969 B1 | 8/2002 | Villhauer |

FOREIGN PATENT DOCUMENTS

| WO | WO 98/19998 | 5/1998 |
| WO | WO 00/34241 | 6/2000 |
| WO | WO 01/96295 A2 | 12/2001 |
| WO | WO 02/051836 A1 | 7/2002 |

OTHER PUBLICATIONS

Augustyns, K., et al., The Unique Properties of Dipeptidyl-peptidase IV (DPP IV / CD 26) and the Therapeutic Potential of DPP IV Inhibitors, *Current Medicinal Chemistry*, pp. 311-327 (1999).

*Primary Examiner*—Joseph K. McKane
*Assistant Examiner*—Robert Shiao
(74) *Attorney, Agent, or Firm*—Finnegan, Henderson Farabow, Garrett & Dunner, L.L.P.

(57) ABSTRACT

The present invention is to provide an aliphatic nitrogen-containing 5-membered ring compound represented by the formula [I]:

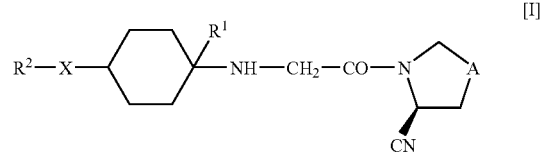

wherein A represents —$CH_2$— or —S—,
$R^1$ represents hydrogen atom, a lower alkyl group, a hydroxy lower alkyl group or a lower-alkoxy lower alkyl group,
X represents —$N(R^3)$—, —O— or —CO—, where $R^3$ represents hydrogen atom or a lower alkyl group, and
$R^2$ represents (1) a cyclic group which may be substituted, or (2) an amino group which may be substituted,
or a pharmaceutically acceptable salt thereof, a method for preparing the above-mentioned compound and a pharmaceutical composition comprising the above-mentioned compound as an effective ingredient.

14 Claims, No Drawings

ALIPHATIC NITROGEN-CONTAINING 5-MEMBERED RING COMPOUND

This application is a divisional of U.S. patent application Ser. No. 10/398,486, filed Apr. 4, 2003, now U.S. Pat. No. 6,849,622 which was filed under 35 U.S.C. 371 and is based on International Application PCT/JP01/08803, filed Oct. 5, 2001, both of which are herein incorporated by reference.

TECHNICAL FIELD

The present invention relates to a novel aliphatic nitrogen-containing 5-membered ring compound having superior dipeptidylpeptidase IV (DPPIV) inhibitory action that is useful as a pharmaceutical.

BACKGROUND ART

Dipeptidylpeptidase IV (DPPIV) is a kind of serine protease that specifically hydrolyzes a dipeptide of Xaa-Pro or Xaa-Ala (where Xaa may be any amino acid) from the N terminus of a polypeptide chain.

There are various reports regarding the role of DPPIV (also called to as CD26) in the body and its relationship with diseases (Holst, et al., Diabetes, Vol. 47, pp. 1663–1670, 1998; Augustyns, et al., Current Medicinal Chemistry, Vol. 6, pp. 311–327, 1999; Meester, et al., Immunol. Today, Vol. 20, pp. 367–375, 1999; and, Fleicher, et al., Immunol. Today, Vol. 15, pp. 180–184, 1994).

GLP-1 (glucagon-like peptide 1) is a peptide hormone that mainly acts in the pancreas after being secreted from the lower small intestine after meals, and primarily has the function of amplifying glucose-induced insulin secretion. In addition, there are several reports suggesting that GLP-1 has an appetite-suppressing action. DPPIV hydrolyzes GLP-1, forming an inactive or antagonistic peptide.

Substances that inhibit the enzyme activity of DPPIV enhance the insulin secretion response to oral glucose loading by enhancing the action of intrinsic GLP-1, thereby improving impaired glucose tolerance.

Consequently, DPPIV inhibitors are considered to be useful for the prophylaxis and treatment of diabetes (particularly type 2 diabetes), etc. Also, they are expected to be effective for the prophylaxis and treatment of other diseases induced or exacerbated by impaired glucose tolerance (including hyperglycemia (such as postprandial hyperglycemia), hyperinsulinemia, diabetes complications (such as renal disorder and neurological disorder), lipid metabolism disorder and obesity, etc.).

Moreover, DPPIV inhibitors are also expected to be effective for the prophylaxis and treatment of diseases that are to be improved by enhancing the appetite-suppressing action of GLP-1 (including overeating and obesity, etc.).

Also, DPPIV (CD26) present on the surface of T cells is strongly upregulated following T cell activation, and plays an important role in the activation and proliferation of T cells. T cell activity is known to be suppressed when DPPIV (CD26) is blocked by antibodies or inhibitory substances. Also, there has been an interest in the correlation between this enzyme and the pathological state in collagen metabolism disorders and diseases associated with abnormal immunity. For example, the DPPIV (CD26) positive rate of peripheral blood T cells is elevated in rheumatoid patients, and high levels of DPPIV activity have been detected in the urine of nephritis patients. Moreover, DPPIV (CD26) is also thought to play an important role in the entry of HIV into lymphocytes.

Consequently, substances that inhibit DPPIV (CD26) are expected to demonstrate prophylactic and therapeutic effects against diseases including autoimmune diseases (such as arthritis and rheumatoid arthritis), osteoporosis, acquired immunodeficiency syndrome (AIDS) and rejections of transplanted organs and tissues.

On the other hand, as compounds having DPPIV inhibitory action, there are described 2-cyanopyrrolidine derivatives having DPPIV inhibitory action in International Patent Laid-Open Publications Nos. WO98/19998 and The present invention provides a novel aliphatic nitrogen-containing 5-membered ring compound having an excellent DPPIV inhibitory action.

DISCLOSURE OF THE INVENTION

As a result of earnest research to solve the above problems, the present inventors found a novel aliphatic nitrogen-containing 5-membered ring compound having DPPIV inhibitory action, thereby accomplished the present invention.

Namely, the present invention relates to an aliphatic nitrogen-containing 5-membered ring compound represented by the formula [I]:

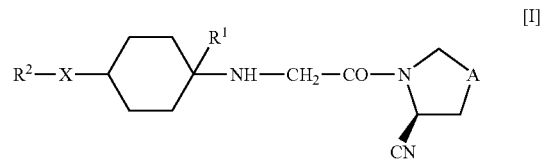

wherein A represents —$CH_2$— or —S—, $R^1$ represents hydrogen atom, a lower alkyl group, a hydroxy lower alkyl group or a lower alkoxy lower alkyl group, X represents —$N(R^3)$—, —O— or —CO—, where $R^3$ represents hydrogen atom or a lower alkyl group, and $R^2$ represents (1) a cyclic group which may be substituted, where the cyclic group portion is (i) a monocyclic, bicyclic or tricyclic hydrocarbon group, or (ii) a monocyclic, bicyclic or tricyclic heterocyclic group, or (2) an amino group which may be substituted, or a pharmaceutically acceptable salt thereof.

BEST MODE FOR CARRYING OUT THE INVENTION

Although optical isomers based on an asymmetric carbon can be present in the objective compound [I] of the present invention, the present invention includes any of these optical isomers as well as mixtures thereof. In addition, although isomers (cis form or trans form) are also present based on the relative positions of substituents with respect to the standard plane of a cyclic group, the present invention also includes any of these isomers as well as mixtures thereof.

In the present invention, examples of a lower alkyl group, a lower alkylthio group, a lower alkylsulfonyl group, a lower alkoxy group and a lower alkylamino group include linear or branched groups having 1 to 6 carbon atoms, and particularly those having 1 to 4 carbon atoms. And, examples of a lower alkanoyl group and a lower alkanoylamino group include linear or branched groups having 2 to 7 carbon atoms, and particularly those having 2 to 5 carbon atoms. Examples of a lower cycloalkyl group and lower cycloalkenyl group include those having 3 to 8 carbon atoms, and particularly 3 to 6 carbon atoms. Examples of a lower alkylene group include linear or branched groups having 1 to 6 carbon atoms, and particularly 1 to 4 carbon atoms. Examples of a lower alkenyl group and lower alkenylene group include those having 2 to 7 carbon atoms, and particularly 2 to 5 carbon atoms. Further, examples of a halogen atom include fluorine, chlorine, bromine and iodine.

In the objective compound [I] of the present invention, examples of hydrogen atom or a lower alkyl group represented by $R^3$ include hydrogen atom, methyl group, etc. Among them, hydrogen atom is more preferred.

In the compound [I] of the present invention, examples of "hydrogen atom, a lower alkyl group, a hydroxy lower alkyl group or lower alkoxy lower alkyl group" represented by $R^1$ include hydrogen atom, methyl group, hydroxymethyl group and methoxymethyl group. Among them, hydrogen atom is preferred.

In the compound [I] of the present invention, a cyclic group portion of "a cyclic group which may be substituted" represented by $R^2$ includes
(i) a monocyclic, bicyclic or tricyclic hydrocarbon group and
(ii) a monocyclic, bicyclic or tricyclic heterocyclic group.

Such monocyclic, bicyclic or tricyclic hydrocarbon groups include those having 3 to 15 carbon atoms, which may be partially or completely saturated.

Monocyclic hydrocarbon groups include those having 3 to 7 carbon atoms, examples of which include phenyl group, cyclohexyl group, cyclopentyl group, cyclobutyl group, cyclopropyl group, etc.

Bicyclic hydrocarbon groups include those having 9 to 11 carbon atoms, examples of which include an indanyl group, an indenyl group, a naphthyl group, a tetrahydronaphthyl group and partially or completely saturated cyclic groups thereof, etc.

Tricyclic hydrocarbon groups include those having 12 to 15 carbon atoms, examples of which include a fluorenyl group, an anthryl group, a phenanthryl group and partially or completely saturated cyclic groups thereof, etc.

Monocyclic, bicyclic or tricyclic heterocyclic groups include a monocyclic, bicyclic or tricyclic heterocyclic group containing 1 to 4 hetero atoms selected from nitrogen atom, oxygen atom and sulfur atom, which may be partially or completely saturated.

Monocyclic heterocyclic groups include a heterocyclic group containing 1 or 2 hetero atoms selected from nitrogen atom, oxygen atom and sulfur atom and comprising of a saturated or unsaturated 5- to 7-membered ring, examples of which include: pyrrolidinyl group, an imidazolidinyl group, a pyrazolidinyl group, an oxolanyl group, a thiolanyl group, a pyrrolinyl group, an imidazolinyl group, a pyrazolinyl group, a pyrrolyl group, an imidazolyl group, a pyrazolyl group, a triazolyl group, a tetrazolyl group, a furyl group, an oxazolyl group, an isoxazolyl group, an oxadiazolyl group, a thienyl group, a thiazolyl group, an isothiazolyl group, a thiadiazolyl group, a piperidyl group, a piperazinyl group, a morpholinyl group, a thiomorpholinyl group, a pyridyl group, a pyrimidinyl group, a pyrazinyl group, a pyridazinyl group, a pyranyl group, a tetrahydropyridyl group, a dihydropyridazinyl group, a perhydroazepinyl group, a perhydrothiazepinyl and partially or completely saturated cyclic groups thereof, etc.

Bicyclic heterocyclic groups include a heterocyclic group containing 1 to 3 hetero atoms selected from nitrogen atom, oxygen atom and sulfur atom and comprising two saturated or unsaturated 5- to 7-membered rings being fused, examples of which include:
an indolinyl group, an isoindolinyl group, an indolyl group, an indazolyl group, an isoindolyl group, a benzimidazolyl group, a benzothiazolyl group, a benzoxazolyl group, a benzodioxolanyl group, a benzothienyl group, a benzofuryl group, a thienopyridyl group, a thiazolopyridyl group, a pyrrolopyridyl group, a dihydropyrrolopyridyl group, a quinolyl group, an isoquinolyl group, a quinoxalinyl group, a quinazolinyl group, a phthalazinyl group, a cinnolinyl group, a chromanyl group, an isochromanyl group, a naphthyridinyl group and partially or completely saturated cyclic groups thereof, etc.

Tricyclic heterocyclic groups include a heterocyclic group containing 1 to 4 hetero atoms selected from nitrogen atom, oxygen atom and sulfur atom and comprising three saturated or unsaturated 5- to 7-membered rings being fused, examples of which include:
a benzoxolanopyrimidyl group, a β-carbolinyl group, a carbazolyl group, a phenothiazinyl group, a phenoxazinyl group and partially or completely saturated cyclic groups thereof, etc.

Among these cyclic groups (monocyclic, bicyclic or tricyclic hydrocarbon groups or monocyclic, bicyclic or tricyclic heterocyclic groups),
"(i) a monocyclic hydrocarbon group having 3 to 7 carbon atoms,
(ii) a bicyclic hydrocarbon groups having 9 to 11 carbon atoms,
(iii) a monocyclic heterocyclic group containing 1 or 2 hetero atoms selected from nitrogen atom, oxygen atom and sulfur atom, or
(iv) a bicyclic heterocyclic group containing 1 to 3 hetero atoms selected from nitrogen atom, oxygen atom and sulfur atom and comprising two 5- to 7-membered rings being fused" is preferred, examples of which include:
"phenyl group, cyclohexyl group, cyclopentyl group, cyclobutyl group, cyclopropyl group, an indanyl group, an indenyl group, a naphthyl group, tetrahydronaphthyl, a pyrrolidinyl group, an imidazolidinyl group, a pyrazolidinyl group, an oxolanyl group, a thiolanyl group, a pyrrolinyl group, an imidazolinyl group, a pyrazolinyl group, a pyrrolyl group, an imidazolyl group, a pyrazolyl group, a triazolyl group, a tetrazolyl group, a furyl group, an oxazolyl group, an isoxazolyl group, an oxadiazolyl group, a thienyl group, a thiazolyl group, an isothiazolyl group, a thiadiazolyl group, a piperidyl group, a piperazinyl group, a morpholinyl group, a thiomorpholinyl group, a pyridyl group, a pyrimidinyl group, a pyrazinyl group, a pyridazinyl group, a pyranyl group, a tetrahydropyridyl group, a dihydropyridazinyl group, a perhydroazepinyl group, a perhydrothiazepinyl group, an indolinyl group, an isoindolinyl group, an indolyl group, an indazolyl group, an isoindolyl group, a benzimidazolyl group, a benzothiazolyl group, a benzoxazolyl group, a benzodioxolanyl group, a benzothienyl group, a benzofuryl group, a thienopyridyl group, a thiazolopyridyl group, a pyrrolopyridyl group, a dihydropyrrolopyridyl group, a quinolyl group, an isoquinolyl group, a quinoxalinyl group, a quinazolinyl group, a phthalazinyl group, a cinnolinyl group, a chromanyl group, an isochromanyl group, a naphthyridinyl group and partially or completely saturated cyclic groups thereof, etc.".

Among them, more preferred examples include:
"phenyl group, cyclohexyl group, a pyrrolidinyl group, a tetrazolyl group, a furyl group, a thienyl group, a thiazolyl group, a piperidyl group, a piperazinyl group, a morpholinyl group, a thiomorpholinyl group, a pyridyl group, a pyrimidinyl group, a pyrazinyl group, a pyridazinyl group, a perhydroazepinyl group, an indolinyl group, an isoindolinyl group, a benzothienyl group, a thienopyridyl group, a pyrrolopyridyl group, a dihydropyrrolopyridyl group, a quinolyl group, an isoquinolyl group, a quinoxalinyl group and partially or completely saturated cyclic groups thereof, etc.", and further preferred examples include:

"a pyrrolidinyl group, a piperidyl group, a piperazinyl group, a morpholinyl group, a thiomorpholinyl group, a pyridyl group, a pyrimidinyl group, an indolinyl group, an isoindolinyl group, a pyrrolopyridyl group, a dihydropyrrolopyridyl group and partially or completely saturated cyclic groups thereof, etc."

Among them, particularly preferred examples include: "1-pyrrolidinyl group, 1-piperidyl group, 1-piperazinyl group, 4-morpholinyl group, 4-thiomorpholinyl group, 2-pyridyl group, 2-pyrimidinyl group, 2-isoindolinyl group, 1-indolinyl group, 2,3-dihydro-1H-pyrrolo[3,4-b]pyridin-2-yl group, etc.".

"A cyclic group (a monocyclic, bicyclic or tricyclic hydrocarbon group or a monocyclic, bicyclic or tricyclic heterocyclic group) which may be substituted" represented by $R^2$ may be unsubstituted or have 1 to 3 substituents which are the same or different.

Substituents in the cyclic group are not particularly limited, and examples of which include substituents selected from the following "substituents of Group A". Among them, "substituents of Group A'" are more preferred.

In the objective compound [I] of the present invention, "an amino group which may be substituted" represented by $R^2$ may be unsubstituted or may be an amino group having 1 or 2 substituents which are the same or different (a mono- or di-substituted amino group).

Substituents in the amino group are not particularly limited, and examples of which include substituents selected from the following "substituents of Group B". Among them, "substituents of Group B'" are more preferred.

"An amino group which may be substituted" represented by $R^2$ is preferably a substituted amino group (a mono- or di-substituted amino group), and more specifically "an amino group substituted by 1 or 2 substituents which are the same or different and selected from the group consisting of a lower alkyl group (methyl group, ethyl group, isopropyl group, butyl group, etc.), a lower cycloalkyl group, a lower alkoxy-substituted lower alkyl group, a pyrimidinyl group, a thiazolyl group and a thiadiazolyl group" is preferred. Among them, "(i) an amino group di-substituted by substituents which are the same or different and selected from a lower alkyl group (methyl group, ethyl group, isopropyl group, butyl group, etc.), a lower cycloalkyl group and a lower alkoxy-substituted lower alkyl group; or (ii) an amino group mono-substituted by a substituent selected from a pyrimidinyl group, a thiazolyl group and a thiadiazolyl group" is more preferred, and "an amino group di-substituted by substituents which are the same or different and selected from a lower alkyl group (methyl group, ethyl group, isopropyl group, butyl group, etc.), a lower cycloalkyl group and a lower alkoxy-substituted lower alkyl group" is particularly preferred.

Substituents of Group A

As substituents of Group A, the following substituents are mentioned:

a halogen atom (Cl, F, Br, etc.); cyano group; nitro group, oxo group, hydroxy group, carboxy group; oxidyl group; amino group; carbamoyl group; aminosulfonyl group; a lower alkyl group; a lower alkoxy group; a lower alkanoyl group; a lower alkoxycarbonyl group; a lower alkoxy-substituted lower alkanoyl group; a lower alkoxycarbonyl-substituted lower alkoxy group; a lower alkoxycarbonyl-substituted lower alkoxycarbonyl group;

a lower alkylthio group;

a lower alkylsulfonyl group;

a di-lower alkylamino-substituted lower alkoxy group;

a di-lower alkylaminocarboxy group;

a lower alkyl group substituted by group(s) selected from amino group, carbamoyl group, a halogen atom, hydroxy group, carboxy group, a lower alkoxy group and a mono- or di-substituted amino group (substituents in the substituted amino group portion are not particularly limited, and examples of which include substituents of Group C mentioned below.);

a mono- or di-substituted amino group or a mono- or di-substituted carbamoyl group (substituents in the substituted amino group or substituted carbamoyl group are not particularly limited, and examples of which include substituents of Group C mentioned below.);

a substituted or unsubstituted lower cycloalkyl group, a substituted or unsubstituted lower cycloalkyl-CO—, a substituted or unsubstituted lower cycloalkyl-lower alkyl group, a substituted or unsubstituted phenyl group, a substituted or unsubstituted phenyl-O—, a substituted or unsubstituted phenyl-CO—, a substituted or unsubstituted phenyl-lower alkyl group, a substituted or unsubstituted phenyl-O-lower alkyl group, a substituted or unsubstituted phenylsulfonyl group, a substituted or unsubstituted phenyl-lower alkoxy group, a substituted or unsubstituted phenyl-lower alkoxycarbonyl group, a substituted or unsubstituted cycloalkenyl group (a cyclobutenyl group, etc.), a substituted or unsubstituted bicyclic heterocyclic group, a substituted or unsubstituted monocyclic 5- or 6-membered heterocyclic group, a substituted or unsubstituted monocyclic 5- or 6-membered heterocyclic group-O—, a substituted or unsubstituted monocyclic 5- or 6-membered heterocyclic group-CO—, a substituted or unsubstituted monocyclic 5- or 6-membered heterocyclic group-CO-lower alkyl group, and a substituted or unsubstituted monocyclic 5- or 6-membered heterocyclic group-lower alkyl group (substituents in the substituted lower cycloalkyl group portion, substituted phenyl group portion, substituted lower cycloalkenyl group portion, substituted bicyclic heterocyclic group portion or substituted monocyclic 5- or 6-membered heterocyclic group portion are not particularly limited, and examples of which include a halogen atom (Cl, F, Br, etc.), cyano group, nitro group, oxo group and substituents in the substituents of Group C mentioned below, etc.

Also, a monocyclic 5- or 6-membered heterocyclic group portion includes a monocyclic 5- or 6-membered heterocyclic group containing 1 or 2 hetero atoms selected from nitrogen atom, oxygen atom and sulfur atom, and specific examples include a piperidyl group, a piperazinyl group, a morpholinyl group, a pyridyl group, a pyrimidinyl group, a pyrazinyl group, a pyridazinyl group, a pyrrolidinyl group, an imidazolidinyl group, a pyrazolidinyl group, a pyrrolyl group, an imidazolyl group, a pyrazolyl group, a thiazolyl group, a thiadiazolyl group, a thienyl group, etc.

Also, a bicyclic heterocyclic group portion includes a bicyclic heterocyclic group containing 1 to 3 hetero atoms selected from nitrogen atom, oxygen atom and sulfur atom and comprising two 5- or 6-membered rings being fused, and examples of which include an isoindolinyl group, an indolinyl group, etc.)

Substituents Group A' (Particularly Preferred Substituents of Group A)

As more preferable substituents of Group A, the following substituents are mentioned:
a halogen atom (Cl, etc.); cyano group; nitro group; oxo group; carbamoyl group; a lower alkyl group; a lower alkoxy group; a lower alkanoyl group; a lower alkoxycarbonyl group; a lower alkoxy-substituted lower alkyl group,
a mono- or di-substituted amino group (a lower cycloalkylcarbonyl-substituted amino group, etc.),
a mono- or di-substituted carbamoyl group (a phenyl-substituted carbamoyl group, etc.),
a lower cycloalkyl-CO—,
a substituted or unsubstituted phenyl group (phenyl group, a halophenyl group, etc.),
a substituted or unsubstituted phenyl-lower alkyl group (a phenyl-lower alkyl group, a halophenyl-lower alkyl group, etc.),
a substituted or unsubstituted monocyclic 5- or 6-membered heterocyclic group (a thienyl group, etc.),
a substituted or unsubstituted monocyclic 5- or 6-membered heterocyclic group-O— (a pyrimidinyloxy group, a halopyrimidinyloxy group, etc.), and
a substituted or unsubstituted monocyclic 5- or 6-membered heterocyclic group-CO— (a pyridylcarbonyl group, a thienyl-carbonyl group, etc.).

(In the above description, each monocyclic 5- or 6-membered heterocyclic group portion includes a monocyclic 5- or 6-membered heterocyclic group containing 1 or 2 hetero atoms selected from nitrogen atom, oxygen atom and sulfur atom, and examples of which include a pyridyl group, a pyrimidinyl group, a thienyl group, etc.)

Substituents of Group B

As substituents of Group B, the following substituents are mentioned:
a lower alkyl group; a lower alkoxy-substituted lower alkyl group; a lower alkoxycarbonyl-substituted lower alkyl group; a hydroxy lower alkyl group; a carboxy lower alkyl group;
a substituted or unsubstituted lower cycloalkyl group,
a substituted or unsubstituted lower cycloalkyl-lower alkyl group,
a substituted or unsubstituted phenyl group,
a substituted or unsubstituted phenyl-lower alkyl group,
a substituted or unsubstituted bicyclic hydrocarbon group,
a substituted or unsubstituted monocyclic 5- or 6-membered heterocyclic group,
a substituted or unsubstituted monocyclic 5- or 6-membered heterocyclic group-lower alkyl group, and
a substituted or unsubstituted bicyclic heterocyclic group-lower alkyl group
(substituents in the substituted lower cycloalkyl group portion, substituted phenyl group portion, substituted bicyclic hydrocarbon group portion, substituted monocyclic 5- or 6-membered heterocyclic group portion or substituted bicyclic heterocyclic group portion are not particularly limited, and examples of which include substituents in the substituents of Group C mentioned below.

A bicyclic hydrocarbon group portion includes a bicyclic hydrocarbon group having 9 to 11 carbon atoms, and examples of which include an indanyl group, etc.

Also, a monocyclic 5- or 6-membered heterocyclic group portion includes a monocyclic 5- or 6-membered heterocyclic group containing 1 or 2 hetero atoms selected from nitrogen atom, oxygen atom and sulfur atom, and examples of which include a piperidyl group, a piperazinyl group, a morpholinyl group, a pyridyl group, a pyrimidinyl group, a pyrazinyl group, a pyridazinyl group, a pyrrolidinyl group, an imidazolidinyl group, a pyrazolidinyl group, a pyrrolyl group, an imidazolyl group, a pyrazolyl group, a thiazolyl group, a thiadiazolyl group, a thienyl group, etc.

Also, a bicyclic heterocyclic group portion includes a bicyclic heterocyclic group containing 1 to 3 hetero atoms selected from nitrogen atom, oxygen atom and sulfur atom and comprising two 5- or 6-membered rings being fused, and examples of which include a benzodioxolanyl group, etc.).

Substituents of Group B' (More Preferred Substituents of Group B)

As more preferred substituents of Group B, the following substituents are mentioned:
a lower alkyl group (methyl group, ethyl group, isopropyl group, butyl group, etc.), a lower cycloalkyl group, a lower alkoxy-substituted lower alkyl group, a pyrimidinyl group, a thiazolyl group, a thiadiazolyl group.

As particularly preferred substituents of Group B, the following substituents are exemplified:
In case that $R^2$ is a di-substituted amino group,
a lower alkyl group (methyl group, ethyl group, isopropyl group, butyl group, etc.), a lower cycloalkyl group and a lower alkoxy-substituted lower alkyl group; and
in case that $R^2$ is a mono-substituted amino group, a pyrimidinyl group, a thiazolyl group and a thiadiazolyl group.

Substituents of Group C

As substituents of Group C, the following substituents are mentioned:
a lower alkyl group; a hydroxy-lower alkyl group; a lower alkanoyl group; a lower cycloalkylcarbonyl group; a lower alkoxy group; a lower alkoxycarbonyl group; a lower alkylsulfonyl group; a di-lower alkyl-substituted carbamoyl group; a di-lower alkylamino-substituted lower alkanoyl group; and
a substituted or unsubstituted phenyl group,
a substituted or unsubstituted phenyl-O—,
a substituted or unsubstituted phenyl-CO—,
a substituted or unsubstituted phenyl-lower alkanoyl group,
a substituted or unsubstituted phenyl-lower alkyl group, a substituted or unsubstituted phenyl-lower alkoxy group,
a substituted or unsubstituted monocyclic 5- or 6-membered heterocyclic group,
a substituted or unsubstituted monocyclic 5- or 6-membered heterocyclic group-O— (a pyridyloxy group, etc.),
a substituted or unsubstituted monocyclic 5- or 6-membered heterocyclic group-CO— (a pyridylcarbonyl group, etc.), and
a substituted or unsubstituted monocyclic 5- or 6-membered heterocyclic group-substituted amino group (a pyridylamino group, etc.)
(substituents in the substituted phenyl group portion or substituted monocyclic 5- or 6-membered heterocyclic group portion are not particularly limited, and examples of which include
a halogen atom (Cl, F, Br, etc.), cyano group, nitro group, oxo group, a lower alkyl group, a lower alkoxy group, a lower alkanoyl group, and a lower alkoxycarbonyl group, etc.

Also, a monocyclic 5- or 6-membered heterocyclic group portion includes a monocyclic 5- or 6-membered heterocyclic group containing 1 or 2 hetero atoms selected from nitrogen atom, oxygen atom and sulfur atom, and examples of which include
a piperidyl group, a piperazinyl group, a morpholinyl group, a pyridyl group, a pyrimidinyl group, a pyrazinyl group, a pyridazinyl group, a pyrrolidinyl group, an imidazolidinyl group, a pyrazolidinyl group, a pyrrolyl group, an imidazolyl group, a pyrazolyl group, a thiazolyl group, a thiadiazolyl group, a thienyl group, etc.)

In the objective compound [I] of the present invention, as $R^2$ when X is —N($R^3$)— or —O—, a cyclic group which may be substituted may be mentioned as a preferred example.

Also, in the objective compound [I] of the present invention, as $R^2$ when X is —CO—, there may be mentioned (1) a monocyclic, bicyclic or tricyclic nitrogen-containing heterocyclic group which may be substituted or (2) an amino group which may be substituted, represented by the formula:

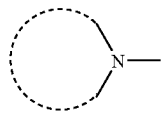

as preferred examples.

Also, in the objective compound [I] of the present invention, among the two kinds of cis-trans isomers based on a cyclohexyl ring in the structure [I] as a standard plane, a trans-isomeric compound is more preferred from the viewpoint of obtaining higher DPPIV inhibitory activity. That is, among the objective compound [I] of the present invention, a compound having the following partial structure:

or a pharmaceutically acceptable salt thereof is preferred.
In particular, for a compound in which the group X is —CO—, superiority of such trans isomer is remarkable.

As one compound group of the compounds of the present invention, among the compounds [I], those in which $R^2$ is
(1) a cyclic group which may have 1 to 3 substituents which are the same or different and selected from the substituents of Group A, where the cyclic group portion is (i) a monocyclic, bicyclic or tricyclic hydrocarbon group, or
(ii) a monocyclic, bicyclic or tricyclic heterocyclic group, or
(2) an amino group having 1 or 2 substituents which are the same or different and selected from the substituents of Group B can be mentioned. (Compound Group 1)

Also, as other compound groups, among the compounds [I] or the above-mentioned Compound Group 1, the compounds in which $R^2$ is
(1) a cyclic group which may be substituted, where the cyclic group portion is selected from the following (i) to (iv):
"(i) a monocyclic hydrocarbon group having 3 to 7 carbon atoms,
(ii) a bicyclic hydrocarbon groups having 9 to 11 carbon atoms,
(iii) a monocyclic heterocyclic group containing 1 or 2 hetero atoms selected from nitrogen atom, oxygen atom and sulfur atom, and
(iv) a bicyclic heterocyclic group containing 1 to 3 hetero atoms selected from nitrogen atom, oxygen atom and sulfur atom and comprising two 5- to 7-membered rings being fused; or
(2) a substituted amino group;
can be mentioned (Compound Group 2).

Also, among the above-mentioned Compound Group 2, the compounds in which $R^2$ is
(1) a cyclic group which may be substituted wherein the cyclic group portion is a group selected from phenyl group, cyclohexyl group, cyclopentyl group, cyclobutyl group, cyclopropyl group, an indanyl group, an indenyl group, a naphthyl group, tetrahydronaphthyl, a pyrrolidinyl group, an imidazolidinyl group, a pyrazolidinyl group, an oxolanyl group, a thiolanyl group, a pyrrolinyl group, an imidazolinyl group, a pyrazolinyl group, a pyrrolyl group, an imidazolyl group, a pyrazolyl group, a triazolyl group, a tetrazolyl group, a furyl group, an oxazolyl group, an isoxazolyl group, an oxadiazolyl group, a thienyl group, a thiazolyl group, an isothiazolyl group, a thiadiazolyl group, a piperidyl group, a piperazinyl group, a morpholinyl group, a thiomorpholinyl group, a pyridyl group, a pyrimidinyl group, a pyrazinyl group, a pyridazinyl group, a pyranyl group, a tetrahydropyridyl group, a dihydropyridazinyl group, a perhydroazepinyl group, a perhydrothiazepinyl group, an indolinyl group, an isoindolinyl group, an indolyl group, an indazolyl group, an isoindolyl group, a benzimidazolyl group, a benzothiazolyl group, a benzoxazolyl group, a benzodioxolanyl group, a benzothienyl group, a benzofuryl group, a thienopyridyl group, a thiazolopyridyl group, a pyrrolopyridyl group, a dihydropyrrolopyridyl group, a quinolyl group, an isoquinolyl group, a quinoxalinyl group, a quinazolinyl group, a phthalazinyl group, a cinnolinyl group, a chromanyl group, an isochromanyl group, a naphthyridinyl group and partially or completely saturated cyclic groups thereof; or
(2) a substituted amino group can be mentioned (Compound Group 3).

Also, in Compound Group 3, as more preferred compound group, the compounds in which $R^2$ is
(1) a cyclic group which may be substituted, where the cyclic group portion is a group selected from the group consisting of phenyl group, cyclohexyl group, a pyrrolidinyl group, a tetrazolyl group, a furyl group, a thienyl group, a thiazolyl group, a piperidyl group, a piperazinyl group, a morpholinyl group, a thiomorpholinyl group, a pyridyl group, a pyrimidinyl group, a pyrazinyl group, a pyridazinyl group, a perhydroazepinyl group, an indolinyl group, an isoindolinyl group, a benzothienyl group, a thienopyridyl group, a pyrrolopyridyl group, a dihydropyrrolopyridyl group, a quinolyl group, an isoquinolyl group, a quinoxalinyl group and partially or completely saturated cyclic-groups thereof; or (2) a substituted amino group can be mentioned (Compound Group 4).

Also, in Compound Group 4, as more preferred compound group, the compounds in which $R^2$ is (1) a cyclic group which may be substituted wherein the cyclic group portion is a group selected from a pyrrolidinyl group, a piperidyl group, a piperazinyl group, a morpholinyl group, a thiomorpholinyl group, a pyridyl group, a pyrimidinyl group, an indolinyl group, an isoindolinyl group, a pyrrolopyridyl group, a dihydropyrrolopyridyl group and partially or completely saturated cyclic groups thereof; or (2) a substituted amino group can be mentioned (Compound Group 5).

Also, among the compounds [I], as another more preferred compound group, the compounds in which $R^2$ is (1) a cyclic group which may have 1 to 3 substituents, which are the same or different, selected from the substituents of Group A', where the cyclic group portion is selected from the group consisting of a pyrrolidinyl group, a piperidyl group, a piperazinyl group, a morpholinyl group, a thiomorpholinyl group, a pyridyl group, a pyrimidinyl group, an indolinyl group, an isoindolinyl group, a pyrrolopyridyl group, a dihydropyrrolopyridyl group and partially or completely saturated cyclic groups thereof; or (2) an amino group substituted by 1 or 2 substituents, which are the same or different, selected from the substituents of Group B' can be mentioned. (Compound Group 6)

Also, among the compounds [I], or among each of the above-mentioned Compound Groups 1, 2, 3, 4, 5 and 6, a compound group in which, when X is —N($R^3$)— or —O—, $R^2$ is a cyclic group which may be substituted can be mentioned.

(Compound Group 7)

Also, among the compounds [I], or among each of the above-mentioned Compound Groups 1, 2, 3, 4, 5 and 6, a group of compounds in which, when X is —CO—, $R^2$ is (1) a monocyclic, bicyclic or tricyclic nitrogen-containing heterocyclic group which may be substituted or (2) an amino group which may be substituted, represented by the formula:

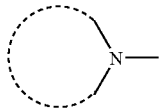

can be mentioned. (Compound Group 8)

Also, among the compounds [I] or the above-mentioned Compound Groups 1, 2, 3, 4, 5, 6, 7 or 8, as more preferred compound groups, a compound group in which X is —CO— or —O— and A is —CH$_2$—;

a compound group in which X is —CO— or —O—, A is —CH$_2$— and $R^1$ is hydrogen atom;

a compound group in which X is —CO—, A is —CH$_2$— and $R^1$ is hydrogen atom;

a compound group in which X is —CO—, A is —CH$_2$—, $R^1$ is hydrogen atom and $R^2$ is a cyclic group which may be substituted;

a compound group in which X is —CO—, A is —CH$_2$—, $R^1$ is hydrogen atom and $R^2$ is a substituted amino group;

a compound group in which X is —CO— or —O— and A is —S—;

a group of compounds in which X is —CO— or —O—, A is —S— and $R^1$ is hydrogen atom;

a compound group in which X is —CO—, A is —S— and $R^1$ is hydrogen atom;

a compound group in which X is —CO—, A is —S—, $R^1$ is hydrogen atom and $R^2$ is a cyclic group which may be substituted;

a compound group in which X is —CO—, A is —S—, $R^1$ is hydrogen atom and $R^2$ is a substituted amino group, etc. may be mentioned.

Also, in each of the above-mentioned compound groups, as a more preferred compound group, a compound group having the following partial structure:

can be mentioned.

Also, among the compounds [I], the following compounds can be mentioned as examples of preferred compounds;

(S)-2-cyano-1-[trans-4-(5-nitro-2-pyridylamino)-cyclohexylamino]acetylpyrrolidine;

(S)-2-cyano-1-[trans-4-(5-cyano-2-pyridyloxy)-cyclohexylamino]acetylpyrrolidine;

(S)-2-cyano-1-[trans-4-(dimethylaminocarbonyl)-cyclohexylamino]acetylpyrrolidine;

(S)-2-cyano-1-[trans-4-(morpholinocarbonyl)cyclohexylamino]acetylpyrrolidine;

(S)-2-cyano-1-[trans-4-(5-bromo-2-pyrimidinyloxy)-cyclohexylamino]acetylpyrrolidine;

(S)-2-cyano-1-[trans-4-(5-pyrimidinylaminocarbonyl)-cyclohexylamino]acetylpyrrolidine;

(S)-2-cyano-1-[trans-4-(N-ethyl-N-methoxyethylaminocarbonyl)cyclohexylamino]acetylpyrrolidine;

(S)-2-cyano-1-[trans-4-(N-ethyl-N-isopropylaminocarbonyl)cyclohexylamino]acetylpyrrolidine;

(S)-2-cyano-1-[trans-4-(N-methyl-N-butylaminocarbonyl)cyclohexylamino]acetylpyrrolidine;

(S)-2-cyano-1-[trans-4-[(S)-2-methoxymethylpyrrolidin-1-ylcarbonyl]cyclohexylamino]acetylpyrrolidine;

(S)-2-cyano-1-[trans-4-(3-carbamoylpiperidinocarbonyl) cyclohexylamino]acetylpyrrolidine;

(S)-2-cyano-1-[trans-4-(3-nitro-2-pyridylamino)cyclohexylamino]acetylpyrrolidine;

(S)-2-cyano-1-[trans-4-(4-acetylpiperazin-1-ylcarbonyl) cyclohexylamino]acetylpyrrolidine;

(S)-2-cyano-1-[trans-4-(2-isoindolinylcarbonyl)cyclohexylamino]acetylpyrrolidine;

(S)-2-cyano-1-[trans-4-[4-(3-pyridylcarbonyl)piperazin-1-ylcarbonyl]cyclohexylamino]acetylpyrrolidine;

(S)-2-cyano-1-[trans-4-[4-(3-thenoyl)piperazin-1-ylcarbonyl]cyclohexylamino)acetylpyrrolidine;

(S)-2-cyano-1-{trans-4-[4-(4-chlorophenyl)piperazin-1-ylcarbonyl]cyclohexylamino]acetylpyrrolidine;

(S)-2-cyano-1-[trans-4-(cis-2,6-dimethylmorpholinocarbonyl)cyclohexylamino]acetylpyrrolidine;

(S)-2-cyano-1-[trans-4-(5-nitro-2-isoindolinylcarbonyl)cyclohexylamino]acetylpyrrolidine;

(S)-2-cyano-1-[trans-4-(piperidinocarbonyl)cyclohexylamino]acetylpyrrolidine;

(S)-2-cyano-1-(trans-4-(4-carbamoylpiperidinocarbonyl)cyclohexylamino)acetylpyrrolidine;

(S)-2-cyano-1-[trans-4-(1-pyrrolidinylcarbonyl)cyclohexylamino]acetylpyrrolidine;

(S)-2-cyano-1-[trans-4-(4-cyclopropylcarbonylpiperazin-1-ylcarbonyl)cyclohexylamino]acetylpyrrolidine;

(S)-2-cyano-1-[trans-4-(4-propionylpiperazin-1-ylcarbonyl)cyclohexylamino]acetylpyrrolidine;

(S)-2-cyano-1-[trans-4-(1-indolinylcarbonyl)cyclohexylamino]acetylpyrrolidine;

(S)-2-cyano-1-[trans-4-(2,3-dihydro-1H-pyrrolo[3,4-b]pyridin-2-ylcarbonyl)cyclohexylamino]acetylpyrrolidine;

(S)-2-cyano-1-[trans-4-[4-(2-pyrimidinyloxy)-piperidinocarbonyl]cyclohexylamino]acetylpyrrolidine;

(S)-2-cyano-1-(trans-4-[4-(5-bromo-2-pyrimidinyloxy)-piperidinocarbonyl]cyclohexylamino}acetylpyrrolidine;

(S)-2-cyano-1-[trans-4-(cis-3,5-dimethyl-4-benzylpiperazin-1-ylcarbonyl)cyclohexylamino]acetylpyrrolidine;

(S)-2-cyano-1-[trans-4-(4-cyclohexylcarbonylaminopiperidinocarbonyl)cyclohexylamino]acetylpyrrolidine; —(S)-2-cyano-1-{trans-4-[4-(N-phenylcarbamoyl)-piperazin-1-ylcarbonyl]cyclohexylamino}acetylpyrrolidine;

(S)-2-cyano-1-[trans-4-(4-ethoxycarbonylpiperazin-1-ylcarbonyl)cyclohexylamino]acetylpyrrolidine;

(S)-2-cyano-1-{trans-4-[4-(2-thienyl)piperidinocarbonyl]cyclohexylamino}acetylpyrrolidine;

(S)-2-cyano-1-[trans-4-(1,1-dioxoperhydro-1,4-thiazin-4-ylcarbonyl)cyclohexylamino]acetylpyrrolidine;

(R)-4-cyano-3-[trans-4-(5-nitro-2-pyridylamino)cyclohexylamino]acetylthiazolidine;

(R)-4-cyano-3-[trans-4-(5-cyano-2-pyridyloxy)cyclohexylamino]acetylthiazolidine;

(R)-4-cyano-3-[trans-4-(dimethylaminocarbonyl)cyclohexylamino]acetylthiazolidine;

(R)-4-cyano-3-[trans-4-(2-isoindolinylcarbonyl)cyclohexylamino]acetylthiazolidine;

(R)-4-cyano-3-[trans-4-(morpholinocarbonyl)cyclohexylamino]acetylthiazolidine; and (R)-4-cyano-3-[trans-4-(pyrrolidinylcarbonyl)cyclohexylamino]acetylthiazolidine.

The objective compound [I] or a pharmaceutically acceptable salt thereof of the present invention has superior inhibitory action on the enzyme activity of DPPIV. They have superior inhibitory action especially on human DPPIV. In addition, they also exhibit high selectivity with respect to DPPIV (namely, type IV dipeptidylpeptidase) in various serine proteases (e.g., plasmin, thrombin, prolylendopeptidase, trypsin and dipeptidylpeptidase II).

Also, the objective compound [I] or a pharmaceutically acceptable salt thereof of the present invention improves insulin secretion response to oral glucose loading by means of its DPPIV inhibitory action.

Thus, the objective compound [I] or a pharmaceutically acceptable salt thereof of the present invention is useful as prophylactic or therapeutic agents for diseases relating to DPPIV (diseases mediated by DPPIV), that is, diseases which is expected to be alleviated by inhibiting DPPIV enzyme activity. Examples of such diseases include diabetes (e.g., type 1 diabetes and type 2 diabetes), hyperglycemia (such as postprandial hyperglycemia), hyperinsulinemia, diabetes complications (such as renal disorder and neurological disorder), obesity, overeating, lipid metabolism disorder (such as hyperlipemia including hypertriglyceridemia and others), autoimmune diseases (such as arthritis and rheumatoid arthritis), osteoporosis, acquired immunodeficiency syndrome (AIDS) and rejection of transplanted organs and tissues.

The objective compound [I] or a pharmaceutically acceptable salt thereof of the present invention is particularly useful as a prophylactic or therapeutic agent of diabetes (and particularly type 2 diabetes).

Also, the compound of the present invention has low toxicity, and thus, has a high degree of safety when used as a pharmaceutical compound. Also, it also demonstrates superior pharmacokinetic characteristics [including bioavailability, in vitro metabolic stability (stability in human liver homogenates), P450 inhibitory action, protein binding capabilities, etc.].

The DPPIV inhibitory action of the compound of the present invention as well as its pharmaceutical efficacy (including anti-hyperglycemia effect and the effect of improving insulin secretion response to glucose loading) based on that action can be confirmed by known methods or methods equivalent to those methods (WO98/19998; WO00/34241; Holst, et al., Diabetes, Vol. 47, pp. 1663–1670, 1998; Augustyns, et al., Current Medicinal Chemistry, Vol. 6, pp. 311–327, 1999; Meester, et al., Immunol. Today, Vol. 20, pp. 367–375, 1999; and, Fleicher, et al., Immunol. Today, Vol. 15, pp. 180–184, 1994).

The objective compound [I] of the present invention can be used for a pharmaceutical use either in a free form or in a form of a pharmaceutically acceptable salt. Examples of the pharmaceutically acceptable salt of the compound [I] include an inorganic acid salt such as hydrochloride, sulfate, phosphate or hydrobromide, and an organic acid salt such as acetate, fumarate, oxalate, citrate, methanesulfonate, benzenesulfonate, tosylate or maleate, etc. In addition, in case that a compound has a substituent(s) such as carboxyl group, a salt with a base (for example, an alkali metal salt such as a sodium salt, a potassium salt, etc., or an alkaline earth metal salt such as a calcium salt and the like) may be mentioned.

The objective compound [I] or a pharmaceutically acceptable salt thereof of the present invention includes its internal salt, an adduct, a solvate and a hydrate.

The objective compound [I] or a pharmaceutically acceptable salt thereof of the present invention can be administered orally or parenterally and used as commonly used pharmaceutical preparations such as a tablet, granule, capsule, powder, injection solution and inhalant. For example, the compound of the present invention can be used with an excipient or a diluent acceptable for general pharmaceuticals such as a binder, disintegrator, extender, filler and lubricant, to form a preparation according to the usual method.

The administration dose of the objective compound [I] or a pharmaceutically acceptable salt thereof of the present invention may vary depending on the administration method, age, weight and condition of a patient, and it is generally about 0.01 to 300 mg/kg, particularly preferably about 0.1 to 30 mg/kg per day.

The objective compound [I] of the present invention can be prepared according to the following (Process A) and (Process B), but it is not limited to these processes.

(Process A)

The objective compound [I] of the present invention can be prepared by reacting a compound represented by the formula [II]:

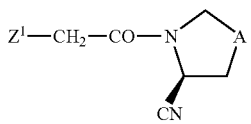

[II]

wherein $Z^1$ represents a reactive residue and A has the same meaning as defined above, with a compound represented by the formula [III]:

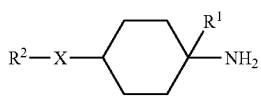

[III]

wherein $R^1$, $R^2$ and X have the same meanings as defined above, or a salt thereof, and optionally, by making the product into a pharmaceutically acceptable salt.

As examples of the salt of the compound [III], a salt with an inorganic acid such as hydrochloride and sulfate, or a salt with an inorganic base such as an alkali metal salt and an alkaline earth metal salt can be used.

As the reactive residue of $Z^1$, commonly used reactive residues such as a halogen atom, a lower alkylsulfonyloxy group and an arylsulfonyloxy group can be used, among which the halogen atom is particularly preferred.

The reaction of the compound [II] with the compound [III] or the salt thereof can be carried out in a suitable solvent or without solvent in the presence or absence of an acid acceptor.

As the solvent, any solvents may be suitable as long as it does not adversely affect to the reaction, and, for example, acetonitrile, methanol, ethanol, isopropyl alcohol, propyl alcohol, acetone, dimethylformamide, dimethyl sulfoxide, tetrahydrofuran, ether, dioxane, ethyl acetate, toluene, methylene chloride, dichloroethane, chloroform or a mixed solvent of these solvents can be suitably used.

This reaction suitably proceeds at 0 to 120° C., particularly at room temperature to 80° C.

As the acid acceptor, an inorganic base (for example, alkali metal hydride such as sodium hydride, alkali metal carbonate such as sodium carbonate and potassium carbonate, alkali metal alkoxide such as sodium methoxide, alkali metal such as sodium, and alkali metal hydroxide such as sodium hydroxide and potassium hydroxide, etc.) or an organic base (for example, triethylamine, diisopropylethylamine, N-methylmorpholine, pyridine, dimethylaniline, dimethylaminopyridine, etc.) can be suitably used.

(Process B)

In addition, among the objective compound [I] of the present invention, the compound represented by the formula [I-a]:

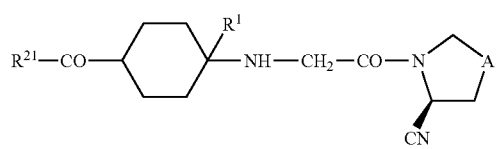

[I-a]

wherein $R^{21}$ represents (1) a monocyclic, bicyclic or tricyclic nitrogen-containing heterocyclic group which may be substituted or (2) an amino group which may be substituted, and represented by the formula:

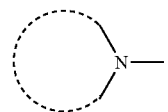

and $R^1$ and A have the same meanings as defined above, can be prepared by reacting a compound represented by the formula [IV]:

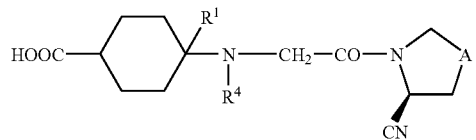

[IV]

wherein $R^4$ represents a protective group for an amino group, and $R^1$ and A have the same meanings as defined above, or a salt thereof with the compound represented by the formula [V]:

$R^{21}$—H or a salt thereof to obtain a compound represented by the formula [VI]:

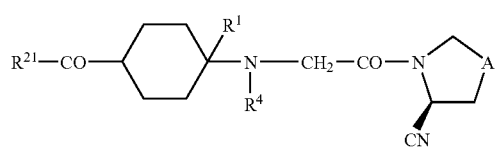

[VI]

wherein $R^1$, $R^4$, $R^{21}$ and A have the same meanings as defined above, or a salt thereof, and by removing the protective group for the amino group ($R^4$) from the product, and optionally, by making the product into a pharmaceutically acceptable salt.

As examples of salts of the compounds [IV] to [VI], a salt with an inorganic acid such as hydrochloride and sulfate, or a salt with an inorganic base such as an alkali metal salt and an alkaline earth metal salt can be used.

As the protective group for the amino group of $R^4$, any of the commonly used protective groups for the amino group such as t-butoxycarbonyl group, benzyloxycarbonyl group, trifluoroacetyl group, chloroacetyl group, 9-fluorenylmethyloxycarbonyl group, etc. can be suitably used.

The reaction of the compound [IV] or a salt thereof with the compound [V] or a salt thereof can be carried out in a suitable solvent or without solvent in the presence or absence of a condensing agent.

As the solvent, any solvents may be suitable as long as it does not adversely affect to the reaction, and, for example, acetonitrile, methanol, ethanol, isopropyl alcohol, propyl alcohol, acetone, dimethylformamide, tetrahydrofuran, ether, dioxane, ethyl acetate, toluene, methylene chloride, dichloroethane, chloroform or a mixed solvent of these solvents can be suitably used.

This reaction suitably proceeds at 0 to 120° C., particularly at room temperature to 80° C.

For the condensing agent, O-benzotriazol-1-yl-N,N,N',N'-tetramethyluroniumhexafluorophosphate, DCC (dicyclohexylcarbodiimide), EDC (1-ethyl-3-(3-dimethylaminopropyl)carbodiimide), chloroformates (for example, ethyl chloroformate and isobutyl chloroformate) and carbonyldiimidazole can be suitably used.

Also, for promoting the reaction, additives such as base (sodium carbonate, sodium hydrogencarbonate, triethylamine, pyridine, 4-dimethylaminopyridine, diisopropylethylamine, 1,8-diazabicyclo[5.4.0]undec-7-ene, etc.), 1-hydroxybenzotriazole, 1-hydroxysuccinimide, etc. can be added to the above condensing agents.

The subsequent removal of the protective group ($R^4$) for the amino group of the compound [VI] can be carried out according to the conventional method, and it can be carried out, for example, in a suitable solvent or without solvent by an acid treatment, base treatment or catalytic reduction.

As the solvent, any solvents may be suitable as long as it does not adversely affect to the reaction, and, for example, methanol, ethanol, isopropyl alcohol, propyl alcohol, dioxane, methylene chloride, chloroform, dichloroethane, ether, tetrahydrofuran, ethyl acetate, toluene or a mixed solvent of these solvents can be suitably used.

This reaction suitably proceeds at −78 to 80° C., particularly at 0° C. to room temperature.

As the acid, an inorganic acid such as hydrochloric acid, sulfuric acid, etc., and an organic acid such as acetic acid, trifluoroacetic acid, methanesulfonic acid, p-toluenesulfonic acid, etc. can be suitably used.

As the base, an inorganic base (for example, alkali metal hydride such as sodium hydride, etc., alkali metal carbonate such as sodium carbonate, potassium carbonate, etc., alkali metal alkoxide such as sodium methoxide, etc., alkali metal such as sodium, etc., and alkali metal hydroxide such as sodium hydroxide, potassium hydroxide, etc.) or an organic base (for example, triethylamine, diisopropylethylamine, morpholine, N-methylmorpholine, pyridine, piperidine, dimethylaniline, dimethylaminopyridine, etc.) can be suitably used.

The catalytic reduction can be carried out by suitably using palladium-carbon, palladium hydroxide-carbon, platinum oxide or Raney nickel under hydrogen atmosphere.

The starting material [II] of the present invention can be prepared, for example, according to the method described in International Patent Publications Nos. WO 98/19998, WO 00/34241, Reference Examples (Reference Example 1 or 2) mentioned below and the like.

For example, the compound [II] can be obtained by reacting a compound represented by the formula [10]:

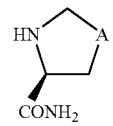

[10]

wherein A has the same meaning as defined above, with a compound represented by the formula [11]:

[11]

wherein $Z^2$ and $Z^3$ represent reactive residues which may be the same or different, in the presence of an acid acceptor (for example, triethylamine) to obtain a compound represented by the formula [12]:

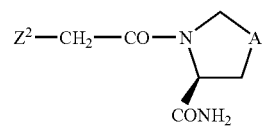

[12]

wherein $Z^2$ and A have the same meanings as defined above, and treating the product with a dehydrating agent (for example, phosphorous oxychloride, trifluoroacetic anhydride, etc.) according to the conventional method.

As the reactive residue of $Z^2$ or $Z^3$, the same reactive residue commonly used as in the above $Z^1$ can be suitably used.

The starting material [III] can be prepared, for example, by the same method as described in Reference Examples (Reference Examples 3 to 14) mentioned below.

For example, the compound [III] in which X is —N($R^3$)— or —O— can be prepared by reacting a compound represented by the formula [13]:

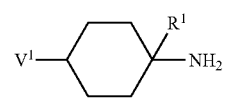

[13]

wherein $V^1$ represents —NH($R^3$)— or hydroxy group, and $R^1$ and $R^3$ have the same meanings as defined above, an amino group-protected material thereof or a salt thereof with a compound represented by the formula [14]:

[14]

wherein $Z^4$ represents a reactive residue and $R^2$ has the same meaning as defined above, in the presence or absence of an acid acceptor (for example, an organic base such as triethylamine, diisopropylethylamine, etc., and an inorganic base such as sodium hydride, potassium carbonate, etc.), and, if necessary, by removing the protective group for the amino group according to the conventional method.

As the protective group for the amino group, any of the same protective groups commonly used as in the above $R^4$ can be suitably used.

As the reactive residue of $Z^4$, the same reactive residues commonly used as in the above $Z^1$ can be suitably used.

For example, the compound [III] in which X is —CO— and $R^2$ is a group represented by the formula:

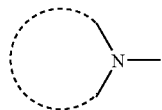

can be produced by reacting a compound represented by the formula [15]:

[15]

wherein $V^2$ represents —COOH and $R^1$ has the same meaning as defined above, an amino group-protected material thereof or a salt thereof with a compound represented by the formula [16]:

  [16]

wherein $R^{22}$ represents (1) a monocyclic, bicyclic or tricyclic nitrogen-containing heterocyclic group which may be substituted or (2) an amino group which may be substituted, represented by the formula:

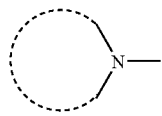

and forms a cyclic or straight amine together with hydrogen atom, or a salt thereof, in the presence of a condensing agent (1-ethyl-3-(3-dimethylaminopropyl)carbodiimide, etc.) and, if necessary, by removing the protective group for the amino group according to the conventional method.

Or else, the compound [III] in which X is —CO— can be obtained by reacting a compound represented by the formula [17]:

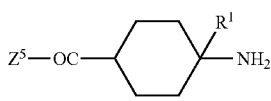
[17]

wherein $Z^5$ represents a reactive residue and $R^1$ has the same meaning as defined above, an amino group-protected material thereof or a salt thereof with a compound represented by the formula [18]:

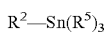  [18]

wherein $R^5$ represents a lower alkyl group and $R^2$ has the same meaning as defined above, in the presence of a palladium catalyst (for example, dichlorobis(triphenylphosphine)palladium, etc.).

As the protective group for the amino group, any of the same protective groups commonly used as in the above $R^4$ can be suitably used. Also, as the reactive residue of $Z^5$, the same reactive residues commonly used as in the above $Z^1$ can be suitably used.

Or else, the compound [III] in which X is —N($R^3$)— can be prepared by reacting the compound represented by the formula [19]:

[19]

wherein $R^1$ has the same meaning as defined above, an amino group-protected material thereof or a salt thereof with the compound represented by the formula [20]:

$R^2$—$V^3$  [20]

wherein $V^3$ represents —N($R^3$) H and $R^2$ has the same meaning as defined above, in the presence of a reducing agent (sodium triacetoxyborohydride, etc.) and, if necessary, by removing the protective group for the amino group according to the conventional method.

As the protective group for the amino group, any of the same protective groups commonly used as in the above $R^4$ can be suitably used.

The starting materials [10] to [20] can be prepared according to known methods or in the same manner as described in Reference Examples mentioned below.

In order to obtain a trans form of the starting material [III] taking a cyclohexane ring as a standard plane, each trans form of the starting cyclohexane compounds (the compounds [13], [15], [17], etc.) may be used.

Also, the starting material [IV] can be prepared, for example, in the same manner as in the process described in Example (Example 3-1, (1) to (3)) mentioned below or in accordance with these processes, as shown in the following figure. (In the figure, $Z^6$ represents a reactive residue, $R^4$ represents a protective group for an amino group and other symbols have the same meanings as defined above.)

As the reactive residue of $Z^6$, the same reactive residues commonly used as in the above $Z^1$ can be suitably used.

[Compound IV]

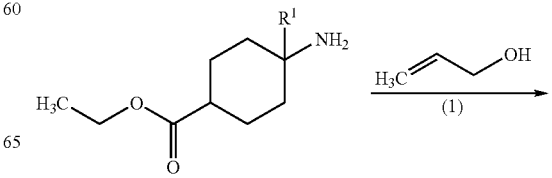

-continued

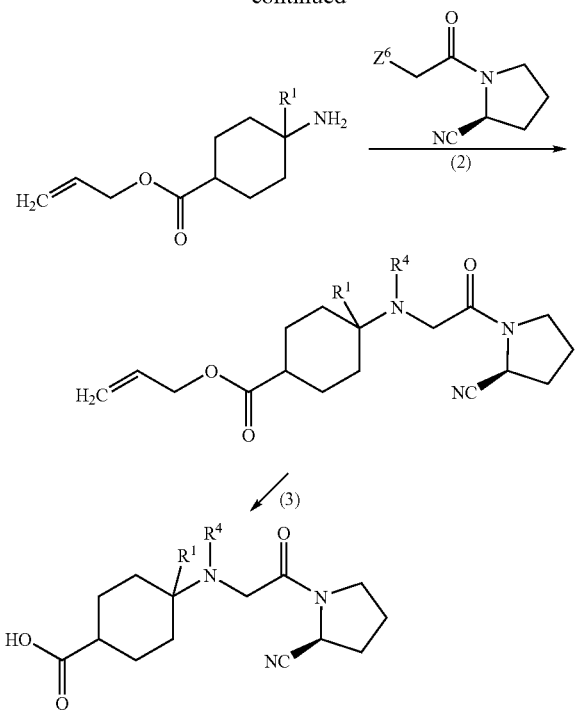

The compound [I] of the present invention or its starting material prepared according to the above is isolated in a free form or as a salt thereof, and purified. The salt can be prepared by subjecting to the salt-forming treatment conventionally used.

Isolation and purification can be carried out by applying the usual chemical operations such as extraction, concentration, crystallization, filtration, recrystallization, various kinds of chromatographies and the like.

In the compound of the present invention, optical isomers such as racemic isomers, optically active isomers, diastereomers, etc. can be present alone or as mixtures thereof. A stereochemically pure isomer can be derived by using a stereochemically pure starting material or by separating an optical isomer according to the general separation process for racemic resolution. Also, diastereomeric mixtures can be separated according to the conventional method, for example, fractional crystallization or by chromatography.

EXAMPLES

The present invention will be described in detail by referring to the following Examples but these Examples do not intend to limit the present invention.

Example 1a-1

A acetonitrile-methanol solution containing 100 mg of (S)-1-bromoacetyl-2-cyanopyrrolidine (Reference Example 1 mentioned below) and 327 mg of N-(5-nitro-2-pyridyl)-trans-1,4-cyclohexanediamine (Reference Example 3-1 mentioned below) was stirred at room temperature for 15 hours. Water was added to the reaction mixture and the mixture was extracted with chloroform. After the extract was dried over sodium sulfate, the solvent was removed under reduced pressure. The residue was purified by diol column chromatography (solvent: 0 to 10% methanol-chloroform) to obtain an oily product. The oily product was dissolved in 0.5 ml of ethyl acetate-0.5 ml of chloroform, and then, 1.0 ml of 2N hydrochloric acid-ether and 2 ml of ether were successively added thereto. Precipitates were collected by filtration and washed with ether to obtain (S)-2-cyano-1-[trans-4-(5-nitro-2-pyridylamino)cyclohexylamino] acetylpyrrolidine-dihydrochloride (Example 1a-1 in Table 1a).

Examples 1a-2 to 1d-152

Using (S)-1-bromoacetyl-2-cyanopyrrolidine and corresponding starting materials, they were treated in the same manner as in Example 1a-1, compounds of Tables 1a to 1d shown below (Examples 1a-2 to 1a-89, 1b-1 to 1b-71, 1c-1 to 1c-52 and 1d-1 to 152) were obtained. Incidentally, the corresponding starting materials were obtained by the similar method as described in Reference Examples mentioned below, by known methods or by a method in combination of these methods.

Provided that the compound of Example 1d-77 was obtained by using trans-4-(1-piperazinylcarbonyl)cyclohexylamine as a starting material.

Also, the compound of Example 1c-39 (namely, (S)-2-cyano-1-{trans-4-[(N-carboxymethyl-N-methylamino)carbonyl]-cyclohexylamino}acetylpyrrolidine.hydrochloride) was obtained by treating the compound of Example 1c-38 (namely, (S)-2-cyano-1-{trans-4-[(N-tert-butoxycarbonylmethyl-N-methylamino)carbonyl] cyclohexylamino}acetylpyrrolidine) with trifluoroacetic acid, followed by treating with hydrochloric acid.

Also, the compound of the Example 1d-14 (namely, (S)-2-cyano-1-[trans-4-(1-piperazinylcarbonyl)cyclohexylamino]-acetylpyrrolidine-dihydrochloride) was obtained by treating a free form of the compound of Example 1d-70 ((S)-2-cyano-1-[trans-4-(4-benzyloxycarbonyl-1-piperazinylcarbonyl)cyclohexylamino]acetylpyrrolidine) with trimethylsilyl iodide.

Examples 2-1 and 2-2

(1) A mixture of 600 mg of 4-tert-butoxycarbonylamino-4-methylcyclohexanone (the compound of Reference Example 6-1, (3)), 783 mg of sodium triacetoxyborohydride, 343 mg of 3-cyanoaniline, 159 mg of acetic acid and 6 ml of dichloroethane was stirred at room temperature for 16 hours. The mixture was diluted with an aqueous saturated sodium hydrogencarbonate solution and then extracted with chloroform. The extract was dried over anhydrous sodium sulfate and the solvent was removed under reduced pressure. The residue was purified by silica gel column chromatography (solvent:hexane-ethyl acetate (4:1) to (1:1)) to obtain 304 mg of N-tert-butoxycarbonyl-1-methyl-c-4-(3-cyano-phenylamino)-r-1-cyclohexylamine and 292 mg of N-tert-butoxycarbonyl-1-methyl-t-4-(3-cyano-phenylamino)-r-1-cyclohexylamine.

(2) 243 mg of N-tert-butoxycarbonyl-1-methyl-c-4-(3-cyanophenylamino)-r-1-cyclohexylamine obtained in the above (1) was stirred in a mixture of 2 ml of 4N hydrochloric acid/dioxane and 2 ml of ethanol at room temperature for 15 hours.

After the reaction mixture was concentrated, to the residue were added 320 mg of (S)-1-bromoacetyl-2-cyanopyrrolidine, 0.6 ml of triethylamine, 3.5 ml of acetonitrile and 1 ml of methanol and the mixture was stirred at room temperature for 15 hours. The mixture was diluted with an aqueous saturated sodium hydrogencarbonate solution and extracted with chloroform. The extract was dried over anhydrous sodium sulfate and the solvent was removed under reduced pressure. The residue was purified by silica gel column chromatography (solvent: chloroform-methanol (50:1)) to obtain 154 mg of the compound, which was then treated with hydrochloric acid to yield (S)-2-cyano-1-[1-methyl-c-4-(3-cyano-phenylamino)-r-1-cyclohexylamino] acetylpyrrolidine-dihydrochloride (Table 2: Example 2-1).

(3) Using N-tert-butoxycarbonyl-1-methyl-t-4-(3-cyanophenylamino)-r-1-cyclohexylamine obtained in the above (1), it was treated in the same manner as in (2), (S)-2-cyano-1-[1-methyl-c-4-(3-cyano-phenylamino)-r-1-cyclohexylamino]-acetylpyrrolidine-dihydrochloride (Example 2-2 in Table 2) was obtained.

Examples 2-3 to 2-8

Using corresponding starting materials, they were treated in the same manner as in Examples 2-1 to 2-2, compounds of Examples 2-3 to 2-8 shown in Table 2 were obtained.

Example 3-1 potassium carbonate solution, water and brine, dried over anhydrous sodium sulfate, and concentrated under reduced pressure. The residue was purified by silica gel flash column chromatography (solvent: chloroform-methanol-aqueous ammonia (500:10:1)) to obtain 3.29 g of trans-4-(2-propenyloxycarbonyl)cyclohexylamine.

(2) A mixture of 507 mg of the compound obtained in the above (1), 400 mg of (S)-1-bromoacetyl-2-cyanopyrrolidine, 714 mg of N,N-diisopropylethylamine and 4 ml of acetonitrile was stirred at 50° C. for 12 hours. After cooling to room temperature, 476 mg of N,N-diisopropylethylamine, followed by 4 ml of acetonitrile solution containing 803 mg of di-tert-butyldicarbonate were added to the reaction mixture, and the mixture was stirred at room temperature for 3 hours. After the reaction mixture was concentrated, the concentrate was diluted with ethyl acetate. The ethyl acetate solution was washed with an aqueous 10% citric acid solution, water and brine, dried over anhydrous sodium sulfate, and concentrated under reduced pressure. The residue was purified by silica gel flash chromatography (solvent: chloroform-methanol (100:1)) to obtain 658 mg of (S)-2-cyano-1-[N-tert-butoxycarbonyl-trans-4-(2-propenyloxycarbonyl)cyclohexylamino]acetylpyrrolidine.

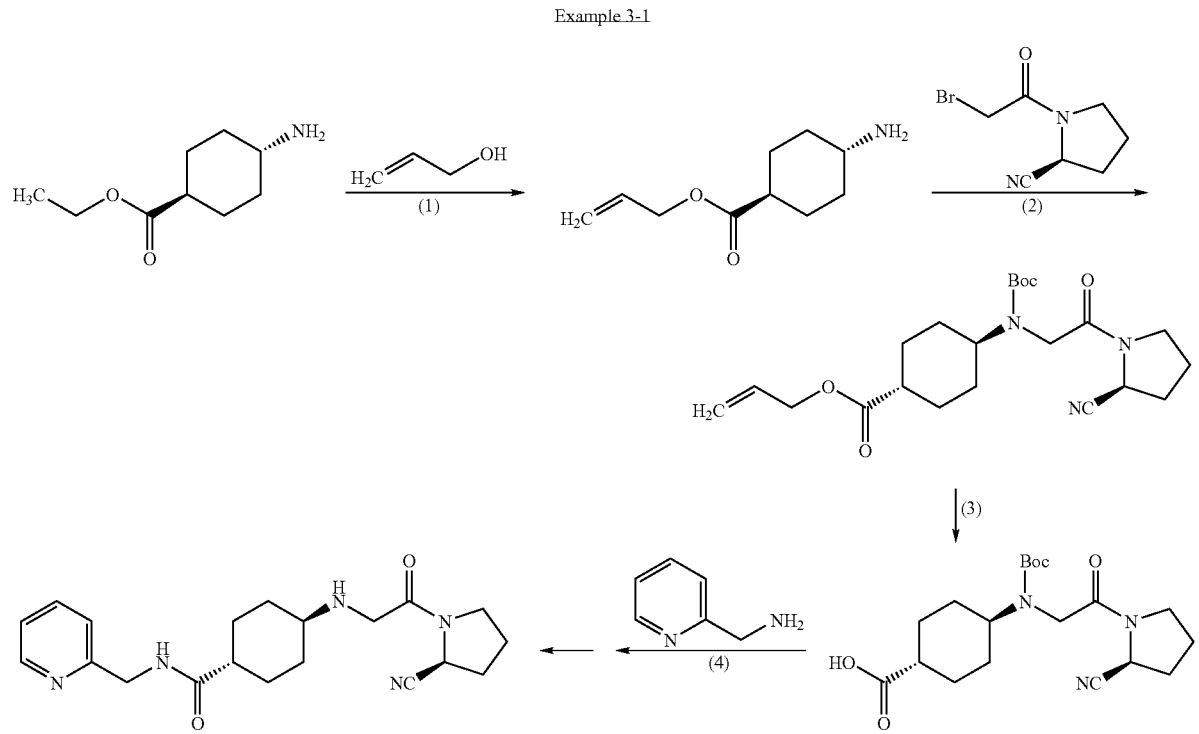

Example 3-1

(1) In water was dissolved 5.0 g of trans-4-ethoxycarbonylcyclohexylamine.dihydrochloride, and after the solution was made basic by adding potassium carbonate, the solution was extracted with chloroform. The extract was washed with brine, dried over anhydrous sodium sulfate, and the solvent was removed under reduced pressure. A mixture of the residue, 5.1 g of p-toluensulfonic acid monohydrate and 50 ml of allyl alcohol was refluxed for 48 hours. The reaction mixture was concentrated, and then, diluted with chloroform. The chloroform solution was washed with an aqueous (3) A mixture of 600 mg of the compound obtained in the above (2), 165 mg of tetrakis(triphenylphosphine)palladium, 271 mg of ammonium formate and 6 ml of dioxane was stirred at 50° C. for 1 hour. After cooling, the reaction mixture was poured into water and extracted with chloroform. The extract was washed with brine, dried over anhydrous sodium sulfate, and then, the solvent was removed under reduced pressure. The residue was purified by silica gel flash chromatography (solvent: chloroform-methanol (50:1)) to obtain 394 mg of (S)-2-cyano-1-(N-tert-butoxy-carbonyl-trans-4-carboxycyclohexylamino)acetylpyrrolidine.

(4) A solution of 2 ml N,N-dimethylformamide containing 150 mg of the compound obtained in the above (3), 64 mg of 2-aminomethylpyridine, 114 mg of 1-ethyl-3-(3-dimethylaminopropyl)-carbodiimide and 80 mg of 1-hydroxybenzotriazole was stirred at room temperature for 24 hours. An aqueous saturated sodium hydrogencarbonate solution was added to the reaction mixture and the mixture was extracted with chloroform. The extract was washed with brine and dried over anhydrous sodium sulfate and the solvent was removed under reduced pressure. The residue was dissolved in 3 ml of acetonitrile, and 1 ml of an acetonitrile solution of 118 mg of trimethylsilyl iodide was added dropwise to the solution under ice-cooling, and the mixture was stirred at room temperature for 30 minutes. To the reaction mixture were added methanol and water, and after stirring for a while, the mixture was neutralized with an aqueous saturated sodium hydrogencarbonate solution, and then, extracted with chloroform. The extract was washed with an aqueous saturated sodium hydrogencarbonate solution, water and brine, dried over anhydrous sodium sulfate, and then, the solvent was removed under reduced pressure. The residue was purified by diol chromatography (solvent:chloroform) to obtain an oily product. The oily product was dissolved in 1 ml of ethyl acetate, and then, 0.5 ml of 1N hydrochloric acid-ether followed by 2 ml of ether were added thereto, and precipitates were washed with ether to obtain 106 mg of (S)-2-cyano-1-[trans-4-(2-pyridylmethylaminocarbonyl)cyclohexylamino]acetylpyrrolidine-dihydrochloride (Example 3-1 in Table 3).

Examples 3-2 to 3-12

The compounds of Examples 3-2 to 3-12 in Table 3 were obtained in the same manner as in Example 3-1 (4), using (S)-2-cyano-1-(N-tert-butoxycarbonyl-trans-4-carboxycyclohexylamino)acetylpyrrolidine (the compound of the above Example 3-1 (3)) and the corresponding starting materials.

Examples 4-1 to 4-32

A solution of 2 ml of acetonitrile-1 ml of methanol containing 100 mg of (R)-3-chloroacetyl-4-cyanothiazolidine (the compound of Reference Example 2 mentioned below) and 372 mg of N-(5-nitro-2-pyridyl)-trans-1,4-cyclohexanediamine was stirred at room temperature for 15 hours. Water was added to the reaction mixture and the mixture was extracted with chloroform. After the extract was dried over anhydrous sodium sulfate, the solvent was removed under reduced pressure. The residue was purified by diol column chromatography (solvent: 0 to 5% methanol-chloroform) to obtain an oily product. The oily product was dissolved in 0.5 ml of ethyl acetate-0.5 ml of chloroform, and 1.0 ml of 2N hydrochloric acid-ether was added thereto, followed by 2 ml of ether. Precipitates were collected by filtration and washed with ether to obtain 173 mg of (R)-4-cyano-3-[trans-4-(5-nitro-2-pyridylamino)cyclohexylamino]-acetylthiazolidine-dihydrochloride (Example 4-1 in Table 4).

Also, the compounds of Examples 4-2 to 4-32 in Table 4 were obtained in the same manner as mentioned above, using the corresponding starting materials.

Reference Example 1

According to the process described in the literature (WO98/19998), (S)-1-bromoacetyl-2-cyanopyrrolidine was obtained by reacting L-prolineamide (commercially available product) and bromoacetyl bromide, followed by dehydration.

Reference Example 2

L-thioprolineamide hydrochloride was synthesized according to the process described in the literature (Ashworth et. al., Bioorg. Med. Chem. Lett., Vol. 6, pp. 2745–2748, 1996). 2.36 ml of chloroacetyl chloride was added to a solution of 150 ml of dichloromethane containing 5.00 g of L-thioprolineamide hydrochloride thus obtained and 8.67 ml of triethylamine under ice-cooling, and the mixture was stirred at the same temperature for 1 hour. To the reaction mixture was added a dichloromethane solution containing 4.8 ml of pyridine and 8.4 ml of trifluoroacetic anhydride, and the mixture was further stirred at room temperature for 1 hour. The reaction mixture was washed with an aqueous 10% HCl solution and water, dried over anhydrous magnesium sulfate, filtered and concentrated under reduced pressure, and subsequently, the residue was crystallized from ether to obtain 4.82 g of (R)-3-chloroacetyl-4-cyanothiazolidine as yellow-brownish crystals.

Reference Examples 3-1 to 3-40

A solution of 5-nitro-2-chloropyridine (2.50 g) and trans-1,4-cyclohexanediamine (5.40 g) in ethanol (15 ml)tetrahydrofuran (10 ml) was stirred at room temperature for 5 days. The precipitates were removed by filtration and the filtrate was concentrated under reduced pressure. The residue was purified by silica gel column chromatography (solvent: chloroform-methanol-concentrated aqueous ammonia (20:4:1)) and crystallized from ethyl acetate to obtain N-(5-nitro-2-pyridyl)-trans-1,4-cyclohexanediamine (Reference Example 3-1 in Table 5).

Also, the compounds of Examples 3-2 to 3-40 in Table 5 were obtained in the same manner as mentioned above, using the corresponding starting materials.

Reference Examples 3-41 to 3-44

A N,N-dimethylacetamide (30 ml) solution containing 4-nitrofluorobenzene (1.69 g) and trans-1,4-cyclohexanediamine (4.1 g) was stirred at 144-C for 3 days. After cooling, an aqueous saturated potassium carbonate solution was added to the reaction solution, and the reaction mixture was extracted with ethyl acetate. The extract was dried over anhydrous potassium carbonate, and then, the solvent was removed under reduced pressure. The residue was purified by silica gel flash column chromatography (solvent: chloroform-methanol-ammonia (90:10:1)), and the solvent was removed to obtain trans-N-(4-nitrophenyl)-1,4-cyclohexanediamine (Reference Example 3-41 in Table 5) (2.31 g).

Also, the compounds of Examples 3-42 to 3-44 in Table were obtained in the same manner as mentioned above, using the corresponding starting materials.

Reference Examples 3-45 to 3-47

25 mL of an ethanol solution containing 1.23 g of N-tert-butoxycarbonyl-trans-1,4-cyclohexanediamine, 1.0 g of 2-chloro-3-nitro-pyridine 1-oxide and 700 mg of dimethylaminopyridine was refluxed under argon atmosphere for 2 hours.

After cooling, the reaction solution was concentrated under reduced pressure, the residue was dissolved in chloroform, washed with water, dried over anhydrous sodium sulfate, and then, the solvent was removed under reduced pressure. The obtained residue was purified by silica gel flash column chromatography (solvent: chloroform-methanol (30:1)) to obtain red powder. The resulting compound was dissolved in 5 mL of trifluoroacetic acid and the solution was stirred at room temperature for 3 hours. After the solvent was removed under reduced pressure, the residue was purified by silica gel flash column chromatography (solvent:aqueous ammonia-saturated chloroform-methanol (10:1)) to obtain 110 mg of N-(3-nitropyridine-1-oxid-2-yl)-trans-1,4-cyclohexanediamine (Reference Example 3-45 in Table 5).

Also, the compounds of Examples 3-46 to 3-47 in Table 5 were obtained in the same manner as mentioned above, using corresponding starting materials.

Reference Examples 3-48 to 3-49

In the mixed solvent of 5 ml of ethanol and 4 ml of tetrahydrofuran were dissolved 168 mg of N-tert-butoxycarbonyl-trans-4-[(6-chloro-3-pyridazinyl)amino]cyclohexylamine (Reference Example 3-46) and 0.5 ml of triethylamine. To the solution was added 50 mg of 10% palladium carbon and the mixture was stirred under hydrogen atmosphere with normal pressure at room temperature for 1 day. After the catalyst was removed by filtration, the solvent was removed, and the residue was stirred in 2 ml of trifluoroacetic acid for 3 hours. The solvent was removed, an aqueous 10% sodium hydroxide solution was added to the residue, the mixture was extracted with chloroform and dried over anhydrous sodium sulfate. Subsequently, the solvent was removed under reduced pressure to obtain 61 mg of trans-4-(pyridazin-3-ylamino)cyclohexylamine (Reference Example 3-48 in Table 5).

Also, the compound of Example 3-49 in Table 5 was obtained by treating the corresponding starting material (Reference Example 3-47) in the same manner as mentioned above.

Reference Examples 3-50 to 3-58

Also, the compounds of Examples 3-50 to 3-58 in Table 5 were obtained in the same manner as in Reference Example 9-50 or Reference Example 9-55.

Reference Example 3-59

Ethyl 4-chloro-2-phenyl-5-pyrimidinecarboxylate and N-tert-butoxycarbonyl-trans-1,4-cyclohexanediamine were reacted in ethanol in the presence of dimethylaminopyridine in the same manner as in Reference Example 3-49 to obtain N-tert-butoxycarbonyl-trans-4-(5-ethoxycarbonyl-2-phenyl-4-pyrimidinylamino)cyclohexylamine.

The compound was treated in the same manner as in Reference Example 9-56 (1) and (2) to obtain trans-4-(5-morpholinocarbonyl-2-phenyl-4-pyrimidinylamino)cyclohexylamine (Reference 3-59 in Table 5).

Reference Example 4

(1) To 150 ml of a tetrahydrofuran suspension containing 10 g of trans-4-aminocyclohexanol was added 15 ml of triethylamine, 50 ml of a tetrahydrofuran solution containing 2-chloro-5-nitropyridine was further added thereto under ice-cooling, and then, the mixture was stirred at room temperature for 18 hours. Water was added to the reaction mixture and the mixture was extracted with chloroform. The extract was washed with brine, dried over anhydrous sodium sulfate, and the solvent was removed under reduced pressure. The residue was purified by silica gel flash column chromatography (solvent: ethyl acetate-hexane (2:1)) to obtain 8.52 g of trans-4-(5-nitro-2-pyridylamino)cyclohexanol.

(2) To 10 ml of a dichloromethane solution containing 1.0 g of the compound obtained in the above (1) was added 1.8 ml of triethylamine, 0.65 ml of methanesulfonyl chloride was further added thereto under ice-cooling, and the mixture was stirred for 1 hour. An aqueous saturated sodium bicarbonate solution was added to the reaction mixture and the mixture was extracted with chloroform. The extract was washed with water and brine, dried over anhydrous sodium sulfate, and then, the solvent was removed under reduced pressure. 1.37 g of sodium azide was added to a solution of the residue dissolved in 10 ml of dimethylformamide and the mixture was stirred at 50° C. for 3 days. After cooling, an aqueous saturated sodium bicarbonate solution was added to the reaction mixture and the mixture was extracted with ethyl acetate. The extract was washed with water and brine, dried over sodium sulfate, and then, the solvent was removed under reduced pressure. The residue was purified by silica gel flash column chromatography (solvent: ethyl acetate-hexane (1:5)) to obtain 758 mg of cis-4-azide-N-(5-nitro-2-pyridyl)cyclohexylamine.

(3) A solution comprising 10 ml of tetrahydrofuran-1 ml of water, containing 640 mg of the compound obtained in the above (2) and 704 mg of triphenylphosphine was stirred at room temperature for 2 days. The reaction mixture was concentrated, and the residue was purified by silica gel flash column chromatography (solvent: ethyl acetatemethanol (10:1)) to obtain 531 mg of N-(5-nitro-2-pyridyl)-cis-1,4-cyclohexanediamine (the compound of Reference Example 4 in Table 5).

Reference Examples 5-1 to 5-6

(1) In 600 mL of dimethylformamide were suspended 60.0 g of trans-4-tert-butoxycarbonylaminocyclohexyl methanesulfonate and 20.1 g of sodium azide and the suspension was stirred at 90° C. for 6 hours. The reaction mixture was poured into water and extracted with ethyl acetate. The extract was washed with water and brine, dried over anhydrous sodium sulfate, and then, the solvent was removed under reduced pressure to obtain 47.9 g of cis-4-azide-N-(tert-butoxycarbonyl)cyclohexylamine.

(2) In 8 mL of tetrahydrofuran were suspended 500 mg of the compound obtained in the above (1) and 100 mg of palladium-carbon (wet) and the suspension was vigorously stirred under hydrogen atmosphere at room temperature for 1.5 hours. During the course, hydrogen in the system was replaced twice. The insolubles were removed by filtration, and the filtrate was concentrated under reduced pressure. The residue was purified by silica gel chromatography (solvent:chloroform-methanol (20:1), followed by chloroform-methanol-aqueous ammonia (100:10:1)) to obtain 395 mg of N-tert-butoxycarbonyl-cis-1,4-cyclohexanediamine.

(3) A suspension comprising 10 mL of 2-propanol, 2.0 g of the compound obtained in the above (2), 1.63 g of 2-chloro-3-nitropyridine and 1.95 mL of diisopropylethylamine was stirred at 80° C. for 1 day. After the reaction mixture was concentrated under reduced pressure, water was added thereto and the mixture was extracted with ethyl acetate. The extract was washed with brine, dried over anhydrous sodium sulfate, and then, the solvent was removed under reduced pressure. The residue was purified by silica gel chromatography (solvent: chloroform, followed by chloroform-ethyl acetate (7:1)). To a suspension of the resultant compound in ethanol was added hydrochloric acid-dioxane, the mixture was stirred at room temperature for 18 hours, and the precipitates were collected by filtration to obtain 2.15 g of N-(3-nitro-2-pyridyl)-cis-1,4-cyclohexanediamine dihydrochloride (Reference Example 5-1 in Table 5).

Also, the compounds of Reference Examples 5-2 to 5-6 in Table 5 were obtained in the same manner as mentioned above, using the corresponding starting materials.

Reference Example 6-1

(The starting materials were synthesized according to the process described in the literature by Rosemmund et al. (Chem. Ber., 1975, Vol. 108, pp. 1871–1895) and the literature by Black et al. (Synthesis, 1981, p. 829).)

(2) A mixture of 3.80 g of the compound obtained in the above (1), 3.55 g of sodium hydroxide, 16 mL of methanol and 25 mL of water was refluxed for 2 hours. The reaction mixture was ice-cooled, adjusted its pH to 5 by 2N hydrochloric acid and an aqueous 10% citric acid solution, and extracted with ethyl acetate. The extract was washed with water and brine, dried over anhydrous sodium sulfate and the solvent was removed under reduced pressure to obtain 3.46 g of 8-methyl-1,4-dioxaspiro[4.5]decan-8-carboxylic acid (the compound (2) of the above figure).

(3) A mixture comprising 16.19 g of the compound obtained in the above (2), 24.51 g of diphenylphosphoryl azide, 9.00 g of triethylamine and 160 mL of toluene was refluxed for 2.5 hours. The reaction mixture was ice-cooled, washed with an aqueous saturated sodium hydrogencarbonate solution, water and brine, dried over anhydrous sodium sulfate, and the solvent was removed under reduced pressure. To a solution of the resulting compound in 100 mL of dimethylacetamide was gradually added 9.55 g of potassium tert-butoxide under ice-cooling, and the mixture was stirred at

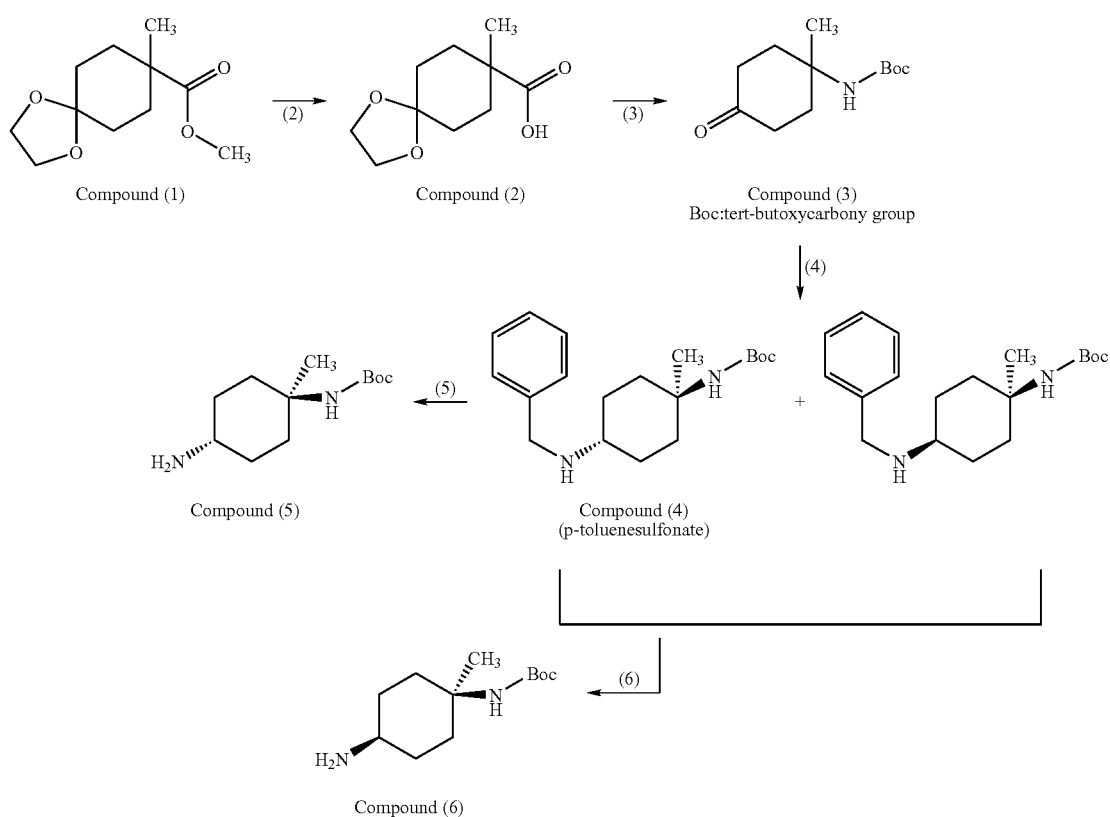

(1) According to the process described in the literature (JP83-118577), methyl 1,4-dioxaspiro[4.5]decan-8-carboxylate was reacted with methyl iodide in the presence of LDA (lithium diisopropylamide) to obtain methyl 8-methyl-1,4-dioxaspiro[4.5]decan-8-carboxylate (the compound (1) of the above figure).

room temperature for 1 hour. The reaction mixture was poured into ice-water, and the precipitated crystals were collected by filtration, washed with water and dried. To a solution of the resulting compound in 100 mL of tetrahydrofuran was added 100 mL of an aqueous solution containing 30.87 g of p-toluenesulfonic acid hydrate, and the mixture was stirred at room temperature for 16 hours. The mixture was diluted with an aqueous saturated sodium hydrogencarbonate solution and extracted with ethyl acetate. The extract was washed with water and brine, dried over anhydrous sodium sulfate, and the solvent was removed under reduced pressure to obtain 10.41 g of 4-tert-butoxycarbonylamino-4-methylcyclohexanone (the compound (3) of the above figure).

(4) A mixture comprising 10.41 g of the compound obtained in the above (3), 11.01 g of sodium triacetoxyborohydride, 5.10 mL of benzylamine and 150 mL of methylene chloride was stirred at room temperature for 16 hours. The mixture was diluted with an aqueous saturated sodium hydrogencarbonate solution and extracted with ethyl acetate. The extract was washed with water and brine, dried over anhydrous sodium sulfate, and the solvent was removed under reduced pressure. To a solution of the resulting compound in 15 mL of methanol was added 3.32 g of p-toluenesulfonic acid hydrate, followed by 160 mL of ether. The precipitates were collected by filtration, washed with ether and dried to obtain 7.49 g of N-benzyl-t-4-tert-butoxycarbonylamino-4-methyl-r-1-cyclohexylamine p-toluenesulfonate (the compound (4) of the above figure).

(5) A mixture comprising 16.63 g of the compound obtained in the above (4), 5.0 g of 10% palladium-carbon and 400 mL of methanol was stirred under hydrogen atmosphere (1 atm) for 24 hours. 10% palladium-carbon was removed by filtration and the filtrate was concentrated. The resulting residue was dissolved in a mixture of 50 mL of an aqueous 10% sodium hydroxide solution and 300 mL of ether, the ether layer was washed with water and brine, dried over anhydrous sodium sulfate, and the solvent was removed under reduced pressure to obtain 6.87 g of t-4-tert-butoxycarbonylamino-4-methyl-r-1-cyclohexylamine (the compound (5) of the above figure).

(6) The filtrate in the step of the above (4) was treated with an aqueous sodium hydroxide solution and extracted with chloroform. The extract was washed with water and brine, dried over anhydrous sodium sulfate, and the solvent was removed under reduced pressure. The residue was applied to NH-silica gel column chromatography (solvent:hexane-ethyl acetate (30:1 to 3:1) to obtain N-benzyl-c-4-tert-butoxycarbonylamino-4-methyl-r-1-cyclohexylamine. Then, this compound was treated in the same manner as described in the above (5) to obtain c-4-tert-butoxycarbonylamino-4-methyl-r-1-cyclohexylamine (the compound (6) of the above figure).

Reference Example 6-2

In the same manner as in Reference Example 6-1 (1) to (5) or (6) except for using benzyloxymethyl chloride instead of methyl iodide in the step of Reference Example 6-1 (1), t-4-tert-butoxycarbonylamino-4-hydroxymethyl-r-1 -cyclohexylamine or c-4-tert-butoxycarbonylamino-4-hydroxymethyl-r-1-cyclohexylamine was obtained.

Also, in the same manner as in Reference Example 6-1 (1) to (5) or (6) except for using methoxymethyl chloride instead of methyl iodide in the step of Reference Example 6-1 (1), t-4-tert-butoxycarbonylamino-4-methoxymethyl-r-1-cyclohexylamine or c-4-tert-butoxycarbonylamino-4-methoxymethyl-r-1-cyclohexylamine was obtained.

Reference Examples 7-1 to 7-18

A mixture comprising 1.70 g of t-4-tert-butoxycarbonylamino-4-methyl-r-1-cyclohexylamine (the compound obtained in the above Reference Example 6-1 (5)), 2.04 g of 2-chloropyrimidine, 3.24 mL of diisopropylethylamine and 13 mL of 2-propanol was refluxed for 12 hours. After cooling, the reaction mixture was diluted with water and extracted with ethyl acetate. The extract was washed with water and brine, dried over anhydrous sodium sulfate, and the solvent was removed under reduced pressure. The residue was purified by silica gel column chromatography (solvent: ethyl acetate-hexane (30:70 to 50:50). The resulting compound was dissolved in 4 mL of dioxane, 10 mL of 4N hydrochloric acid-dioxane was added thereto, and the mixture was stirred for 8 hours. The reaction mixture was diluted with ether and the precipitated crystals were collected by filtration and washed with ether. The resulting crystals were dissolved in water, which was saturated with potassium carbonate, subsequently extracted with chloroform. The extract was dried over anhydrous sodium sulfate, and the solvent was removed under reduced pressure to obtain 587 mg of 1-methyl-t-4-(2-pyrimidinylamino)-r-1-cyclohexylamine (Reference Example 7-1 in Table 5).

Also, the compounds of Reference Examples 7-2 to 7-5 in Table 5 were obtained in the same manner as mentioned above, using the corresponding starting materials.

Also, the compounds of Reference Examples 7-6 to 7-9 in Table 5 were obtained in the same manner as mentioned above, using c-4-tert-butoxycarbonylamino-4-methyl-r-1-cyclohexylamine (the compound obtained in the above Reference Example 6-1, (6)) and the corresponding starting materials.

Also, the compounds of Reference Examples 7-10 to 7-18 in Table 5 were obtained in the same manner as mentioned above, using t- or c-4-tert-butoxycarbonylamino-4-hydroxymethyl-r-1-cyclohexylamine (Reference Example 6-2) and the corresponding starting materials.

Reference Examples 7-19 to 7-23

4-tert-Butoxycarbonylamino-4-methylcyclohexanone (the compound (3) of Reference Example 6-1) and the corresponding starting materials (an amine compounds) were reacted in the presence of sodium triacetoxyborohydride at room temperature for 16 hours under stirring, and then, an acid treatment of the reaction mixture was carried out to remove a protective group (t-butoxycarbonyl group), to obtain the compounds of Reference Examples 7-19 to 7-23 in Table 5.

Reference Examples 8-1 to 8-4

(1) To 160 ml of a methylene chloride solution containing 16.93 g of 4-(tert-butoxycarbonylamino)cyclohexanone and 0.10.55 ml of N-methylbenzylamine was added 19.08 g of sodium triacetoxyborohydride under ice-cooling, and the mixture was stirred at room temperature for 14 hours. The reaction mixture was diluted with an aqueous sodium hydrogencarbonate solution and extracted with ethyl acetate. The extract was washed with water and brine, dried over anhydrous sodium sulfate, and then, the solvent was removed under reduced pressure. The resulting residue was suspended in hexane and collected by filtration. This mother liquor was concentrated, and the residue was purified by NH-silica gel chromatography (solvent: hexane-ethyl acetate (97:3 to 83:17), and the residue was further suspended in hexane and collected by filtration, whereby it was combined with the product previously obtained by filtration to give 13.55 g of N'-benzyl-N-tert-butoxycarbonyl-N'-methyl-trans-1,4-cyclohxanediamine.

A suspension of 13.53 g of this compound and 2.00 g of palladium hydroxide-carbon suspended in methanol was subjected to catalytic hydrogenation under normal pressure at room temperature over 5 hours. The catalyst was removed by filtration and the filtrate was concentrated under reduced pressure to obtain 9.93 g of N-tert-butoxycarbonyl-N'-methyl-trans-1,4-cyclohexanediamine.

(2) The compound obtained in the above (1) and the corresponding starting materials (chloride) were used and reacted under reflux in 2-propanol in the presence of diisopropylethylamine for 12 hours as in Reference Example 7-1, and the resulting compound was subjected to acid treatment with hydrochloric acid, and then, neutralized with potassium carbonate to obtain the compounds of Reference Examples 8-1 to 8-4 in Table 5.

Reference Examples 9-1 to 9-45

2.04 g of 60% sodium hydride was gradually added to 150 ml of a tetrahydrofuran solution containing 10.0 g of trans-4-(tert-butoxycarbonylamino)cyclohexanol and 7.35 g of 2-chloro-5-nitropyridine, and 30 mL of dimethylsulfoxide was further added thereto, and then, the mixture was stirred at room temperature for 1 day. The reaction mixture was poured into water and extracted with chloroform. The extract was washed with water and brine, dried over anhydrous sodium sulfate, and then, the solvent was removed under reduced pressure. The residue was applied to silica gel column chromatography (solvent: chloroform alone to chloroform-ethyl acetate (20:1)). The obtained powder crystals were suspended in ethyl acetate-hexane mixed solution and collected by filtration to obtain 12.20 g of trans-1-tert-butoxycarbonylamino-4-(5-nitro-2-pyridyloxy)-cyclohexane. To 10 ml of an ethanol suspension containing 800 mg of this compound was added 2 ml of 2N hydrochloric acid-dioxane solution, and the mixture was stirred at room temperature for 18 hours. The precipitates were collected by filtration to obtain 568 mg of trans-4-(5-nitro-2-pyridyloxy)cyclohexylamine.hydrochloride (Reference Example 9-1 in Table 6).

Also, the compounds of Reference Examples 9-2 to 9-45 in Table 6 were obtained in the same manner as mentioned above, using the corresponding starting materials.

Reference Examples 9-46 to 9-47

60% sodium hydride was added to 10 ml of a tetrahydrofuran suspension containing 1.00 g of trans-4-aminocyclohexanol hydrochloride and the mixture was refluxed for 1 hour. After cooling to room temperature, 2-chloropyrimidine was slowly added thereto and the mixture was stirred at room temperature for 6 hours. The reaction mixture was poured into ice-cold water and extracted with chloroform. The extract was washed with brine and dried over anhydrous sodium sulfate, and then, the solvent was removed under reduced pressure. The residue was purified by NH-silica gel column chromatography (solvent: ethyl acetate-hexane (1:4) to chloroform alone) to obtain 788 mg of trans-4-(2-pyrimidinyloxy)cyclohexylamine (Reference Example 9-46 in Table 6).

Also, the compound of Examples 9-47 in Table 6 was obtained in the same manner as mentioned above, using the corresponding starting materials.

Reference Example 9-48

In the same manner as in Reference Example 9-1, trans-1-tert-butoxycarbonylamino-4-(3-nitro-2-pyridyloxy)-cyclohexane was obtained. Subsequently, a suspension of 3.35 g of this compound in 30 ml of ethanol was stirred at 50° C., and 155 mg of palladium-carbon (dry) and then 1.6 ml of hydrazine monohydrate were added thereto. After the mixture was stirred for 10 minutes, 185 mg of the remaining palladium-carbon was added thereto and the mixture was refluxed for 40 minutes. After the reaction mixture was cooled to room temperature, the insolubles were removed by filtration and the filtrate was concentrated under reduced pressure. The resulting residue was crystallized from ethanol-water (1:1) and the crystals were collected by filtration to obtain 2.58 g of trans-1-tert-butoxycarbonylamino-4-(3-amino-2-pyridyloxy)cyclohexane.

Then, hydrochloric acid-dioxane was added to an ethanol solution of this compound to subject to acid treatment to obtain trans-4-(3-amino-2-pyridyloxy)cyclohexylamine-hydrochloride (Reference Example 9-48 in Table 6).

Reference Example 9-49

In the same manner as in Reference Example 9-1 by using trans-4-(tert-butoxycarbonylamino)cyclohexanol and the corresponding starting materials, trans-4-(5-ethoxycarbonyl-2-methylthiopyrimidin-4-yloxy)cyclohexylamine hydrochloride was obtained.

The hydrochloride compound was made into an aqueous solution, and the solution was treated with potassium carbonate and extracted with chloroform to obtain its free form (Reference Example 9-49).

Reference Examples 9-50 to 9-54

In 50 mL of chloroform was dissolved 2.75 g of N-tert-butoxycarbonyl-trans-4-(5-ethoxycarbonyl-2-methylthiopyrimidin-4-yloxy)cyclohexylamine (a compound of Reference Example 9-49 prior to deprotection (hydrochloric acid-dioxane treatment)), 1.73 g of 75%-m-chloroperbenzoic acid was added to the solution, and the mixture was stirred at room temperature for 30 minutes. Then, 1.14 g of dimethylamine hydrochloride and 2.79 mL of triethylamine were added thereto and the mixture was further stirred for 5 hours. An aqueous saturated sodium hydrogencarbonate solution was added to the reaction mixture, and the mixture was stirred. Then, the chloroform layer was collected by separation, dried over anhydrous sodium sulfate and the solvent was removed under reduced pressure. The residue was purified by silica gel flash chromatography (solvent: hexane-chloroform (50:50 to 100:0)) to obtain 2.74 g of N-tert-butoxycarbonyl-trans-4-[5-ethoxycarbonyl-2-(dimethylamino)-pyrimidin- 4-yloxy]cyclohexylamine.

This compound was deprotected by treating with hydrochloric acid-dioxane, and subsequently neutralized with potassium carbonate to obtain trans-4-[5-ethoxycarbonyl-2-(dimethylamino)pyrimidin-4-yloxy]cyclohexylamine (Reference Example 9-50 in Table 6).

Also, the compounds of Reference Examples 9-51 to 9-54 in Table 6 were obtained in the same manner as mentioned above.

Reference Examples 9-55 to 9-57

(1) In 15 mL of ethanol was dissolved 2.675 g of N-tert-butoxycarbonyl-trans-4-[5-ethoxycarbonyl-2-(dimethylamino)pyrimidin-4-yloxy]cyclohexylamine (the compound of Reference Example 9-50 prior to deprotection treatment), 3.27 mL of an aqueous 3N-sodium hydroxide solution was added thereto at room temperature, and the mixture was stirred overnight. The reaction mixture was diluted with water, and then, citric acid was added thereto until the solution became neutral. The precipitated crystals were collected by filtration, washed with water and dried under reduced pressure to obtain 2.015 g of N-tert-butoxycarbonyl-trans-4-[5-carboxy-2-(dimethylamino)pyrimidin-4-yloxy]cyclohexylamine.

(2) The compound obtained in the above (1) was used as a starting material and reacted with a starting amine compound in the same manner as in Reference Example 11-1. The resulting compound (hydrochloride) was made into an aqueous solution, and the solution was treated with potassium carbonate and extracted with chloroform to obtain a free form.

Thus, the compounds of Reference Examples 9-55 to 9-57 in Table 6 were obtained.

Reference Examples 9-58 to 9-64

(1) 0.494 ml of DMSO was slowly added dropwise to 10 ml of a methylene chloride solution containing 0.526 ml of oxalyl chloride under argon gas atmosphere at −78° C. After 15 minutes from the completion of the addition, 30 ml of a methylene chloride suspension containing trans-4-tert-butoxycarbonylaminocyclohexanol in was added dropwise, and further 30 minutes later, 2.52 ml of triethylamine was added thereto and the mixture was stirred at −78° C. for 30 minutes and at 0° C. for 15 minutes. An aqueous sodium bicarbonate solution was added to the reaction mixture and the mixture was extracted with chloroform. The extract was dried over anhydrous sodium sulfate, and then, the solvent was removed under reduced pressure. The resulting residue was suspended in a hexane-isopropyl ether mixed solvent and collected by filtration to obtain 0.903 g of 4-(tert-butoxycarbonylamino)cyclohexanone.

(2) To 350 ml of a toluene solution containing 33.05 g of the compound obtained in the above (1) was added dropwise 313 ml of 1.0 M diisobutyl aluminum hydride-toluene solution at −78° C., and the mixture was stirred at the same temperature for 4 hours. After an excessive reagent was decomposed by adding 33 ml of methanol dropwise to the mixture, 100 ml of water was added thereto, and the mixture was stirred for 1 hour. The precipitated insolubles were removed by filtration. The organic layer of the filtrate was separated and dried over anhydrous sodium sulfate. The solvent was removed under reduced pressure, the resulting residue was suspended in chloroform-isopropyl ether mixed solvent under heating and the insolubles were removed by filtration. The filtrate was concentrated, and then, the same operation was performed with isopropyl ether. The resulting filtrate was concentrated and the residue was purified by silica gel flash column chromatography (solvent: ethyl acetate-hexane (1:2 to 1:1)), and the obtained colorless crystals were further suspended in hexane-isopropyl ether mixed solvent under heating and subjected to filtration at 0° C. to obtain 6.95 g of cis-4-tert-butoxycarbonylaminocyclohexanol.

(3) The compounds of Reference Examples 9-58 to 9-64 in Table 6 were obtained in the same manner as in Reference Example 9-1, using the above-obtained cis-4-tert-butoxycarbonylaminocyclohexanol and the corresponding starting materials.

Reference Example 10-1

(1) A mixture comprising 9.13 g of 4-tert-butoxycarbonylamino-4-methylcyclohexanone, 3.05 g of sodium borohydride and 100 mL of isopropyl alcohol was stirred at room temperature for 1 hour. Under ice-cooling, the reaction mixture was diluted with an aqueous saturated ammonium chloride solution and extracted with ethyl acetate. The resulting extract was washed with water and brine, dried over anhydrous sodium sulfate, and then, the solvent was removed under reduced pressure to obtain 9.20 g of a mixture of t-4-tert-butoxycarbonylamino-4-methyl-r-1-cyclohexanol and c-4-tert-butoxycarbonylamino-4-methyl-r-1-cyclohexanol.

(2) A mixture comprising 9.20 g of the compound obtained in the above (1), 8.26 g of p-methoxybenzoic acid chloride, 5.93 g of dimethylaminopyridine and 100 mL of methylene chloride was refluxed for 20 hours. After cooling, the reaction mixture was washed with an aqueous saturated sodium hydrogencarbonate solution, an aqueous 10% citric acid solution, water and brine, dried over anhydrous sodium sulfate, and then, the solvent was removed. The residue was crystallized from n-hexane to obtain 0.68 g of c-4-tert-butoxycarbonylamino-4-methyl-O-(4-methoxyphenylcarbonyl)-r-1-cyclohexanol (cis compound).

Also, the residue was purified by silica gel column chromatography [solvent:ethyl acetate/n-hexane (1/10)] to obtain 3.50 g of a mixture (1:5) of the above compound (cis compound) and t-4-tert-butoxycarbonylamino-4-methyl-O-(4-methoxyphenylcarbonyl)-r-1-cyclohexanol (trans compound).

(3) A mixture comprising 10.68 g of the cis compound obtained in the above (2), 6.10 g of sodium hydroxide, 150 mL of methanol and 120 mL of water was heated at external temperature of 75° C. for 1 hour. After cooling the reaction mixture, the solvent was removed under reduced pressure and extracted with ethyl acetate. The extract was washed with an aqueous saturated sodium hydrogencarbonate solution, water and brine, dried over anhydrous sodium sulfate, and then, the solvent was removed under reduced pressure to obtain 6.61 g of c-4-tert-butoxycarbonylamino-4-methyl-r-1-cyclohexanol.

(4) In the same manner as in the above (3) by using 3.50 g of the mixture (1:5) of cis form and trans form obtained in the above (2), 1.77 g of t-4-tert-butoxycarbonylamino-4-methyl-r-1-cyclohexanol was obtained.

Reference Examples 10-2 to 10-8

The compounds of Reference Examples 10-2 and 10-3 in Table 6 were obtained in the same manner as in Reference Example 9-1 by using t-4-tert-butoxycarbonylamino-4-methyl-r-1-cyclohexanol (Reference Example 10-1 (4)) and the corresponding starting materials. Also, the compounds of Reference Examples 10-4 to 10-8 in Table 6 were obtained in the same manner as mentioned above by using c-4-tert-butoxycarbonylamino-4-methyl-r-1-cyclohexanol (Reference Example 10-1 (3)) and the corresponding starting materials.

Reference Examples 11-1 to 11-38 and 12-1 to 12-96

A mixture comprising 500 mg of trans-4-(tert-butoxycarbonylamino)cyclohexanecarboxylic acid, 250 mg of N-methyl-benzylamine, 434 mg of 1-(3-dimethylaminopropyl)-3-ethylcarbodiimide hydrochloride, 306 mg of 1-hydroxybenzotriazol and 5 ml of N,N-dimethylformamide was stirred at room temperature for 15 hours. The reaction mixture was made basic by adding an aqueous sodium hydrogencarbonate solution, and extracted with ethyl acetate. The extract was washed with water and brine, dried over anhydrous sodium sulfate, and then, the solvent was removed under reduced pressure to obtain 691 mg of N-benzyl-trans-4-tert-butoxycarbonylamino-N-methylcyclohexanecarboxamide. A mixture comprising 670 mg of this compound, 5 mL of 4N-hydrochloric acid-dioxane and 5 ml of dioxane was stirred at room temperature for 12 hours. The reaction mixture was concentrated to obtain 585 mg of trans-4-amino-N-benzyl-N-methylcyclohexanecarboxamide hydrochloride (Reference Example 11-1 in Table 7).

Also, the compounds of Reference Examples of 11-2 to 11-38 and 12-1 to 12-96 in Table 7 and Table 8 mentioned below were obtained in the same manner as mentioned above by using the corresponding starting amine compounds (straight chain amine compounds or cyclic secondary-amine compounds such as a piperidine compound, a piperazine compound, etc.). (Provided that in case of free compounds, they can be obtained by saturating an aqueous solution of a hydrochloride salt compound with potassium carbonate, and after extracting the solution with chloroform, drying the extract over sodium sulfate and removing the solvent under reduced pressure.)

(As the starting amine compounds (a piperidine compound, a piperazine compound, etc.), those synthesized by the methods of Reference Examples 15-1 to 15-11 mentioned below, or known methods or combined methods thereof were used.)

Reference Example 12-97

(1) A mixture comprising 4.5 g of trans-4-(tert-butoxycarbonylamino)cyclohexanecarboxylic acid, 2.29 g of thiomorpholine, 3.90 g of 1-(3-dimethylaminopropyl)-3-ethylcarbodiimide, 2.74 g of 1-hydroxybenzotriazol and 30 ml of N,N-dimethylformamide was stirred at room temperature for 4 hours.

The reaction mixture was made basic by adding an aqueous sodium hydrogencarbonate solution, and extracted with ethyl acetate. The extract was washed with water and brine, dried over anhydrous sodium sulfate, and then, the solvent was removed under reduced pressure. The residue was suspended in diisopropyl ether and precipitates were collected by filtration to obtain N-tert-butoxycarbonyl-trans-4-(4-thiomorpholinylcarbonyl)cyclohexylamine.

(2) To 50 ml of a chloroform solution containing 5.4 g of the compound obtained in the above (1) was added 8.9 g of 75%-m-chloroperbenzoic acid under ice-cooling, and the mixture was stirred at room temperature for 1 hour. The reaction mixture was made basic by adding an aqueous sodium hydrogencarbonate solution, and extracted with ethyl acetate. The extract was washed with water and brine, dried over sodium sulfate, and then, the solvent was removed under reduced pressure. The residue was suspended in diisopropyl ether, and precipitates were collected by filtration.

Then, this compound was suspended in 25 mL of dioxane, 4N hydrochloric acid-dioxane solution (25 mL) was added thereto, and the mixture was stirred for 16 hours. Ether was added to the reaction mixture and precipitates were collected by filtration and dissolved in water. The solution was made basic by adding potassium carbonate, and extracted with chloroform. After the extract was dried over anhydrous sodium sulfate, the solvent was removed under reduced pressure. The residue was suspended in diisopropyl ether and precipitates were collected by filtration to obtain trans-4-(1,1-dioxo-4-thiomorpholinylcarbonyl)cyclohexylamine (Reference Example 12-97 in Table 8).

Reference Examples 13-1 to 13-7

To 50 ml of a methylene chloride suspension containing 5.07 g of trans-4-(benzyloxycarbonylamino)cyclohexanecarboxylic acid were added 4.0 ml of thionyl chloride and 0.3 ml of N,N-dimethylformamide and the mixture was stirred at room temperature for 1 hour.

The reaction mixture was concentrated under reduced pressure and 500 mg of the residual solid was added to 8 ml of an ice-cold methylene chloride solution containing 207 mg of 2-aminopyrimidine and 0.4 ml of triethylamine. After stirring at room temperature for 2 hours, water was added to the reaction mixture and the mixture was extracted with chloroform. The extract was concentrated under reduced pressure, and the resulting residue was purified by silica gel column chromatography (solvent: chloroform-methanol (50:1)) to obtain 240 mg of N-benzyloxycarbonyl-trans-4-[(pyrimidin-2-ylamino)carbonyl]cyclohexylamine.

This compound was applied to deprotection treatment to obtain trans-4-[(pyrimidin-2-ylamino)carbonyl]cyclohexylamine (Reference Example 13-1 in Table 8).

Also, the compounds of Reference Examples 13-2 to 13-7 in Table 8 were obtained in the same manner as mentioned above by using the corresponding starting materials instead of 2-aminopyrimidine.

The deprotection was carried out as mentioned below by using hydrogen bromide-acetic acid. That is, the compound was stirred in 3 ml of 30% hydrogen bromide-acetic acid solution at 50° C. for 4 hours. 30 ml of diisopropyl ether was added to the reaction mixture and precipitates were collected by filtration to obtain a hydrobromide of the deprotected compound. This hydrobromide was made into a solution and the solution was saturated with potassium carbonate and extracted with chloroform to obtain a free form.

Provided that the deprotection of the compound of Reference Example 13-2 was carried out by using palladium-carbon as mentioned below. That is, to a methanol-tetrahydrofuran suspension of the compound were added 10% palladium-carbon catalyst and ammonium formate, and the mixture was refluxed. The insolubles were removed by filtration and the filtrate was concentrated under reduced pressure.

Reference Examples 13-8 to 13-16

Under argon atmosphere, a mixture comprising 1.0 g trans-4-(benzyloxycarbonylamino)cyclohexanecarbonyl chloride, 1.92 g of tributylphenyltin, 61 mg of dichlorobis-(triphenylphosphine)palladium and 10 mL of dioxane was stirred at 110° C. for 12 hours. After cooling, the reaction mixture was concentrated by a centrifugal concentrator, and then, the residue was dissolved in tetrahydrofuran and evaporated to dryness with 5 g of silica gel. The resulting residue was purified by silica gel flash chromatography (solvent: ethyl acetate-hexane (1:2) to (1:1) to obtain 883 mg of N-benzyloxycarbonyl-trans-4-benzoylcylohexylamine.

870 mg of this compound was stirred with 1.0 g of trimethylsilyl iodide and 5 mL of chloroform under argon atmosphere at room temperature for 2 hours. Disappearance of the starting material was confirmed by TLC, 0.17 mL of methanol and 5 mL of diethyl ether were added to the reaction mixture and the mixture was stirred at room temperature for 3 days. The resulting precipitates were collected by filtration, washed with anhydrous diethyl ether, and dried to obtain 830 mg of trans-4-benzoylcyclohexylamine (Reference Example 13-8 in Table 8).

Also, the compounds of Reference Examples 13-9 to 13-16 in Table 8 were obtained in the same manner as mentioned above.

Reference Example 13-17

(1) trans-4-Methoxycarbonylcyclohexane-1-carbonyl chloride was obtained from 5 g of trans-4-methoxycarbonylcyclohxane-1-carboxylic acid and oxalyl chloride. 7.58 g of morpholine was added dropwise to 50 mL of a methylene chloride solution thereof under ice-cooling, and the mixture was stirred for 2 hours. The reaction mixture was poured into an aqueous 10% citric acid solution, extracted with chloroform, dried over anhydrous magnesium sulfate, and then, the solvent was removed under reduced pressure. The residue was purified by silica gel flash column chromatography (solvent: ethyl acetate-hexane (1:1) to ethyl acetate-chloroform (1:1)) and crystallized from hexane to obtain 6.49 g of trans-1-methoxycarbonyl-4-(morpholinocarbonyl)cyclohexane.

(2) Under argon atmosphere, 10 mL of a tetrahydrofuran solution containing 2.0 g of the compound obtained in the above (1) was added dropwise to 40 mL of a hexane-tetrahydrofuran (3:5) solution containing LDA (lithium diisopropylamide) (0.024 mol) prepared at the time of using at −78° C. and the temperature of the mixture was elevated to −30° C. over 2 hours, while stirring. The reaction mixture was cooled again to −78° C., reacted with 1.46 mL of methyl iodide, and allowed to stand to 0° C., and then, water was added thereto and the mixture was extracted with ethyl acetate. The extract was successively washed with an aqueous 10% citric acid solution, water and brine, dried over anhydrous sodium sulfate, and then, the solvent was removed under reduced pressure. The residue was purified by silica gel flash column chromatography (solvent: ethyl acetate-hexane (1:2) to (1:1)) to obtain 1.47 g of isomeric mixture of 1-methoxycarbonyl-1-methyl-4-(morpholinocarbonyl)cyclohexane. This mixture was stirred in a mixture comprising 158 mg of sodium hydroxide, 1 mL of ethanol and 1 mL of water at room temperature for 12 hours. The reaction mixture was extracted with diethyl ether, the extract was washed with water, dried over anhydrous sodium sulfate, and then, the solvent was removed under reduced pressure. The residue was recrystallized from a mixed solvent comprising diethyl ether-hexane to obtain 592 mg of single isomer of 1-methoxycarbonyl-1-methyl-4-(morpholinecarbonyl)cyclohexane.

(3) 546 mg of the compound (single isomer) obtained in the above (2) was stirred in a mixture comprising 251 mg of sodium hydroxide, 5 mL of methanol and 10 mL of water at 110° C. for 2 hours. After cooling, pH of the reaction mixture was adjusted to 3 by 10% hydrochloric acid, extracted three times with chloroform, the extract was dried over anhydrous magnesium sulfate, and then, the solvent was removed under reduced pressure. 5 mL of a toluene solution containing 479 mg of the resulting compound (carboxylic acid), 550 mg of diphenylphosphoryl azide and 216 mg of benzyl alcohol was stirred under heating for 12 hours. After cooling, an aqueous 10% citric acid solution was added to the reaction mixture, and the toluene layer was separated, washed with brine and dried over anhydrous sodium sulfate, and then, the solvent was removed under reduced pressure. The resulting residue was purified by silica gel flash chromatography (solvent: ethyl acetate-hexane (1:2)) to (1:1) to obtain 387 mg of N-benzyloxycarbonyl-1-methyl-4-(morpholinocarbonyl)cyclohexylamine.

This compound was deprotected by treating with trimethylsilyl iodide to obtain 1-methyl-4-(morpholinocarbonyl)cyclohexylamine (Reference Example 13-17 in Table 8).

Reference Examples 13-18 to 13-21

N-tert-butoxycarobonyl-trans-4-(1-piperazinylcarbonyl)cyclohexylamine was obtained by treating trans-4-(tert-butoxycarbonylamino)cyclohexanecarboxylic acid and piperazine in the same manner as in the above-mentioned Reference Example 11-1.

Methyl chlorocarbonate was added dropwise to a mixture comprising 400 mg of this compound, 260 mg of triethylamine and 8 mL of methylene chloride-under ice-cooling, and the mixture was stirred at room temperature overnight. The reaction mixture was successively washed with water and brine, dried over anhydrous sodium sulfate, and concentrated under reduced pressure. The resulting residue was suspended in diisopropyl ether and precipitates were collected by filtration to obtain 410 mg N-tert-butoxycarbonyl-trans-4-(4-methoxycarbonyl-1-piperazinylcarbonyl)cyclohexylamine.

This compound was deprotected under acidic conditions according to the conventional method and the acidic mixture was returned to basic to obtain trans-4-(4-methoxycarbonyl-1-piperazinylcarbonyl)cyclohexylamine (Reference Example 13-18 of Table 8).

Also, the compounds of Reference Examples 13-19 to 13-21 in Table 8 were obtained in the same manner as mentioned above.

Reference Example 13-22

A mixture comprising 623 mg of N-tert-butoxycarbonyl-trans-4-(piperazinocarbonyl)cyclohexylamine, 340 mg of 3,4-diethoxy-3-cyclobuten-1,2-dione and 5 ml of ethanol was stirred at room temperature for 2.5 days. The reaction mixture was concentrated under reduced pressure, and the resulting residue was purified by silica gel column chromatography (solvent: chloroform-methanol (50:1)) and subsequently triturated with ether.

This compound was deprotected by treating with hydrochloric acid-dioxane to obtain trans-4-[4-(4-ethoxy-1,2-dioxo-3-cyclobuten-3-yl)piperazinylcarbonyl]cyclohexylamine (Reference Example 13-22 in Table 8).

Reference Example 13-23

(1) A mixture comprising 1101 mg of N-benzyloxycarbonylpiperazine, 1131 mg of 3,4-dibutoxy-3-cyclobutene-1,2-dione and 5 ml of ethanol was stirred at room temperature for 25 hours. The reaction mixture was concentrated under reduced pressure, and the resulting residue was purified by silica gel column chromatography (solvent: chloroform-ethyl acetate (19:1)) to obtain 1570 mg of 1-benzyloxycarbonyl-4-(4-butoxy-1,2-dioxo-3-cyclobuten-3-yl)-piperazine.

This compound was deprotected by treating with palladium-carbon in the presence of 3 ml of 10% hydrochloric acid under hydrogen atmosphere to obtain 4-(4-butoxy-1,2-dioxo-3-cyclobuten-3-yl)-piperazine.

(2) The compound obtained in the above (1) was reacted with trans-(4-benzyloxycarbonylamino)cyclohexanecarbonyl chloride in methylene chloride in the presence of triethylamine to obtain N-benzyloxycarbonyl-trans-4-[4-(4-butoxy-1,2-dioxo-3-cyclobuten-3-yl)piperazinocarbonyl]cyclohexylamine.

(3) The compound obtained in the above (2) and dimethylamine hydrochloride were reacted in ethanol in the presence of triethylamine to obtain N-benzyloxycarbonyl-trans-4-[4-(4-dimethylamino-1,2-dioxo-3-cyclobuten-3-yl)piperazinylcarbonyl]cyclohexylamine. This compound was deprotected by treating with trimethylsilyl iodide to obtain trans-4-[4-(4-dimethylamino-1,2-dioxo-3-cyclobuten-3-yl)piperazinylcarbonyl]cyclohexylamine (Reference Example 13-23 in Table 8).

Reference Example 13-24

0.15 ml of triethylamine and 0.07 ml of methanesulfonyl chloride were added to 10 ml of a tetrahydrofuranmethylene chloride suspension containing 0.31 g of N-benzyloxycarbonyl-trans-4-[(5-hydroxylmethyl-2-isoindolinyl)carbonyl]cyclohexylamine under ice-cooling, and the mixture was stirred under ice-cooling for 1 hour. Water was added to the reaction mixture and the mixture was extracted with ethyl acetate. After the extract was dried over sodium sulfate, the solvent was removed under reduced pressure. To the residue were added 5 ml of dimethylformamide and 0.25 ml of morpholine, and the mixture was stirred at room temperature overnight. Water was added to the reaction mixture and the mixture was extracted with ethyl acetate. After the extract was dried over anhydrous sodium sulfate, the solvent was removed under reduced pressure. The residue was purified by silica gel chromatography (solvent: chloroform-methanol=100:1). This compound was treated with palladium-carbon under hydrogen atmosphere to obtain trans-4-[(5-morpholinomethyl-2-isoindolinyl)carbonyl]cyclohexylamine (Reference Example 13-24 in Table 8).

Reference Examples 13-25 to 13-29

(1) 20 g of manganese dioxide was added to 120 ml of a chloroform solution containing 4.0 g of N-benzyloxycarbonyl-trans-4-[(5-hydroxymethyl-2-isoindolinyl)carbonyl]cyclohexylamine, and the mixture was stirred at room temperature for 4 hours. Manganese dioxide was removed by filtration through Celite and the solvent was removed under reduced pressure. The residue was suspended in hexane-ethyl acetate and the crystals were collected by filtration to obtain N-benzyloxycarbonyl-trans-4-[(5-formyl-2-isoindolinyl)carbonyl]cyclohexylamine.

(2) To an aqueous solution containing 3.35 g of silver nitrate were added 2.75 g of the compound obtained in the above (1) and 110 ml of ethanol under ice-cooling, and then, an aqueous solution containing 2.61 g of potassium hydroxide was added dropwise thereto. The mixture was stirred under ice-cooling for 1 hour and separated by filtration through Celite, and then, the solvent was removed under reduced pressure. To the residue was added 50 ml of an aqueous 1N hydrochloric acid solution and the mixture was extracted with chloroform. After the extract was dried over anhydrous sodium sulfate, the solvent was removed under reduced pressure. The residue was suspended in hexane-ether and the crystals were collected by filtration to obtain N-benzyloxycarbonyl-trans-4-[(5-carboxy-2-isoindolinyl)carbonyl]cyclohexylamine.

(3) The compound obtained in the above (2) was used and condensed with a starting amine compound in the same manner as in Reference Example 11-1, and subsequently treated with palladium-carbon under hydrogen atmosphere to obtain trans-4-[(5-dimethylaminocarbonyl-2-isoindolinyl)carbonyl]cyclohexylamine (Reference 13-25 in Table 8).

Also, the compounds of Reference Examples 13-26 to 13-29 in Table 8 were obtained in the same manner as mentioned above.

Reference Examples 13-30 to 13-33

(1) 2.6 g of tert-butylcarbamate, 3.5 ml of triethylsilane and 1.15 ml of trifluoroacetic acid were added to 25 ml of an acetonitrile suspension containing 3.0 g of N-benzyloxycarbonyl-trans-4-[(5-formyl-2-isoindolinyl)carbonyl]cyclohexylamine (the compound obtained in Reference Example 13-25 (1)), and the mixture was stirred at room temperature overnight. Water was added to the reaction mixture and the mixture was extracted with chloroform. After the extract was dried over anhydrous sodium sulfate, the solvent was removed under reduced pressure. The residue was suspended in hexane-ethyl acetate and the crystals were collected by filtration to obtain N-benzyloxycarbonyl-trans-4-[(5-tert-butoxycarbonylaminomethyl-2-isoindolinyl)carbonyl]cyclohexylamine.

(2) The compound obtained in the above (1) was treated with palladium-carbon under hydrogen atmosphere to obtain trans-4-[(5-tert-butoxycarbonylaminomethyl-2-isoindolinyl)carbonyl]cyclohexylamine (Reference Example 13-30 in Table 8).

(3) The compound obtained in the above (1) was treated with 4N hydrochloric acid-dioxane to obtain N-benzyloxycarbonyl-trans-4-[(5-aminomethyl-2-isoindolinyl)carbonyl]cyclohexylamine hydrochloride.

(4) 0.25 ml of cyclopropanecarbonyl chloride was added to 5 ml of a methylene chloride-pyridine solution containing 0.5 g of the compound (hydrochloride) obtained in the above (3), and the mixture was stirred at room temperature for 4 hours. Diluted aqueous hydrochloric acid solution was added to the reaction mixture and the mixture was extracted with chloroform. After the extract was dried over anhydrous sodium sulfate, the solvent was removed under reduced pressure. The residue was purified by silica gel chromatography (solvent: chloroform-methanol=50:1) to obtain crystals. This compound was treated with palladium-carbon under hydrogen atmosphere to obtain trans-4-[(5-cyclopropylcarbonylaminomethyl-2-isoindolinyl)carbonyl]cyclohexylamine (Reference Example 13-31 in Table 8).

Also, the compounds of Reference Examples 13-32 to 13-33 in Table 8 were obtained in the same manner as mentioned above.

Reference Example 13-34

(1) 0.08 g of hydroxylamine hydrochloride and 0.09 g of sodium formate were added to 3 ml of a formic acid solution containing 0.3 g of N-benzyloxycarbonyl-trans-4-[(5-formyl-2-isoindolinyl)carbonyl]cyclohexylamine (the compound obtained in Reference Example 13-25 (1)), and the mixture was refluxed for 3 hours. Water was added to the reaction mixture and the mixture was extracted with ethyl acetate. After the extract was dried over anhydrous sodium sulfate, the solvent was removed under reduced pressure. The residue was purified by NH silica gel chromatography (solvent:chloroform-ethyl acetate=50:1), and the resulting compound was treated with trimethylsilyl iodide to obtain trans-4-[(5-cyano-2-isoindolinyl)carbonyl]cyclohexylamine hydroiodide (Reference Example 13-34 in Table 8).

Reference Examples 13-35 to 13-46

(1) 17.33 g of stannous chloride was added to a hydrated ethanol (120 ml of ethanol+1.2 ml of water) suspension containing 6.08 g of N-benzyloxycarbonyl-trans-4-[(6-nitro-1-indolinyl)carbonyl]cyclohexylamine (the compound obtained in the same manner as in Reference Example 13-1 before deprotection), and the mixture was refluxed under argon atmosphere for 4.5 hours. An aqueous 10% sodium hydroxide solution was added to the reaction mixture to adjust pH of the mixture to pH 9 to 10, the mixture was diluted with 300 ml of chloroform and dried over anhydrous magnesium sulfate, and then, the insolubles were removed by filtration. The filtrate was concentrated under reduced pressure, and the resulting residue was purified by silica gel column chromatography (solvent: chloroform-ethyl acetate (2:1)) to obtain 4.72 g of N-benzyloxycarbonyl-trans-4-[(6-amino-1-indolinyl)carbonyl]cyclohexylamine.

(2) 0.12 ml of pyridine and 0.104 ml of acetic anhydride were added to 10 ml of a methylene chloride solution containing 396 mg of the compound obtained in the above (1), and the mixture was stirred for 5 hours. 5% hydrochloric acid was added to the reaction mixture and the mixture was extracted with chloroform. The extracted layer was successively washed with water and an aqueous saturated sodium bicarbonate solution and dried over anhydrous sodium sulfate, and then, the solvent was removed under reduced pressure. The residue was purified by silica gel column chromatography (solvent: chloroform-ethyl acetate (1:1)).

This compound was deprotected by treating with palladium-carbon to obtain trans-4-[(6-acetylamino-1-indolinyl) carbonyl]cyclohexylamine (Reference Example 13-35 in Table 8).

Also, the compounds of Reference Examples 13-36 to 13-37 in Table 8 were obtained in the same manner as mentioned above.

(3) 0.085 ml of methanesulfonyl chloride was added to 10 ml of a pyridine solution containing 400 mg of the compound obtained in the above (1) at room temperature, and the mixture was stirred for 5 hours. The reaction mixture was concentrated under reduced pressure, the residue was dissolved in chloroform, washed successively with 5% hydrochloric acid, water and an aqueous saturated sodium bicarbonate solution and dried over anhydrous sodium sulfate, and then, the solvent was removed under reduced pressure. The residue was purified by silica gel column chromatography (solvent: chloroform-ethyl acetate (2:1)).

This compound was deprotected by treating with palladium-carbon to obtain trans-4-[(6-methylsulfonylamino-1-indolinyl)carbonyl]cyclohexylamine (Reference Example 13-38 in Table 8).

(4) 15 ml of N,N-dimethylformamide solution containing 403 mg of the compound obtained in the above (1), 169 mg of N,N-dimethylglycine hydrochloride, 243 mg of 1-ethyl-3-(3-dimethylaminopropyl)-carbodiimide hydrochloride, 173 mg of 1-hydroxybenzotriazole and 0.181 ml of triethylamine in was stirred at room temperature for 5 hours. The reaction mixture was concentrated under reduced pressure, the residue was dissolved in ethyl acetate, successively washed with an aqueous saturated sodium bicarbonate solution, water and brine, dried over anhydrous sodium sulfate, and then, the solvent was removed under reduced pressure. The residue was purified by silica gel column chromatography (solvent:chloroform-methanol (50:1)).

This compound was deprotected by treating with palladium-carbon to obtain trans-4-{[6-(dimethylamino)methyl-carbonyl-1-indolinyl]carbonyl}cyclohexylamine (Reference Example 13-39 in Table 8).

(5) 0.8 ml of an aqueous 37% formalin solution and 635 mg of sodium triacetoxyborohydride were added to 10 ml of an acetonitrile suspension containing 402 mg of the compound obtained in the above (1) at room temperature, and the mixture was stirred for 1.5 hours. The reaction mixture was diluted with water and extracted with ethyl acetate. The extracted layer was washed with water and brine in order, dried over anhydrous sodium sulfate, and then, the solvent was-removed under reduced pressure. The residue was purified by silica gel column chromatography (solvent:chloroform-ethyl acetate (2:1)).

This compound was deprotected by treating with palladium-carbon to obtain trans-4-[(6-dimethylamino-1-indolinyl)carbonyl]cyclohexylamine (Reference Example 13-40 in Table 8).

(6) The compounds of Reference Examples 13-41 to 13-46 were obtained in the same manner as in the above (1) to (5) except for using N-benzyloxycarbonyl-trans-4-[(5-nitro-1-indolinyl)carbonyl]cyclohexylamine (the compound obtained in the same manner as in Reference Example 13-1) as a starting material.

Reference Examples 13-47 to 13-52

451 mg of potassium carbonate and 238 mg of 2-(dimethylamino)ethyl chloride hydrochloride were added to 5 ml of a N,N-dimethylformamide solution containing 400 mg of N-benzyloxycarbonyl-trans-4-[(5-hydroxy-1-indolinyl)carbonyl]cyclohexylamine (the compound obtained in the same manner as in Reference Example 13-1), and the mixture was stirred at 50° C. for 19 hours. The reaction mixture was concentrated under reduced pressure, and a solution of the residue in chloroform was washed with water, dried over sodium sulfate, and then, the solvent was removed under reduced pressure. The residue was purified by silica gel column chromatography (solvent: chloroform-methanol (30:1)).

100 mg of 10% palladium-carbon catalyst and 920 mg of ammonium formate were added to 10 ml of methanol-10 ml of tetrahydrofuran suspension containing this compound, and the mixture was refluxed for 17 hours. The insolubles were removed by filtration, and the filtrate was concentrated under reduced pressure to obtain 281 mg of trans-4-{[5-(2- dimethylaminoethyl)oxy-1-indolinyl]carbonyl}cyclohexylamine (Reference Example 13-47 in Table 8).

Also, the compounds of Reference Examples 13-48 to 13-52 in Table 8 were obtained in the same manner as mentioned above.

Reference Examples 14-1 to 14-16

A mixture comprising 400 mg of cis-4-(tert-butoxycarbonylamino)cyclohexanecarboxylic acid, 216 mg of 4-hydroxypiperidine, 244 mg of 1-hydroxybenzotriazole, 686 mg of O-benzotriazol-1-yl-N,N,N',N'-tetramethyluroniumhexafluorophosphate, 398 µl of N-methylmorpholine and 11 ml of N,N-dimethylformamide was stirred at room temperature for 14 hours. Water was added to the reaction mixture and the mixture was extracted with ethyl acetate. The extract was washed with an aqueous 10% citric acid solution, water and brine, dried over anhydrous sodium sulfate, and then, the solvent was removed under reduced pressure. The resulting residue was dissolved in 5 ml of dioxane, then, 6 ml of 4N hydrochloric acid-dioxane was added thereto, and the mixture was stirred at room temperature for 12 hours. The reaction mixture was concentrated, methanol was added to the residue and the mixture was concentrated under reduced pressure. Next, ether was added to the residue, and the mixture was concentrated under reduced pressure to obtain cis-4-(4-hydroxypiperidinocarbonyl)cyclohexylamine•hydrochloride (Reference Example 14-1 in Table 8).

Also, the compounds of Examples 14-2 to 14-16 in Table 8 were obtained in the same manner as mentioned above, sing the corresponding starting materials. (Provided that in case of free compounds, they can be obtained by saturating an aqueous solution of a hydrochloride salt compound with potassium carbonate, and after extracting the solution with chloroform, drying the extract over anhydrous sodium sulfate and removing the solvent under reduced pressure.)

Reference Example 15-1

To a dimethylformamide (7 ml) solution containing N-(tert-butoxycarbonyl)piperazine (1.0 g) were added potassium carbonate (742 mg) and then butyl iodide (1.09 g), and the mixture was stirred at room temperature for 15 hours to undergo reaction, thereby obtaining N-tert-butoxycarbonyl-N-butylpiperazine. This compound was acid-treated with hydrochloric acid to obtain N-butylpiperazine•dihydrochloride.

Also, N-isopropylpiperazine•dihydrochloride was obtained in the same manner as mentioned above.

Reference Example 15-2

Dimethylamine hydrochloride (430 mg) was added to a methylene chloride (10 ml) solution containing 4-(tert-butoxycarbonyl)piperidone (1.0 g), and under ice-cooling, triethylamine (0.84 ml) and triacetoxyborohydride (1.17 g) were further added thereto, and the mixture was stirred at room temperature for 3 hours to undergo reaction, thereby obtaining N-tert-butoxycarbonyl-4-dimethylaminopiperidine. This compound was acid-treated with hydrochloric acid to obtain 4-(dimethylamino)piperidine-dihydrochloride.

Reference Example 15-3

Sodium triacetoxyborohydride (10.51 g) was added to a methylene chloride (50 ml) solution containing N-formylpiperazine (5.08 g) and cyclohexanecarboxaldehyde (7.50 g) under ice-cooling, and the mixture was stirred at room temperature for 18 hours to undergo reaction, thereby obtaining 1-formyl-4-cyclohexylmethylpiperazine, which was then acid-treated with hydrochloric acid to obtain 1-(cyclohexylmethyl)piperazine-hydrochloride.

Reference Example 15-4

60% Sodium hydride (0.232 g) was gradually added to a tetrahydrofuran (4.5 ml) solution containing 1-tert-butoxycarbonyl-4-hydroxypiperidine (0.900 g) and 2-chloropyrimidine (0.666 g), and 2 hours later, dimethyl sulfoxide (1.0 ml) was added thereto, and the mixture was stirred at room temperature for 1 day to undergo reaction, thereby obtaining 1-tert-butoxycarbonyl-4-(2-pyrimidinyloxy)piperidine. This compound was acid-treated with hydrochloric acid to obtain 4-(2-pyrimidinyloxy)piperidine•hydrochloride.

Also, the following compounds were obtained in the same manner as mentioned above. 4-(5-Cyano-2-pyridyloxy)piperidine•hydrochloride 4-(5-Bromo-2-pyrimidinyloxy)piperidine•hydrochloride 4-(p-Nitrophenoxy)piperidine-hydrochloride Reference Example 0.15-5

A mixture comprising N-(tert-butoxycarbonyl)piperidine-4-carboxylic acid (700 mg), morpholine (319 µL), 1-ethyl-3-(3-dimethylaminopropyl)-carbodiimide (702 mg), 1-hydroxybenzotriazole (495 mg) and N,N-dimethylformamide (9 ml) was stirred at room temperature for 16 hours to undergo reaction, and the resulting compound was acid-treated with hydrochloric acid to obtain 4-(morpholinocarbonyl)piperidine•hydrochloride.

Also, the following compounds were obtained in the same manner as mentioned above.
4-(Diethylaminocarbonyl)piperidine•hydrochloride
4-(N-methyl-N-benzylaminocarbonyl)piperidine•hydrochloride
4-(p-Chlorophenylaminocarbonyl)piperidine-hydrochloride Reference Example 15-6

A mixture comprising 4-amino-1-(tert-butoxycarbonyl)piperidine (700 mg), benzoic acid (512 mg), 1-ethyl-3-(3-dimethylaminopropyl)-carbodiimide (804 mg), 1-hydroxybenzotriazole (567 mg) and N,N-dimethylformamide (10 ml) was stirred at room temperature for 16 hours to undergo reaction, and the resulting compound was acid-treated with hydrochloric acid to obtain 4-(benzoylamino)piperidine•hydrochloride.

Also, the following compounds were obtained in the same manner as mentioned above.
4-(2-Pyridylcarbonylamino)piperidine•hydrochloride
4-(Cyclohexylcarbonylamino)piperidine•hydrochloride Reference Example 15-7

An acetonitrile (7 ml) solution containing N-(tert-butoxycarbonyl)piperazine (700 mg), N-methyl-N-phenylcarbamoyl chloride (700 mg) and triethylamine (1.05 mL) was stirred at room temperature for 15 hours to undergo reaction, and the resulting compound was acid-treated with hydrochloric acid to obtain 1-(N-methyl-N-phenylaminocarbonyl)piperazine hydrochloride.

Reference Example 15-8

Methanesulfonyl chloride (3.65 ml) was added to a methylene chloride (50 ml) solution containing N-formylpiperazine (5.08 g) and triethylamine (6.85 ml) under ice-cooling, and the mixture was stirred at room temperature for 18 hours to undergo reaction, thereby obtaining 1-formyl-4-methanesulfonylpiperazine. This compound was acid-treated with hydrochloric acid to obtain 1-methanesulfonylpiperazine•hydrochloride. Also, 1-(phenylsulfonyl)piperazine•hydrochloride was obtained in the same manner as mentioned above by using the corresponding starting material.

Reference Example 15-9

0.84 ml of triethylamine and 0.37 ml of methanesulfonyl chloride were added to 10 ml of a tetrahydrofuran solution containing 0.99 g of 2-tert-butoxycarbonyl-5-(hydroxylmethyl)isoindoline under ice-cooling, and the mixture was stirred under ice-cooling for 1 hour. Water was added to the reaction mixture and the mixture was extracted with ethyl acetate. After the extract was dried over sodium sulfate, the solvent was removed under reduced pressure. To the residue were added 20 ml of ethanol and 1.02 ml of diisopropylethylamine, and the mixture was refluxed for 30 minutes. The reaction mixture was concentrated under reduced pressure, and ethyl acetate and an aqueous 5% hydrochloric acid solution were added to the residue, followed by the extraction. After the extract was dried over sodium sulfate, the solvent was removed under reduced pressure. The residue was purified by silica gel chromatography (solvent: hexane-ethyl acetate=4:1) to obtain an oily product. This oily product was dissolved in 5 ml of dioxane, then, 8 ml of 4N hydrochloric acid-dioxane was added thereto, and the mixture was stirred at room temperature. The precipitates precipitated by addition of 20 ml of ether were collected by filtration and washed with ether to obtain 5-(ethoxymethyl)isoindoline-hydrochloride.

Also, the following compounds were obtained in the same manner as mentioned above.
5-(Methoxymethyl)isoindoline•hydrochloride
5-(Isopropyloxymethyl)isoindoline•hydrochloride Reference Example 15-10

0.85 ml of triethylamine and 0.35 ml of methyl chloroformate were added to 8 ml of a methylene chloride solution containing 0.72 g of 5-amino-2-tert-butoxycarbonylisoindoline, and the mixture was stirred at room temperature for 5 hours. Water was added to the reaction mixture and the mixture was extracted with ethyl acetate. After the extract was dried over anhydrous sodium sulfate, the solvent was removed under reduced pressure. The residue was purified by silica gel chromatography (solvent:chloroform-ethyl acetate=2:1) to obtain an oil. This oil was dissolved in 5 ml of dioxane, then, 8 ml of 4N hydrochloric acid-dioxane was added thereto, and the mixture was stirred at room temperature. The precipitates precipitated by addition of 20 ml of ether were collected by filtration and washed with ether to obtain 5-(methoxycarbonylamino)isoindoline.hydrochloride.

Also, the following compounds were obtained in the same manner as mentioned above. 5-(Acetylamino)isoindoline•hydrochloride Reference Example 15-11

2-tert-Butoxycarbonyl-5-aminoisoindoline (the compound obtained in the same manner as in WO 00/23428) and dimethylglycine were used as starting materials and reacted in the same manner as in Reference Example 11-1 to obtain 5-(dimethylaminomethylcarbonylamino)isoindoline.

In the following Table 1a to Table 1d and Table 2 to Table 8, chemical structures and physical properties of the compounds of the above Examples and Reference Examples are shown. (In Tables, "Me" represents a methyl group. Also, in Tables, MS APCI (m/z) represents mass spectrometric value (atmospheric pressure chemical ionization mass spectrum).)

TABLE 1a

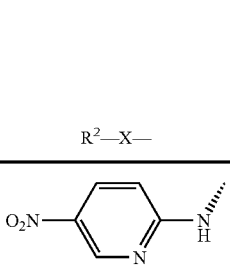

| Example No. | $R^2$—X— | $R^1$ | Salt | Physical properties, etc. |
|---|---|---|---|---|
| 1a-1 | 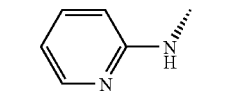 O$_2$N— (pyridyl) | H | 2HCl | Colorless powder MS · APCI (m/z): 373 [M + H]+ |
| 1a-2 | (pyridyl) | H | 2HCl | Brownish powder MS · APCI (m/z): 328 [M + H]+ |

TABLE 1a-continued

| Example No. | R²—X— | R¹ | Salt | Physical properties, etc. |
|---|---|---|---|---|
| 1a-3 | NC-pyridin-2-yl-NH- (5-CN) | H | HCl | Colorless powder<br>MS · APCI (m/z): 353 [M + H]+ |
| 1a-4 | 5-CF₃-pyridin-2-yl-NH- | H | 2HCl | Colorless powder<br>MS · APCI (m/z): 396 [M + H]+ |
| 1a-5 | 3-CN-pyridin-2-yl-NH- | H | 2HCl | Colorless powder<br>MS · APCI (m/z): 353 [M + H]+ |
| 1a-6 | 3-NO₂-pyridin-2-yl-NH- | H | 2HCl | Yellowish powder<br>MS · APCI (m/z): 373 [M + H]+ |
| 1a-7 | pyrimidin-2-yl-NH- | H | 2HCl | Colorless powder<br>MS · APCI (m/z): 329 [M + H]+ |
| 1a-8 | 5-Br-pyrimidin-2-yl-NH- | H | 2HCl | Colorless powder<br>MS · APCI (m/z): 407, 409 [M + H]+ |
| 1a-9 | 5-CH₃S-pyrimidin-2-yl-NH- | H | 2HCl | Pale yellowish powder<br>MS · APCI (m/z): 375 [M + H]+ |
| 1a-10 | 5-Cl-pyrimidin-2-yl-NH- | H | 2HCl | Colorless powder<br>MS · APCI (m/z): 363 [M + H]+ |
| 1a-11 | pyrimidin-2-yl-NH- | H | 2HCl | Colorless powder<br>MS · APCI (m/z): 329 [M + H]+ |
| 1a-12 | thiazol-2-yl-NH- | H | HCl | Pale brownish powder<br>MS · APCI (m/z): 334 [M + H]+ |
| 1a-13 | 4-O₂N-C₆H₄-NH- | H | HCl | Colorless powder<br>MS · APCI (m/z): 372 [M + H] |

TABLE 1a-continued

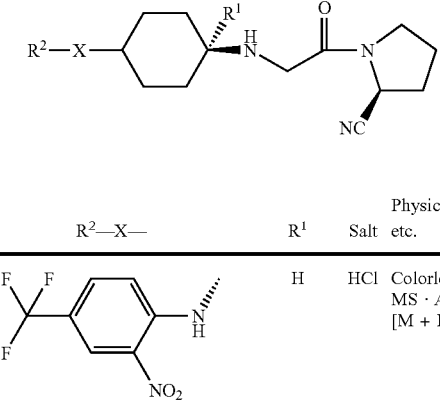

| Example No. | R²—X— | R¹ | Salt | Physical properties, etc. |
|---|---|---|---|---|
| 1a-14 | 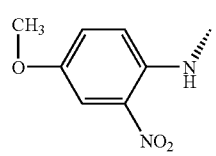 | H | HCl | Colorless powder<br>MS · APCI (m/z): 440 [M + H] |
| 1a-15 | 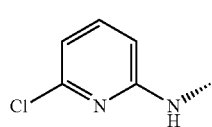 | H | HCl | Colorless powder<br>MS · APCI (m/z): 402 [M + H] |
| 1a-16 | 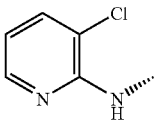 | H | 2HCl | Purified powder<br>MS · APCI (m/z): 364, 362 |
| 1a-17 | 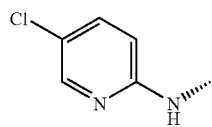 | H | 2HCl | Purified powder<br>MS · APCI (m/z): 364, 362 |
| 1a-18 | 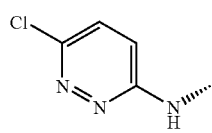 | H | 2HCl | Purified powder<br>MS · APCI (m/z): 364, 362 |
| 1a-19 | 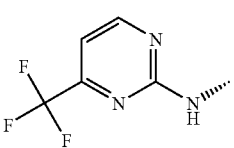 | H | 2HCl | Purified powder<br>MS · APCI (m/z): 365, 363 |
| 1a-20 | 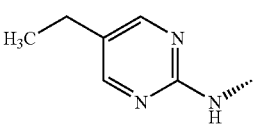 | H | 2HCl | Purified powder<br>MS · APCI (m/z): 397 |
| 1a-21 | 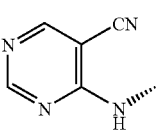 | H | 2HCl | Purified powder<br>MS · APCI (m/z): 357 |
| 1a-22 |  | H | 2HCl | Purified powder<br>MS · APCI (m/z): 354 |

TABLE 1a-continued

| Example No. | R²—X— | R¹ | Salt | Physical properties, etc. |
|---|---|---|---|---|
| 1a-23 | 3-cyanopyrazin-2-ylamino | H | 2HCl | Purified powder MS·APCI (m/z): 354 |
| 1a-24 | 2-amino-6-chloropyrimidin-4-ylamino | H | 2HCl | Colorless powder MS·APCI (m/z): 378 [M + H]+ |
| 1a-25 | pyridazin-3-ylamino | H | 2HCl | Purified powder MS·APCI (m/z): 329 |
| 1a-26 | 3-nitropyridin-2-ylamino N-oxide | H | HCl | Brownish powder MS·APCI (m/z): 389 [M + H] |
| 1a-27 | 2-methylthiopyrimidin-4-ylamino | H | 2HCl | Colorless powder MS·APCI (m/z): 375 [M + H]+ |
| 1a-28 | 5-ethoxycarbonyl-2-methylthiopyrimidin-4-ylamino | H | 2HCl | Colorless powder MS·APCI (m/z): 447 [M + H]+ |
| 1a-29 | 2-chloro-3-ethoxycarbonyl-6-methylpyridin-4-ylamino | H | 2HCl | Colorless powder MS·APCI (m/z): 448 [M + H]+ |

TABLE 1a-continued

| Example No. | R²—X— | R¹ | Salt | Physical properties, etc. |
|---|---|---|---|---|
| 1a-30 | 2-phenyl-pyrimidine-5-carboxylic acid ethyl ester | H | 2HCl | Colorless powder<br>MS · APCI (m/z): 477 [M + H]+ |
| 1a-31 | 2-(thiophen-2-yl)-pyrimidine-5-carboxylic acid ethyl ester | H | 2HCl | Colorless powder<br>MS · APCI (m/z): 483 [M + H]+ |
| 1a-32 | 2-morpholino-pyrimidine-5-carboxylic acid ethyl ester | H | 2HCl | Colorless powder<br>MS · APCI (m/z): 486 [M + H]+ |
| 1a-33 | 2-(dimethylamino)-pyrimidine-5-carboxylic acid ethyl ester | H | 2HCl | Colorless powder<br>MS · APCI (m/z): 444 [M + H]+ |

TABLE 1a-continued

| Example No. | R²—X— | R¹ | Salt | Physical properties, etc. |
|---|---|---|---|---|
| 1a-34 | (pyrrolidine-pyrimidine with ethyl ester) | H | 2HCl | Colorless powder MS · APCI (m/z): 470 [M + H]+ |
| 1a-35 | (morpholine-pyrimidine with N,N-dimethylamide) | H | 2HCl | Colorless powder MS · APCI (m/z): 485 [M + H]+ |
| 1a-36 | (pyrrolidine-pyrimidine with morpholine amide) | H | 2HCl | Colorless powder MS · APCI (m/z): 511 [M + H]+ |
| 1a-37 | (dimethylamino-pyrimidine with morpholine amide) | H | 2HCl | Colorless powder MS · APCI (m/z): 485 [M + H]+ |

TABLE 1a-continued

| Example No. | R²—X— | R¹ | Salt | Physical properties, etc. |
|---|---|---|---|---|
| 1a-38 | (2-methylthio-4-amino-pyrimidin-5-yl)-morpholinyl ketone | H | 2HCl | Colorless powder MS · APCI (m/z): 488 [M + H]+ |
| 1a-39 | (2-methylthio-4-amino-pyrimidin-5-yl)-pyrrolidinyl ketone | H | 2HCl | Colorless powder MS · APCI (m/z): 472 [M + H]+ |
| 1a-40 | 2-methylthio-4-amino-pyrimidine-5-N,N-dimethylcarboxamide | H | 2HCl | Colorless powder MS · APCI (m/z): 446 [M + H]+ |
| 1a-41 | (2-phenyl-4-amino-pyrimidin-5-yl)-morpholinyl ketone | H | 2HCl | Colorless powder MS · APCI (m/z): 518 [M + H]+ |
| 1a-42 | 6-phenyl-pyridazin-3-ylamino | H | 2HCl | Purified powder MS · APCI (m/z): 405 |
| 1a-43 | 1-phenyl-1H-tetrazol-5-ylamino | H | 2HCl | Colorless powder MS · APCI (m/z): 395 [M + H]+ |

TABLE 1a-continued

| Example No. | R²—X— | R¹ | Salt | Physical properties, etc. |
|---|---|---|---|---|
| 1a-44 | 4-methyl-2-nitrophenyl-NH- | H | 2HCl | Purified powder MS·APCI (m/z): 386 |
| 1a-45 | 2-nitrophenyl-NH- | H | 2HCl | Purified powder MS·APCI (m/z): 372 |
| 1a-46 | 3-fluoro-2-cyanophenyl-NH- | H | 2HCl | Purified powder MS·APCI (m/z): 370 |
| 1a-47 | 4-fluoro-2-cyanophenyl-NH- | H | 2HCl | Purified powder MS·APCI (m/z): 370 |
| 1a-48 | 3-trifluoromethyl-2-cyanophenyl-NH- | H | 2HCl | Purified powder MS·APCI (m/z): 420 |
| 1a-49 | 3-amino-2-cyanophenyl-NH- | H | 3HCl | Purified powder MS·APCI (m/z): 367 |
| 1a-50 | 4-cyano-3-fluorophenyl-NH- | H | 2HCl | Purified powder MS·APCI (m/z): 370 |
| 1a-51 | 2-cyanophenyl-NH- | H | 2HCl | Colorless powder MS·APCI (m/z): 352 [M + H] |
| 1a-52 | 5-fluoro-2-cyanophenyl-NH- | H | 2HCl | Colorless powder MS·APCI (m/z): 370 [M + H] |

TABLE 1a-continued

[Structure: R²—X—[cyclohexyl with R¹ and NH]—CH₂—C(O)—N-pyrrolidine-CN]

| Example No. | R²—X— | R¹ | Salt | Physical properties, etc. |
|---|---|---|---|---|
| 1a-53 | 4-bromo-2-cyano-phenyl-NH— | H | 2HCl | Colorless powder MS·APCI (m/z): 432, 430 [M + H] |
| 1a-54 | 3-methoxy-2-cyano-phenyl-NH— | H | 2HCl | Colorless powder MS·APCI (m/z): 382 [M + H] |
| 1a-55 | benzothiazol-2-yl-NH— | H | 2HCl | Colorless powder MS·APCI (m/z): 384 [M + H]+ |
| 1a-56 | benzoxazol-2-yl-NH— | H | 2HCl | Colorless powder MS·APCI (m/z): 368 [M + H]+ |
| 1a-57 | 3-chloroquinoxalin-2-yl-NH— | H | 2HCl | Colorless powder MS·APCI (m/z): 413 [M + H]+ |
| 1a-58 | benzofuro[3,2-d]pyrimidin-4-yl-NH— | H | 2HCl | Colorless powder MS·APCI (m/z): 419 [M + H]+ |
| 1a-59 | 2-chloro-benzofuro[3,2-d]pyrimidin-4-yl-NH— | H | 2HCl | Colorless powder MS·APCI (m/z): 453 [M + H]+ |
| 1a-60 | 5-nitro-pyridin-2-yl-NH— | H | 2HCl | Colorless powder MS·APCI (m/z): 373 [M + H]+ |
| 1a-61 | 5-cyano-pyridin-2-yl-NH— | H | 2HCl | Colorless powder MS·APCI (m/z): 353 [M + H]+ |

TABLE 1a-continued

| Example No. | R²—X— | R¹ | Salt | Physical properties, etc. |
|---|---|---|---|---|
| 1a-62 | 3-cyano-pyridin-2-ylamino | H | 2HCl | Pale yellowish powder<br>MS·APCI (m/z): 353 [M + H]+ |
| 1a-63 | 3-nitro-pyridin-2-ylamino | H | 2HCl | Pale brownish powder<br>MS·APCI (m/z): 373 [M + H]+ |
| 1a-64 | pyrimidin-2-ylamino | H | 2HCl | Colorless powder<br>MS·APCI (m/z): 329 [M + H]+ |
| 1a-65 | 5-bromo-pyrimidin-2-ylamino | H | 2HCl | Pale yellowish powder<br>MS·APCI (m/z): 409 [M + H]+ |
| 1a-66 | 5-methylthio-pyrimidin-2-ylamino | H | 2HCl | Pale yellowish powder<br>MS·APCI (m/z): 375 [M + H]+ |
| 1a-67 | pyrimidin-2-ylamino | Me | 2HCl | Colorless powder<br>MS·APCI (m/z): 343 [M + H]+ |
| 1a-68 | 5-nitro-pyridin-2-ylamino | Me | 2HCl | Pale yellowish powder<br>MS·APCI (m/z): 387 [M + H]+ |
| 1a-69 | 3-nitro-pyridin-2-ylamino | Me | 2HCl | Yellowish powder<br>MS·APCI (m/z): 387 [M + H]+ |
| 1a-70 | 5-cyano-pyridin-2-ylamino | Me | 2HCl | Colorless powder<br>MS·APCI (m/z): 367 [M + H]+ |
| 1a-71 | 3-cyano-pyridin-2-ylamino | Me | 2HCl | Colorless powder<br>MS·APCI (m/z): 367 [M + H]+ |
| 1a-72 | pyrimidin-5-ylamino | Me | 2HCl | Brownish powder<br>MS·APCI (m/z): 343 [M + H]+ |

TABLE 1a-continued

| Example No. | R²—X— | R¹ | Salt | Physical properties, etc. |
|---|---|---|---|---|
| 1a-73 | O₂N-pyridin-2-yl-NH- (5-nitro) | Me | 2HCl | Pale yellowish powder MS·APCI (m/z): 387 [M + H]+ |
| 1a-74 | 3-NO₂-pyridin-2-yl-NH- | Me | 2HCl | Yellowish powder MS·APCI (m/z): 387 [M + H]+ |
| 1a-75 | NC-pyridin-2-yl-NH- (5-CN) | Me | 2HCl | Colorless powder MS·APCI (m/z): 367 [M + H]+ |
| 1a-76 | 3-CN-pyridin-2-yl-NH- | Me | 2HCl | Colorless powder MS·APCI (m/z): 367 [M + H]+ |
| 1a-77 | CH₃S-pyrimidin-2-yl-NH- | CH₂OH | 2HCl | Pale yellowish powder MS·APCI (m/z): 405 [M + H]+ |
| 1a-78 | 3-NO₂-pyridin-2-yl-NH- | CH₂OH | 2HCl | Pale yellowish powder MS·APCI (m/z): 403 [M + H]+ |
| 1a-79 | 3-CN-pyridin-2-yl-NH- | CH₂OH | 2HCl | Colorless powder MS·APCI (m/z): 383 [M + H]+ |
| 1a-80 | O₂N-pyridin-2-yl-NH- (5-nitro) | CH₂OH | 2HCl | Pale yellowish powder MS·APCI (m/z): 403 [M + H]+ |
| 1a-81 | NC-pyridin-2-yl-NH- (5-CN) | CH₂OH | 2HCl | Colorless powder MS·APCI (m/z): 383 [M + H]+ |
| 1a-82 | NC-pyridin-2-yl-NH- (5-CN) | CH₂OH | 2HCl | Colorless powder MS·APCI (m/z): 383 [M + H]+ |
| 1a-83 | 3-CN-pyridin-2-yl-NH- | CH₂OH | 2HCl | Pale yellowish powder MS·APCI (m/z): 383 [M + H]+ |

TABLE 1a-continued

R²—X—[cyclohexyl(R¹)]—NH—CH₂—C(O)—N[pyrrolidine-CN]

| Example No. | R²—X— | R¹ | Salt | Physical properties, etc. |
|---|---|---|---|---|
| 1a-84 | O₂N-pyridyl-NH- (5-nitro-2-pyridylamino) | CH₂OH | 2HCl | Pale yellowish powder MS · APCI (m/z): 403 [M + H]+ |
| 1a-85 | 3-nitro-2-pyridylamino | CH₂OH | 2HCl | Pale yellowish powder MS · APCI (m/z): 403 [M + H]+ |
| 1a-86 | pyrimidin-2-yl-N(CH₃)- | H | 2HCl | Purified powder MS · APCI (m/z): 343 [M + H]+ |
| 1a-87 | 5-Br-pyrimidin-2-yl-N(CH₃)- | H | 2HCl | Purified powder MS · APCI (m/z): 421 [M + H]+ |
| 1a-88 | pyrazin-2-yl-N(CH₃)- | H | 2HCl | Purified powder MS · APCI (m/z): 343 [M + H]+ |
| 1a-89 | 5-NC-pyridin-2-yl-N(CH₃)- | H | 2HCl | Purified powder MS · APCI (m/z): 367 [M + H]+ |

TABLE 1b

R²—X—[cyclohexyl(R¹)]—NH—CH₂—C(O)—N[pyrrolidine-CN]

| Example No. | R²—X— | R¹ | Salt | Physical properties, etc. |
|---|---|---|---|---|
| 1b-1 | 5-nitro-2-pyridyloxy | H | HCl | Colorless powder MS · APCI (m/z): 374 [M + H]+ |
| 1b-2 | 5-cyano-2-pyridyloxy | H | HCl | Colorless crystal Gradually decomposed around at melting point: 233° C. MS · APCI (m/z): 354 [M + H]+ |

TABLE 1b-continued

| Example No. | R²—X— | R¹ | Salt | Physical properties, etc. |
|---|---|---|---|---|
| 1b-3 | 5-(trifluoromethyl)pyridin-2-yloxy | H | HCl | Colorless powder<br>MS · APCI (m/z): 397 [M + H]+ |
| 1b-4 | 3-nitropyridin-2-yloxy | H | HCl | Pale yellowish powder<br>MS · APCI (m/z): 374 [M + H]+ |
| 1b-5 | 3-aminopyridin-2-yloxy | H | 2HCl | Colorless powder<br>MS · APCI (m/z): 344 [M + H]+ |
| 1b-6 | 5-bromopyrimidin-2-yloxy | H | HCl | Colorless powder<br>MS · APCI (m/z): 410 [M + H]+ |
| 1b-7 | 5-chloropyrimidin-2-yloxy | H | HCl<br>Free form | Colorless powder<br>MS · APCI (m/z): 364 [M + H]+<br>Colorless crystal<br>Melting point:<br>129–130° C. (decomposed) |
| 1b-8 | 5-(methylthio)pyrimidin-2-yloxy | H | HCl | Pale yellowish powder<br>MS · APCI (m/z): 376 [M + H]+ |
| 1b-9 | 5-methoxypyrimidin-2-yloxy | H | HCl | Colorless<br>MS · APCI (m/z): 360 [M + H]+ |
| 1b-10 | 5-(benzyloxy)pyrimidin-2-yloxy | H | HCl | Colorless powder<br>MS · APCI (m/z): 436 [M + H]+ |
| 1b-11 | 5-(furan-2-yl)pyrimidin-2-yloxy | H | HCl | Colorless powder<br>MS · APCI (m/z): 396 [M + H]+ |
| 1b-12 | pyrimidin-2-yloxy | H | HCl | Colorless powder<br>MS · APCI (m/z): 330 [M + H]+ |
| 1b-13 | 4-nitrophenoxy | H | HCl | Pale yellowish powder<br>MS · APCI (m/z): 373 [M + H]+ |

TABLE 1b-continued

| Example No. | R²—X— | R¹ | Salt | Physical properties, etc. |
|---|---|---|---|---|
| 1b-14 | pyrazin-2-yloxy | H | HCl | Purified powder<br>MS · APCI (m/z):<br>330 [M + H]+ |
| 1b-15 | 3-cyano-pyridin-2-yloxy | H | HCl | Purified powder<br>MS · APCI (m/z):<br>354 [M + H]+ |
| 1b-16 | 6-chloro-pyridin-2-yloxy | H | 2HCl | Purified powder<br>MS · APCI (m/z): 365, 363 |
| 1b-17 | 3-chloro-pyridin-2-yloxy | H | 2HCl | Purified powder<br>MS · APCI (m/z): 365, 363 |
| 1b-18 | 3-methoxy-pyridin-2-yloxy | H | 2HCl | Purified powder<br>MS · APCI (m/z): 359 |
| 1b-19 | pyridin-2-yloxy | H | 2HCl | Purified powder<br>MS · APCI (m/z): 329 |
| 1b-20 | 5-chloro-pyridin-2-yloxy | H | 2HCl | Purified powder<br>MS · APCI (m/z): 365, 363 |
| 1b-21 | 6-methoxy-pyridin-2-yloxy | H | 2HCl | Purified powder<br>MS · APCI (m/z): 359 |
| 1b-22 | pyrimidin-4-yloxy | H | HCl | Colorless powder<br>MS · APCI (m/z):<br>330 [M + H]+ |
| 1b-23 | 6-chloro-pyrazin-2-yloxy | H | HCl | Purified powder<br>MS · APCI (m/z):<br>366, 364 |
| 1b-24 | 3-cyano-pyrazin-2-yloxy | H | HCl | Purified powder<br>MS · APCI (m/z): 355 |

TABLE 1b-continued

| Example No. | R²—X— | R¹ | Salt | Physical properties, etc. |
|---|---|---|---|---|
| 1b-25 | H₃C—S-pyrimidin-4-yl-O- | H | HCl | Colorless powder MS·APCI (m/z): 376 [M + H]+ |
| 1b-26 | CF₃-pyrimidin-2-yl-O- | H | HCl | Purified powder MS·APCI (m/z): 398 |
| 1b-27 | H₃C-ethyl-pyrimidin-2-yl-O- | H | HCl | Purified powder MS·APCI (m/z): 358 |
| 1b-28 | 3-chloropyrazin-2-yl-O- | H | HCl | Purified powder MS·APCI (m/z): 366, 364 |
| 1b-29 | 6-chloropyridazin-3-yl-O- | H | HCl | Purified powder MS·APCI (m/z): 366, 364 |
| 1b-30 | pyridazin-3-yl-O- | H | HCl | Purified powder MS·APCI (m/z): 330 |
| 1b-31 | 3-(N,N-diisopropylcarbamoyl)pyridin-2-yl-O- | H | 2HCl | Purified powder MS·APCI (m/z): 456 |
| 1b-32 | 2-nitrophenyl-O- | H | HCl | Purified powder MS·APCI (m/z): 373 |
| 1b-33 | 2-cyanophenyl-O- | H | HCl | Colorless powder MS·APCI (m/z): 353 [M + H] |

TABLE 1b-continued

| Example No. | R²—X— | R¹ | Salt | Physical properties, etc. |
|---|---|---|---|---|
| 1b-34 | 3-fluoro-2-cyanophenoxy | H | HCl | Colorless powder<br>MS·APCI (m/z): 371 [M + H]+ |
| 1b-35 | 2-cyano-3-fluorophenoxy (CN top, F bottom) | H | HCl | Colorless powder<br>MS·APCI (m/z): 371 [M + H]+ |
| 1b-36 | 3-trifluoromethyl-2-cyanophenoxy | H | HCl | Colorless powder<br>MS·APCI (m/z): 421 [M + H]+ |
| 1b-37 | 4-cyano-3-fluorophenoxy | H | HCl | Colorless powder<br>MS·APCI (m/z): 371 [M + H]+ |
| 1b-38 | 2-cyano-5-fluorophenoxy | H | HCl | Colorless powder<br>MS·APCI (m/z): 371 [M + H]+ |
| 1b-39 | 2-cyano-5-methylphenoxy | H | HCl | Colorless powder<br>MS·APCI (m/z): 367 [M + H] |
| 1b-40 | 2-cyano-4-fluorophenoxy | H | HCl | Pale brownish powder<br>MS·APCI (m/z): 371 [M + H] |
| 1b-41 | 5-bromo-2-cyanophenoxy | H | HCl | Colorless powder<br>MS·APCI (m/z): 433, 431 [M + H] |
| 1b-42 | 2-cyano-3-methoxyphenoxy | H | HCl | Colorless powder<br>MS·APCI (m/z): 383 [M + H] |

TABLE 1b-continued

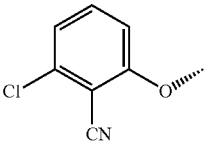

| Example No. | R²—X— | R¹ | Salt | Physical properties, etc. |
|---|---|---|---|---|
| 1b-43 | 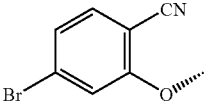 | H | HCl | Colorless powder<br>MS · APCI (m/z): 387 [M + H] |
| 1b-44 | 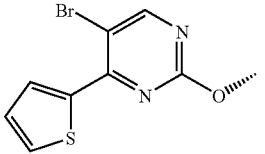 | H | HCl | Colorless powder<br>MS · APCI (m/z): 433, 431 [M + H] |
| 1b-45 | 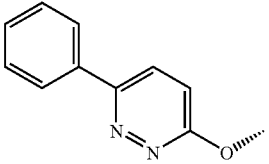 | H | HCl | Purified powder<br>MS · APCI (m/z): 492, 490 |
| 1b-46 | 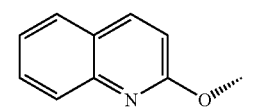 | H | HCl | Purified powder<br>MS · APCI (m/z): 406 |
| 1b-47 | 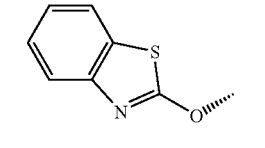 | H | HCl | Purified powder<br>MS · APCI (m/z): 379 |
| 1b-48 | 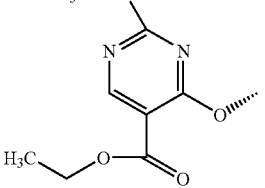 | H | HCl | Colorless powder<br>MS · APCI (m/z): 385 [M + H]+ |
| 1b-49 | 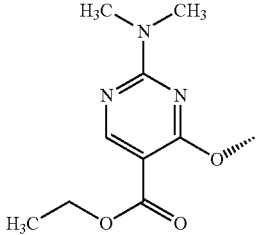 | H | HCl | Purified powder<br>MS · APCI (m/z): 448 |
| 1b-50 |  | H | 2HCl | Purified powder<br>MS · APCI (m/z): 445 |

TABLE 1b-continued

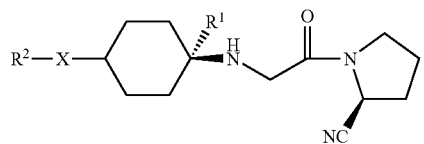

| Example No. | R²—X— | R¹ | Salt | Physical properties, etc. |
|---|---|---|---|---|
| 1b-51 | H₃C-NH-pyrimidine-4-O(methoxy)-5-C(=O)-O-CH₂CH₃ | H | 2HCl | Purified powder<br>MS · APCI (m/z): 431 |
| 1b-52 | morpholino-pyrimidine-4-O-5-C(=O)-O-CH₂CH₃ | H | 2HCl | Purified powder<br>MS · APCI (m/z): 487 |
| 1b-53 | pyrrolidinyl-pyrimidine-4-O-5-C(=O)-O-CH₂CH₃ | H | 2HCl | Purified powder<br>MS · APCI (m/z): 471 |
| 1b-54 | H₂N-pyrimidine-4-O-5-C(=O)-O-CH₂CH₃ | H | 2HCl | Purified powder<br>MS · APCI (m/z): 417 |
| 1b-55 | (H₃C)₂N-pyrimidine-4-O-5-C(=O)-N(CH₃)₂ | H | 2HCl | Purified powder<br>MS · APCI (m/z): 444 |

TABLE 1b-continued

| Example No. | R²—X— | R¹ | Salt | Physical properties, etc. |
|---|---|---|---|---|
| 1b-56 | (4-methoxy-2-(dimethylamino)pyrimidin-5-yl)(morpholino)methanone | H | 2HCl | Purified powder<br>MS · APCI (m/z): 486 |
| 1b-57 | (4-methoxy-2-(dimethylamino)pyrimidin-5-yl)(pyrrolidin-1-yl)methanone | H | 2HCl | Purified powder<br>MS · APCI (m/z): 470 |
| 1b-58 | 5-nitro-2-oxypyridine | H | HCl | Colorless powder<br>MS · APCI (m/z): 374<br>[M + H]+ |
| 1b-59 | 5-cyano-2-oxypyridine | H | HCl | Colorless powder<br>MS · APCI (m/z): 354<br>[M + H]+ |
| 1b-60 | 5-(trifluoromethyl)-2-oxypyridine | H | HCl | Colorless powder<br>MS · APCI (m/z): 397<br>[M + H]+ |
| 1b-61 | 3-cyano-2-oxypyridine | H | HCl | Colorless powder<br>MS · APCI (m/z): 354<br>[M + H]+ |
| 1b-62 | 5-bromo-2-oxypyrimidine | H | HCl | Colorless powder<br>MS · APCI (m/z): 408<br>[M + H]+ |
| 1b-63 | 5-(methylthio)-2-oxypyrimidine | H | HCl | Yellowish powder<br>MS · APCI (m/z): 376<br>[M + H]+ |
| 1b-64 | 2-oxypyrazine | H | HCl | Colorless powder<br>MS · APCI (m/z): 330<br>[M + H]+ |

TABLE 1b-continued

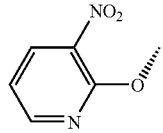

| Example No. | R²—X— | R¹ | Salt | Physical properties, etc. |
|---|---|---|---|---|
| 1b-65 | 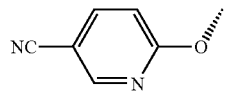 | Me | HCl | Purified powder<br>MS · APCI (m/z): 388 [M + H]+ |
| 1b-66 | 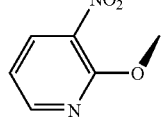 | Me | HCl | Purified powder<br>MS · APCI (m/z): 368 [M + H]+ |
| 1b-67 | 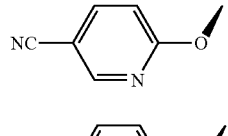 | Me | HCl | Purified powder<br>MS · APCI (m/z): 388 [M + H]+ |
| 1b-68 | 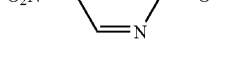 | Me | HCl | Purified powder<br>MS · APCI (m/z): 368 [M + H]+ |
| 1b-69 | 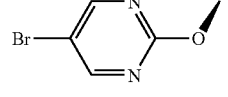 | Me | HCl | Purified powder<br>MS · APCI (m/z): 388 [M + H]+ |
| 1b-70 | 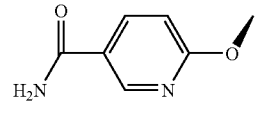 | Me | HCl | Purified powder<br>MS · APCI (m/z): 424 [M + H]+ |
| 1b-71 | 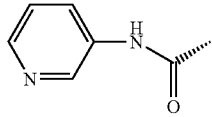 | Me | HCl | Purified powder<br>MS · APCI (m/z): 386 [M + H]+ |

TABLE 1c

| Example No. | R²—X— | R¹ | Salt | Physical properties, etc. |
|---|---|---|---|---|
| 1c-1 | | H | 2HCl | Colorless powder<br>MS · APCI (m/z): 356 [M + H]+ |

TABLE 1c-continued

| Example No. | R²—X— | R¹ | Salt | Physical properties, etc. |
|---|---|---|---|---|
| 1c-2 | cyclohexyl-NH-C(=O)-CH₂- | H | HCl | Colorless powder<br>MS · APCI (m/z): 361 [M + H] |
| 1c-3 | piperidin-1-yl-NH-C(=O)-CH₂- | H | HCl | Purified powder<br>MS · APCI (m/z): 362 |
| 1c-4 | phenyl-NH-C(=O)-CH₂- | H | HCl | Colorless powder<br>MS · APCI (m/z): 355 [M + H]+ |
| 1c-5 | cyclohexyl-N(CH₃)-C(=O)-CH₂- | H | HCl | Colorless powder<br>MS · APCI (m/z): 375 [M + H] |
| 1c-6 | benzyl-N(CH₃)-C(=O)-CH₂- | H | HCl | Colorless powder<br>MS · APCI (m/z): 383 [M + H]+ |
| 1c-7 | piperidin-1-yl-CH₂CH₂-N(CH₃)-C(=O)-CH₂- | H | 2HCl | Purified powder<br>MS · APCI (m/z): 404 |
| 1c-8 | (pyridin-2-yl)-CH₂CH₂-N(CH₃)-C(=O)-CH₂- | H | 2HCl | Colorless powder<br>MS · APCI (m/z): 398 [M + H] |
| 1c-9 | (1,3-benzodioxol-5-yl)-CH₂-N(CH₃)-C(=O)-CH₂- | H | HCl | Purified powder<br>MS · APCI (m/z): 427 |
| 1c-10 | (CH₃)₂N-C(=O)-CH₂- | H | HCl | Colorless crystal<br>Melting point: 211° C. (decomposed)<br>MS · APCI (m/z): 307 [M + H] |

TABLE 1c-continued

| Example No. | R²—X— | R¹ | Salt | Physical properties, etc. |
|---|---|---|---|---|
| 1c-11 | H₃C-CH₂-CH₂-N(CH₃)-C(=O)- | H | HCl | Purified powder<br>MS · APCI (m/z): 349 |
| 1c-12 | H₃C-(CH₂)₄-N(CH₃)-C(=O)- | H | HCl | Colorless powder<br>MS · APCI (m/z): 377 [M + H]+ |
| 1c-13 | (H₃C-CH₂)(H₃C-CH(CH₃))N-C(=O)- (isopropyl, ethyl on N) | H | HCl | Purified powder<br>MS · APCI (m/z): 349 |
| 1c-14 | (H₃C-CH₂-CH₂)₂N-C(=O)- | H | HCl | Colorless powder<br>MS · APCI (m/z): 363 [M + H]+ |
| 1c-15 | H₃C-O-CH₂-CH₂-N(CH₂CH₃)-C(=O)- | H | HCl | Purified powder<br>MS · APCI (m/z): 365 |
| 1c-16 | cyclohexyl-N(CH₂CH₃)-C(=O)- | H | HCl | Colorless powder<br>MS · APCI (m/z): 389 [M + H]+ |
| 1c-17 | H₂N-C(=O)- | H | HCl | Pale brownish purified resin state<br>MS · APCI (m/z): 279 [M + H]+ |
| 1c-18 | H₃C-NH-C(=O)- | H | HCl | Purified powder<br>MS · APCI (m/z): 293 [M + H]+ |
| 1c-19 | H₃C-CH₂-NH-C(=O)- | H | HCl | Purified powder<br>MS · APCI (m/z): 307 [M + H]+ |
| 1c-20 | H₃C-(CH₂)₃-NH-C(=O)- | H | HCl | Purified powder<br>MS · APCI (m/z): 335 [M + H]+ |

TABLE 1c-continued

| Example No. | R²—X— | R¹ | Salt | Physical properties, etc. |
|---|---|---|---|---|
| 1c-21 | H₃C-CH(CH₃)-NH-C(=O)- | H | HCl | Purified powder MS · APCI (m/z): 321 [M + H]+ |
| 1c-22 | (H₃C)₃C-NH-C(=O)- | H | HCl | Purified powder MS · APCI (m/z): 335 [M + H]+ |
| 1c-23 | pyrazin-2-yl-NH-C(=O)- | H | HCl | Colorless powder MS · APCI (m/z): 357 [M + H]+ |
| 1c-24 | pyrimidin-2-yl-NH-C(=O)- | H | HCl | Colorless powder MS · APCI (m/z): 357 [M + H]+ |
| 1c-25 | 1-ethyl-1H-pyrazol-5-yl-NH-C(=O)- | H | HCl | Colorless powder MS · APCI (m/z): 373 [M + H]+ |
| 1c-26 | thiazol-2-yl-NH-C(=O)- | H | HCl | Colorless powder MS · APCI (m/z): 362 [M + H]+ |
| 1c-27 | 4-methylthiazol-2-yl-NH-C(=O)- | H | HCl | Colorless powder MS · APCI (m/z): 376 [M + H]+ |
| 1c-28 | 1,3,4-thiadiazol-2-yl-NH-C(=O)- | H | HCl | Pale brownish powder MS · APCI (m/z): 363 [M + H]+ |
| 1c-29 | indan-2-yl-NH-C(=O)- | H | HCl | Colorless purified powder MS · APCI (m/z): 395 [M + H]+ |
| 1c-30 | (H₃C-CH₂)(CH₃)N-C(=O)- | H | HCl | Purified powder MS · APCI (m/z): 321 [M + H]+ |

TABLE 1c-continued

| Example No. | R²—X— | R¹ | Salt | Physical properties, etc. |
|---|---|---|---|---|
| 1c-31 | H₃C-CH₂-CH₂-N(CH₃)-C(=O)- | H | HCl | Purified powder MS·APCI (m/z): 335 [M + H]+ |
| 1c-32 | H₃C-O-CH₂-CH₂-CH₂-N(CH₃)-C(=O)- | H | HCl | Brownish purified resin state MS·APCI (m/z): 365 [M + H]+ |
| 1c-33 | H₃C-CH₂-O-CH₂-CH₂-N(CH₃)-C(=O)- | H | HCl | Pale brownish purified powder MS·APCI (m/z): 365 [M + H]+ |
| 1c-34 | H₃C-CH₂-O-CH₂-CH₂-CH₂-N(CH₃)-C(=O)- | H | HCl | Pale brownish purified resin state MS·APCI (m/z): 379 [M + H]+ |
| 1c-35 | H₃C-O-CH₂-CH₂-N(CH₃)-C(=O)- | H | HCl | Purified powder MS·APCI (m/z): 351 |
| 1c-36 | HO-CH₂-CH₂-CH₂-N(CH₃)-C(=O)- | H | HCl | Purified powder MS·APCI (m/z): 351 |
| 1c-37 | H₃C-O-C(=O)-CH₂-N(CH₃)-C(=O)- | H | HCl | Colorless purified powder MS·APCI (m/z): 365 [M + H]+ |
| 1c-38 | (H₃C)₃C-O-C(=O)-CH₂-N(CH₃)-C(=O)- | H | HCl | Colorless purified powder MS·APCI (m/z): 407 [M + H]+ |
| 1c-39 | HO-C(=O)-CH₂-N(CH₃)-C(=O)- | H | HCl | Colorless purified powder MS·APCI (m/z): 351 [M + H]+ |

TABLE 1c-continued

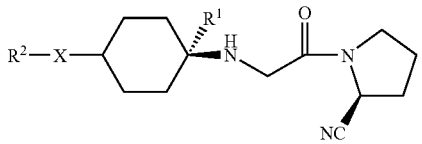

| Example No. | R²—X— | R¹ | Salt | Physical properties, etc. |
|---|---|---|---|---|
| 1c-40 | 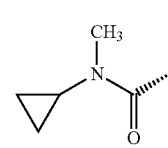 | H | HCl | Colorless purified powder<br>MS · APCI (m/z): 379 [M + H]+ |
| 1c-41 | 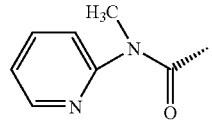 | H | HCl | Colorless purified powder<br>MS · APCI (m/z): 333 [M + H]+ |
| 1c-42 | 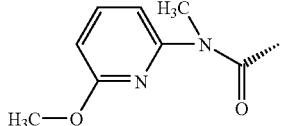 | H | 2HCl | Purified powder<br>MS · APCI (m/z): 370 [M + H]+ |
| 1c-43 | 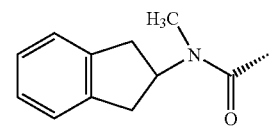 | H | 2HCl | Purified powder<br>MS · APCI (m/z): 400 [M + H]+ |
| 1c-44 | 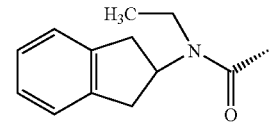 | H | HCl | Colorless purified powder<br>MS · APCI (m/z): 409 [M + H]+ |
| 1c-45 | 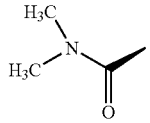 | H | HCl | Colorless purified powder<br>MS · APCI (m/z): 423 [M + H]+ |
| 1c-46 | 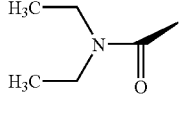 | H | HCl | Purified powder<br>MS · APCI (m/z): 307 [M + H]+ |
| 1c-47 | 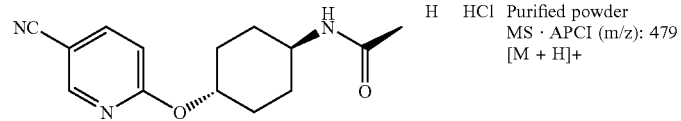 | H | HCl | Colorless powder<br>MS · APCI (m/z): 335 [M + H]+ |
| 1c-48 | 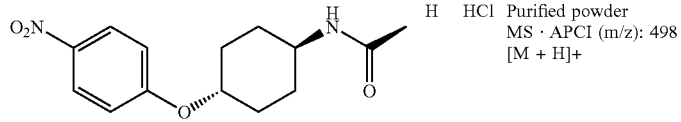 | H | HCl | Purified powder<br>MS · APCI (m/z): 479 [M + H]+ |
| 1c-49 |  | H | HCl | Purified powder<br>MS · APCI (m/z): 498 [M + H]+ |

TABLE 1c-continued

| Example No. | R²—X— | R¹ | Salt | Physical properties, etc. |
|---|---|---|---|---|
| 1c-50 | 4-nitrophenoxy-3-(acetylamino)phenyl group (O₂N-C₆H₄-O-C₆H₄-NHC(O)-) | H | HCl | Purified powder<br>MS · APCI (m/z): 492 [M + H]+ |
| 1c-51 | 5-cyano-2-aminopyridinyl linked to 1-methyl-(acetylamino)cyclohexyl (NC-pyridyl-NH-, H₃C on C, -NHC(O)CH₃) | H | 2HCl | Purified powder<br>MS · APCI (m/z): 492 [M + H]+ |
| 1c-52 | 1-benzylpyrrolidin-3-yl N-methyl acetamide | H | 2HCl | Colorless powder<br>MS · APCI (m/z): 452 [M + H]+ |

TABLE 1d

| Example No. | R²—X— | R¹ | Salt | Physical properties, etc. |
|---|---|---|---|---|
| 1d-1 | pyrrolidin-1-yl-carbonyl | H | HCl | Colorless powder<br>MS · APCI (m/z): 333 [M + H]+ |
| 1d-2 | 2-(hydroxymethyl)pyrrolidin-1-yl-carbonyl | H | HCl | Purified powder<br>MS · APCI (m/z): 363 |
| 1d-3 | 2-(methoxymethyl)pyrrolidin-1-yl-carbonyl | H | HCl | Purified powder<br>MS · APCI (m/z): 377 |
| 1d-4 | azepan-1-yl-carbonyl | H | HCl | Colorless powder<br>MS · APCI (m/z): 361 [M + H]+ |

TABLE 1d-continued

| Example No. | R²—X— | R¹ | Salt | Physical properties, etc. |
|---|---|---|---|---|
| 1d-5 | piperidine-N-C(=O)- | H | HCl | Colorless powder<br>MS·APCI (m/z): 347 [M + H]+ |
| 1d-6 | 4-methyl-piperidine-N-C(=O)- | H | HCl | Colorless powder<br>MS·APCI (m/z): 361 [M + H]+ |
| 1d-7 | 3,3-dimethyl-piperidine-N-C(=O)- | H | HCl | Colorless powder<br>MS·APCI (m/z): 375 [M + H]+ |
| 1d-8 | 4-tert-butyl-piperidine-N-C(=O)- | H | HCl | Purified powder<br>MS·APCI (m/z): 403 [M + H]+ |
| 1d-9 | 4-(methoxycarbonyl)-piperidine-N-C(=O)- | H | HCl | Purified powder<br>MS·APCI (m/z): 405 [M + H]+ |
| 1d-10 | 3-carbamoyl-piperidine-N-C(=O)- | H | Free form | Purified powder<br>MS·APCI (m/z): 390 |
| 1d-11 | 4-carbamoyl-piperidine-N-C(=O)- | H | HCl | Colorless powder<br>MS·APCI (m/z): 390 [M + H]+ |
| 1d-12 | 4-(dimethylamino)-piperidine-N-C(=O)- | H | 2HCl | Colorless powder<br>MS·APCI (m/z): 390 [M + H]+ |
| 1d-13 | 4-(N,N-diethylcarbamoyl)-piperidine-N-C(=O)- | H | HCl | Purified powder<br>MS·APCI (m/z): 446 [M + H]+ |
| 1d-14 | piperazine-N-C(=O)- | H | 2HCl | Colorless powder<br>MS·APCI (m/z): 348 [M + H]+ |
| 1d-15 | 4-ethyl-piperazine-N-C(=O)- | H | 2HCl | Purified powder<br>MS·APCI (m/z): 376 |

TABLE 1d-continued

| Example No. | R²—X— | R¹ | Salt | Physical properties, etc. |
|---|---|---|---|---|
| 1d-16 | (isopropyl-piperazinyl-carbonyl) | H | 2HCl | Colorless powder<br>MS · APCI (m/z): 390 [M + H]+ |
| 1d-17 | (n-butyl-piperazinyl-carbonyl) | H | 2HCl | Colorless powder<br>MS · APCI (m/z): 404 [M + H]+ |
| 1d-18 | (2-hydroxyethyl-piperazinyl-carbonyl) | H | 2HCl | Colorless powder<br>MS · APCI (m/z): 392 [M + H]+ |
| 1d-19 | (carbamoyl-piperazinyl-carbonyl) | H | HCl | Colorless powder<br>MS · APCI (m/z): 390 [M + H] |
| 1d-20 | (propanoyl-piperazinyl-carbonyl) | H | HCl | Purified powder<br>MS · APCI (m/z): 404 |
| 1d-21 | (isobutyryl-piperazinyl-carbonyl) | H | HCl | Purified powder<br>MS · APCI (m/z): 418 |
| 1d-22 | (acetyl-2,6-dimethyl-piperazinyl-carbonyl) | H | HCl | Colorless powder |
| 1d-23 | (pivaloyl-piperazinyl-carbonyl) | H | HCl | Purified powder<br>MS · APCI (m/z): 432 |
| 1d-24 | (3-methylbutanoyl-piperazinyl-carbonyl) | H | HCl | Purified powder<br>MS · APCI (m/z): 432 |
| 1d-25 | (ethoxycarbonyl-piperazinyl-carbonyl) | H | HCl | Colorless crystal<br>Gradually decomposed at around Melting point: 198° C.<br>MS · APCI (m/z): 420 [M + H]+ |

TABLE 1d-continued

| Example No. | R²—X— | R¹ | Salt | Physical properties, etc. |
|---|---|---|---|---|
| 1d-26 | H₃C-SO₂-N-piperazine-C(O)- | H | HCl | Purified powder<br>MS · APCI (m/z): 426 [M + H]+ |
| 1d-27 | 2,6-dimethylmorpholine-N-C(O)- | H | HCl | Colorless crystal<br>Melting point: 207–211° C.<br>MS · APCI (m/z): 377 [M + H] |
| 1d-28 | morpholine-N-C(O)- | H | HCl<br>Methane sulfonic acid | Colorless crystal<br>Melting point: 219° C. (decomposed)<br>MS · APCI (m/z): 349 [M + H]+<br>Colorless crystal<br>Melting point: 217–218° C. (decomposed) |
| 1d-29 | thiomorpholine-N-C(O)- | H | HCl | Colorless powder<br>MS · APCI (m/z): 365 [M + H]+ |
| 1d-30 | 1,1-dioxo-thiomorpholine-N-C(O)- | H | HCl | Colorless powder<br>MS · APCI (m/z): 397 [M + H]+ |
| 1d-31 | 5-nitro-isoindoline-2-C(O)- | H | HCl | Pale brownish powder<br>MS · APCI (m/z): 426 [M + H]+ |
| 1d-32 | isoindoline-2-C(O)- | H | HCl | Colorless crystal<br>Melting point: 198–200° C. (decomposed)<br>MS · APCI (m/z): 381 [M + H] |
| 1d-33 | indoline-1-C(O)- | H | HCl | Pale yellowish powder<br>MS · APCI (m/z): 381 [M + H]+ |
| 1d-34 | 6,7-dihydro-5H-pyrrolo[3,4-b]pyridine-N-C(O)- | H | 2HCl | Colorless crystal<br>Melting point: >300° C.<br>MS · APCI (m/z): 382 [M + H]+ |
| 1d-35 | 1,2,3,4-tetrahydroisoquinoline-2-C(O)- | H | HCl | Purified powder<br>MS · APCI (m/z): 395 |

TABLE 1d-continued

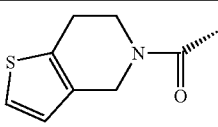

| Example No. | R²—X— | R¹ | Salt | Physical properties, etc. |
|---|---|---|---|---|
| 1d-36 | 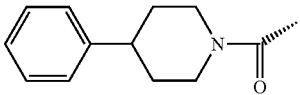 | H | HCl | Purified powder<br>MS · APCI (m/z): 401 |
| 1d-37 | 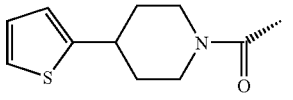 | H | HCl | Purified powder<br>MS · APCI (m/z): 423 |
| 1d-38 | 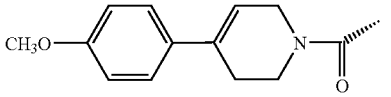 | H | HCl | Colorless powder<br>MS · APCI (m/z): 429 [M + H]+ |
| 1d-39 | 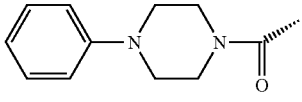 | H | HCl | Colorless powder<br>MS · APCI (m/z): 451 [M + H]+ |
| 1d-40 | 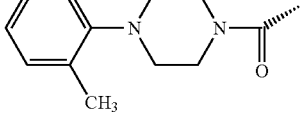 | H | HCl | Purified powder<br>MS · APCI (m/z): 424 |
| 1d-41 | 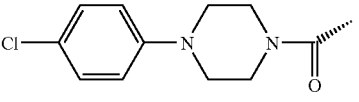 | H | 2HCl | Colorless powder<br>MS · APCI (m/z): 438 [M + H] |
| 1d-42 | 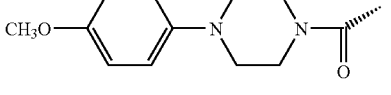 | H | 2HCl | Colorless powder<br>MS · APCI (m/z): 458 [M + H] |
| 1d-43 | 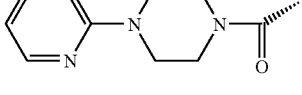 | H | 2HCl | Purified powder<br>MS · APCI (m/z): 454 |
| 1d-44 | 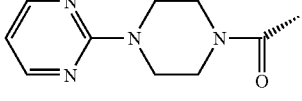 | H | 2HCl | Purified powder<br>MS · APCI (m/z): 425 |
| 1d-45 | 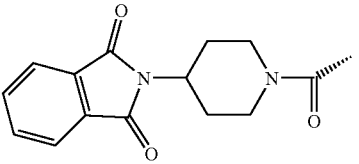 | H | 2HCl | Colorless powder<br>MS · APCI (m/z): 426 [M + H]+ |
| 1d-46 | | H | HCl | Colorless powder<br>MS · APCI (m/z): 492 [M + H]+ |

TABLE 1d-continued

| Example No. | R²—X— | R¹ | Salt | Physical properties, etc. |
|---|---|---|---|---|
| 1d-47 | | H | 2HCl | Purified powder<br>MS · APCI (m/z): 444 [M + H]+ |
| 1d-48 | | H | 2HCl | Purified powder<br>MS · APCI (m/z): 438 |
| 1d-49 | | H | 2HCl | Colorless powder<br>MS · APCI (m/z): 466 [M + H] |
| 1d-50 | | H | 2HCl | Purified powder<br>MS · APCI (m/z): 494 |
| 1d-51 | | H | HCl | Purified powder<br>MS · APCI (m/z): 437 |
| 1d-52 | | H | Maleic acid | Purified powder<br>Melting point: 180–183° C. |
| 1d-53 | | H | HCl | Purified powder<br>MS · APCI (m/z): 465 |
| 1d-54 | | H | HCl | Purified powder<br>MS · APCI (m/z): 521, 519 |

TABLE 1d-continued

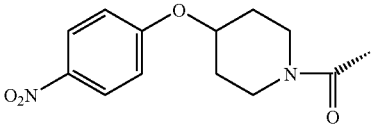

| Example No. | R²—X— | R¹ | Salt | Physical properties, etc. |
|---|---|---|---|---|
| 1d-55 | 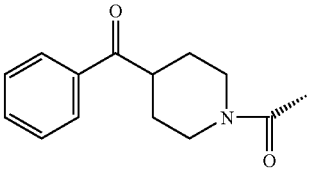 | H | HCl | Purified powder<br>MS · APCI (m/z): 484 |
| 1d-56 | 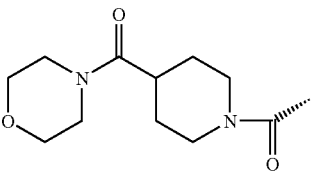 | H | HCl | Purified powder<br>MS · APCI (m/z): 451 |
| 1d-57 | 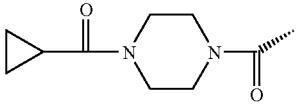 | H | HCl | Purified powder<br>MS · APCI (m/z): 460 [M + H]+ |
| 1d-58 | 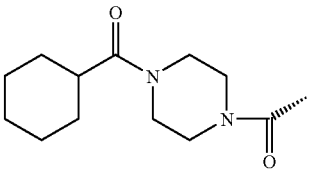 | H | HCl | Purified powder<br>MS · APCI (m/z): 416 |
| 1d-59 | 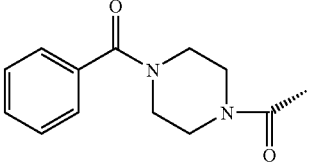 | H | HCl | Purified powder<br>MS · APCI (m/z): 458 |
| 1d-60 | 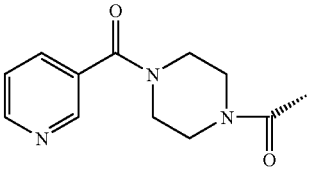 | H | HCl | Colorless powder<br>MS · APCI (m/z): 452 [M + H] |
| 1d-61 | 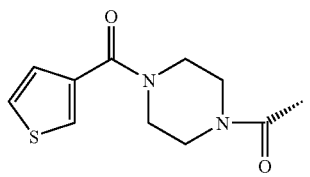 | H | 2HCl | Colorless powder<br>MS · APCI (m/z): 453 [M + H] |
| 1d-62 |  | H | HCl | Colorless powder<br>MS · APCI (m/z): 458 [M + H] |

TABLE 1d-continued

| Example No. | R²—X— | R¹ | Salt | Physical properties, etc. |
|---|---|---|---|---|
| 1d-63 | | H | HCl | Colorless powder<br>MS · APCI (m/z): 455 [M + H] |
| 1d-64 | | H | HCl | Colorless powder<br>MS · APCI (m/z): 461 [M + H]+ |
| 1d-65 | | H | HCl | Purified powder<br>MS · APCI (m/z): [M + H]+ |
| 1d-66 | | H | HCl | Colorless powder<br>MS · APCI (m/z): 467 [M + H]+ |
| 1d-67 | | H | HCl | Purified powder<br>MS · APCI (m/z): 500 [M + H]+ |
| 1d-68 | | H | HCl | Colorless powder<br>MS · APCI (m/z): 481 [M + H]+ |
| 1d-69 | | H | HCl | Purified powder<br>MS · APCI (m/z): 494 [M + H]+ |
| 1d-70 | | H | HCl | Colorless powder<br>MS · APCI (m/z): 482 [M + H]+ |
| 1d-71 | | H | HCl | Purified powder<br>MS · APCI (m/z): 466 [M + H]+ |

TABLE 1d-continued

| Example No. | R²—X— | R¹ | Salt | Physical properties, etc. |
|---|---|---|---|---|
| 1d-72 | | H | 2HCl | Purified powder<br>MS·APCI (m/z): 467 [M + H]+ |
| 1d-73 | | H | HCl | Purified powder<br>MS·APCI (m/z): 472 [M + H]+ |
| 1d-74 | | H | 2HCl | Purified powder<br>MS·APCI (m/z): 514 [M + H]+ |
| 1d-75 | | H | HCl | Purified powder<br>MS·APCI (m/z): 377 |
| 1d-76 | | H | HCl | Purified powder<br>MS·APCI (m/z): 377 |
| 1d-77 | | H | 2HCl | Colorless powder<br>MS·APCI (m/z): 484 [M + H] |
| 1d-78 | | H | HCl | Purified powder<br>MS·APCI (m/z): 376 |
| 1d-79 | | H | HCl | Pale yellowish powder<br>MS·APCI (m/z): 420 [M + H]+ |
| 1d-80 | | H | HCl | Colorless powder<br>MS·APCI (m/z): 419 [M + H] |

TABLE 1d-continued

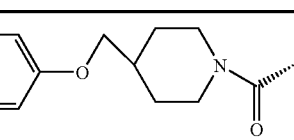

| Example No. | R²—X— | R¹ | Salt | Physical properties, etc. |
|---|---|---|---|---|
| 1d-81 | 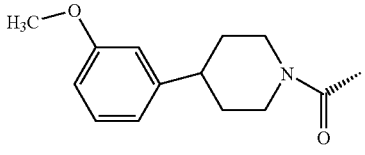 | H | HCl | Colorless purified powder<br>MS · APCI (m/z): 524 [M + H]+ |
| 1d-82 | 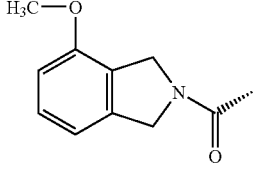 | H | HCl | Colorless purified powder<br>MS · APCI (m/z): 453 [M + H]+ |
| 1d-83 | 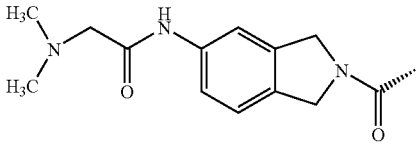 | H | HCl | Colorless powder<br>MS · APCI (m/z): 411 [M + H]+ |
| 1d-84 | 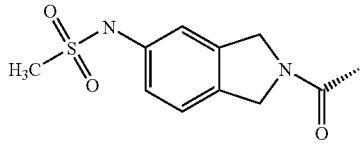 | H | 2HCl | Colorless purified powder<br>MS · APCI (m/z): 481 [M + H]+ |
| 1d-85 | 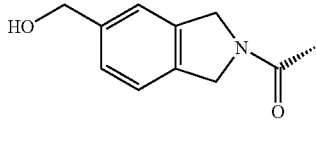 | H | HCl | Colorless purified powder<br>MS · APCI (m/z): 474 [M + H]+ |
| 1d-86 | 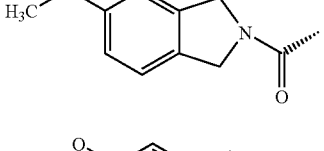 | H | HCl | Purified powder<br>MS · APCI (m/z): 411 [M + H]+ |
| 1d-87 | 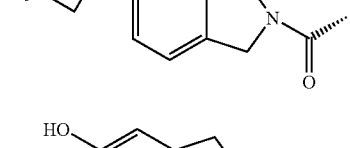 | H | HCl | Colorless purified powder<br>MS · APCI (m/z): 411 [M + H]+ |
| 1d-88 | 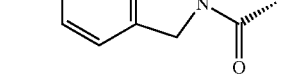 | H | HCl | Colorless purified powder<br>MS · APCI (m/z): 425 [M + H]+ |
| 1d-89 | | H | HCl | Colorless powder<br>MS · APCI (m/z): 397 [M + H]+ |

TABLE 1d-continued

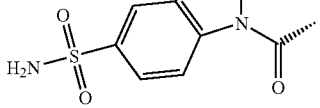

| Example No. | R²—X— | R¹ | Salt | Physical properties, etc. |
|---|---|---|---|---|
| 1d-90 | 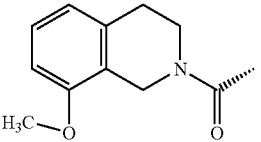 | H | Free form | Colorless solid<br>MS · APCI (m/z): 460 [M + H]+ |
| 1d-91 | 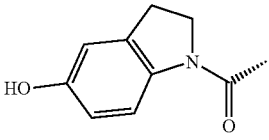 | H | HCl | Colorless powder<br>MS · APCI (m/z): 425 [M + H]+ |
| 1d-92 | 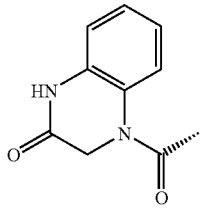 | H | HCl | Colorless powder<br>MS · APCI (m/z): 397 [M + H] |
| 1d-93 | 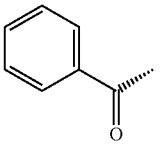 | H | HCl | Purified powder<br>MS · APCI (m/z): 410 |
| 1d-94 | 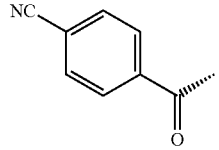 | H | HCl | Purified powder<br>MS · APCI (m/z): 340 [M + H] |
| 1d-95 | 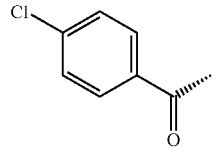 | H | HCl | Purified powder<br>MS · APCI (m/z): 365 [M + H] |
| 1d-96 | 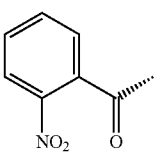 | H | HCl | Colorless powder<br>MS · APCI (m/z): 374 [M + H] |
| 1d-97 | | H | HCl | Yellowish powder<br>MS · APCI (m/z): 385 [M + H] |

TABLE 1d-continued

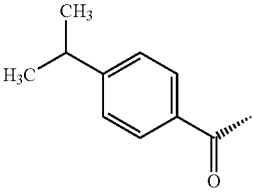

| Example No. | R²—X— | R¹ | Salt | Physical properties, etc. |
|---|---|---|---|---|
| 1d-98 | 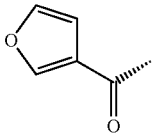 | H | HCl | Colorless powder<br>MS · APCI (m/z): 382 [M + H] |
| 1d-99 | 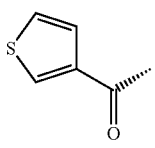 | H | HCl | Purified powder<br>MS · APCI (m/z): 330 [M + H] |
| 1d-100 | 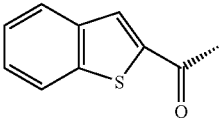 | H | HCl | Purified powder<br>MS · APCI (m/z): 346 [M + H] |
| 1d-101 | 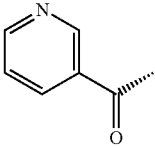 | H | HCl | Colorless powder<br>MS · APCI (m/z): 396 [M + H] |
| 1d-102 | 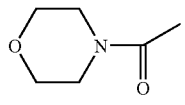 | H | 2HCl | Colorless powder<br>MS · APCI (m/z): 341 [M + H] |
| 1d-103 | 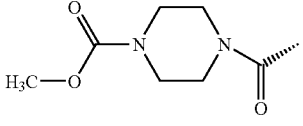 | Me | HCl | Purified powder<br>MS · APCI (m/z): 363 [M + H] |
| 1d-104 | 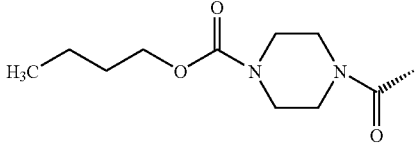 | H | HCl | Colorless powder<br>MS · APCI (m/z): 406 [M + H] |
| 1d-105 | 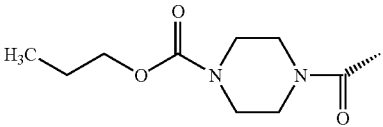 | H | HCl | Colorless powder<br>MS · APCI (m/z): 448 [M + H] |
| 1d-106 |  | H | HCl | Colorless powder<br>MS · APCI (m/z): 434 [M + H] |

TABLE 1d-continued

| Example No. | R²—X— | R¹ | Salt | Physical properties, etc. |
|---|---|---|---|---|
| 1d-107 | | H | HCl | Colorless powder<br>MS · APCI (m/z): 468 [M + H] |
| 1d-108 | | H | HCl | Pale yellowish powder<br>MS · APCI (m/z): 472 [M + H] |
| 1d-109 | | H | HCl | Pale yellowish powder<br>MS · APCI (m/z): 471 [M + H] |
| 1d-110 | | H | HCl | Purified powder<br>MS · APCI (m/z): 439 [M + H]+ |
| 1d-111 | | H | HCl | Colorless purified powder<br>MS · APCI (m/z): 425 [M + H]+ |
| 1d-112 | | H | HCl | Purified powder<br>MS · APCI (m/z): 453 [M + H]+ |
| 1d-113 | | H | HCl | Colorless purified powder<br>MS · APCI (m/z): 454 [M + H]+ |
| 1d-114 | | H | HCl | Colorless purified powder<br>MS · APCI (m/z): 438 [M + H]+ |

TABLE 1d-continued

| Example No. | R²—X— | R¹ | Salt | Physical properties, etc. |
|---|---|---|---|---|
| 1d-115 | | H | 2HCl | Purified powder<br>MS · APCI (m/z): 480 [M + H]+ |
| 1d-116 | | H | HCl | Colorless purified powder<br>MS · APCI (m/z): 452 [M + H]+ |
| 1d-117 | | H | HCl | Colorless purified powder<br>MS · APCI (m/z): 424 [M + H]+ |
| 1d-118 | | H | HCl | Colorless purified powder<br>MS · APCI (m/z): 468 [M + H]+ |
| 1d-119 | | H | HCl | Colorless purified powder<br>MS · APCI (m/z): 478 [M + H]+ |
| 1d-120 | | H | HCl | Colorless purified powder<br>MS · APCI (m/z): 494 [M + H]+ |
| 1d-121 | | H | 2HCl | Colorless purified powder<br>MS · APCI (m/z): 410 |
| 1d-122 | | H | HCl | Colorless purified powder<br>MS · APCI (m/z): 478 [M + H]+ |

TABLE 1d-continued

| Example No. | R²—X— | R¹ | Salt | Physical properties, etc. |
|---|---|---|---|---|
| 1d-123 | | H | HCl | Colorless purified powder<br>MS · APCI (m/z): 452 [M + H]+ |
| 1d-124 | | H | HCl | Colorless purified powder<br>MS · APCI (m/z): 488 [M + H]+ |
| 1d-125 | | H | HCl | Colorless purified powder<br>MS · APCI (m/z): 406 [M + H]+ |
| 1d-126 | | H | HCl | Colorless powder<br>MS · APCI (m/z): 438 [M + H] |
| 1d-127 | | H | HCl | Colorless powder<br>MS · APCI (m/z): 467 [M + H] |
| 1d-128 | | H | HCl | Colorless powder<br>MS · APCI (m/z): 454 [M + H] |
| 1d-129 | | H | HCl | Colorless powder<br>MS · APCI (m/z): 474 [M + H] |

TABLE 1d-continued

| Example No. | R²—X— | R¹ | Salt | Physical properties, etc. |
|---|---|---|---|---|
| 1d-130 | | H | 2HCl | Colorless powder<br>MS · APCI (m/z): 481 [M + H] |
| 1d-131 | | H | 2HCl | Colorless powder<br>MS · APCI (m/z): 424 [M + H] |
| 1d-132 | | H | HCl | Colorless powder<br>MS · APCI (m/z): 438 [M + H] |
| 1d-133 | | H | HCl | Yellow brownish powder<br>MS · APCI (m/z): 467 [M + H] |
| 1d-134 | | H | HCl | Colorless powder<br>MS · APCI (m/z): 454 [M + H] |
| 1d-135 | | H | HCl | Colorless powder<br>MS · APCI (m/z): 474 [M + H] |
| 1d-136 | | H | 2HCl | Pale brownish powder<br>MS · APCI (m/z): 481 [M + H] |
| 1d-137 | | H | 2HCl | Colorless powder<br>MS · APCI (m/z): 424 [M + H] |

TABLE 1d-continued

| Example No. | R²—X— | R¹ | Salt | Physical properties, etc. |
|---|---|---|---|---|
| 1d-138 | | H | 2HCl | Pale yellowish powder<br>MS · APCI (m/z): 468 [M + H]+ |
| 1d-139 | | H | HCl | Colorless powder<br>MS · APCI (m/z): 411 [M + H]+ |
| 1d-140 | | H | HCl | Colorless powder<br>MS · APCI (m/z): 468 [M + H]+ |
| 1d-141 | | H | HCl | Colorless powder<br>MS · APCI (m/z): 469 [M + H] |
| 1d-142 | | H | HCl | Colorless powder<br>MS · APCI (m/z): 468 [M + H]+ |
| 1d-143 | | H | HCl | Colorless powder<br>MS · APCI (m/z): 469 [M + H]+ |
| 1d-144 | | H | HCl | Purified powder<br>MS · APCI (m/z): 363 [M + H]+ |
| 1d-145 | | H | HCl | Colorless powder<br>MS · APCI (m/z): 349 [M + H]+ |
| 1d-146 | | H | HCl | Purified powder<br>MS · APCI (m/z): 381 [M + H]+ |

TABLE 1d-continued

Structure: R²—X—[cyclohexyl with R¹]—NH—CH₂—C(O)—N(pyrrolidine-2-CN)

| Example No. | R²—X— | R¹ | Salt | Physical properties, etc. |
|---|---|---|---|---|
| 1d-147 | 3-(hydroxymethyl)-2-acetyl-1,2,3,4-tetrahydroisoquinolin-yl | H | HCl | Colorless powder<br>MS · APCI (m/z): 425 [M + H]+ |
| 1d-148 | 4-(pyridin-2-yl)piperazine-1-carbonyl | H | 2HCl | Colorless powder<br>MS · APCI (m/z): 425 [M + H]+ |
| 1d-149 | 4-(piperidin-1-yl)piperidine-1-carbonyl | H | 2HCl | Colorless resin state<br>MS · APCI (m/z): 430 [M + H]+ |
| 1d-150 | 4-hydroxy-4-phenylpiperidine-1-carbonyl | H | HCl | Colorless powder<br>MS · APCI (m/z): 439 [M + H]+ |
| 1d-151 | 4-(2-methylphenyl)piperazine-1-carbonyl | H | 2HCl | Purified powder<br>MS · APCI (m/z): 438 [M + H]+ |
| 1d-152 | 4-benzylpiperazine-1-carbonyl | H | 2HCl | Colorless powder<br>MS · APCI (m/z): 438 [M + H]+ |

TABLE 2

| Example No. | R²—X— | R¹ | Salt | Physical properties, etc. |
|---|---|---|---|---|
| 2-1 | 3-cyanophenyl-NH— (R) | Me | 2HCl | Purified powder<br>MS · APCI (m/z): 366 |
| 2-2 | 3-cyanophenyl-NH— (S) | Me | 2HCl | Purified powder<br>MS · APCI (m/z): 366 |

TABLE 2-continued

R²—X—[cyclohexyl(R¹)]—NH—C(O)—[pyrrolidine-CN]

| Example No. | R²—X— | R¹ | Salt | Physical properties, etc. |
|---|---|---|---|---|
| 2-3 | NC-C₆H₄-NH- | Me | 2HCl | Purified powder MS · APCI (m/z): 366 |
| 2-4 | NC-C₆H₄-NH- | Me | 2HCl | Purified powder MS · APCI (m/z): 366 |
| 2-5 | 2-CN-C₆H₄-NH- | Me | 2HCl | Purified powder MS · APCI (m/z): 366 |
| 2-6 | H₃CO-C₆H₄-NH- | Me | 2HCl | Purified powder MS · APCI (m/z): 371 |
| 2-7 | F-C₆H₄-NH- | Me | 2HCl | Purified powder MS · APCI (m/z): 359 |
| 2-8 | cyclohexyl-NH- | Me | 2HCl | Purified powder MS · APCI (m/z): 347 |

TABLE 3

R²—X—[cyclohexyl(R¹)]—NH—C(O)—[pyrrolidine-CN]

| Example No. | R²—X— | R¹ | Salt | Physical properties, etc. |
|---|---|---|---|---|
| 3-1 | pyridin-2-yl-CH₂-NH-C(O)- | H | 2HCl | Colorless powder MS · APCI (m/z): 370 [M + H]+ |
| 3-2 | (2-methylpyridin-3-yl)-NH-C(O)- | H | 2HCl | Colorless powder MS · APCI (m/z): 370 [M + H]+ |
| 3-3 | pyrimidin-5-yl-NH-C(O)- | H | 2HCl | Colorless powder MS · APCI (m/z): 357 [M + H]+ |
| 3-4 | pyrimidin-2-yl-CH₂-NH-C(O)- | H | 2HCl | Resin state MS · APCI (m/z): 371 [M + H]+ |

TABLE 3-continued

| Example No. | R²—X— | R¹ | Salt | Physical properties, etc. |
|---|---|---|---|---|
| 3-5 | pyrazin-2-yl-CH₂-NH-C(O)- | H | 2HCl | Resin state<br>MS·APCI (m/z): 371 [M + H]+ |
| 3-6 | 6-methoxypyridin-2-yl-CH₂-NH-C(O)- | H | 2HCl | Resin state<br>MS·APCI (m/z): 400 [M + H]+ |
| 3-7 | 2-(pyridin-2-yl)ethyl-NH-C(O)- | H | 2HCl | Resin state<br>MS·APCI (m/z): 384 [M + H]+ |
| 3-8 | CH₃O-CH₂CH₂-NH-C(O)- | H | HCl | Colorless powder<br>MS·APCI (m/z): 337 [M + H]+ |
| 3-9 | (CH₃CH₂)₂N-C(O)- | H | HCl | Colorless powder<br>MS·APCI (m/z): 335 [M + H]+ |
| 3-10 | 4-hydroxypiperidin-1-yl-C(O)- | H | HCl | Pale yellowish powder<br>MS·APCI (m/z): 363 [M + H]+ |
| 3-11 | 4-methylpiperazin-1-yl-C(O)- | H | 2HCl | Colorless powder<br>MS·APCI (m/z): 362 [M + H]+ |
| 3-12 | 6,7-dimethoxy-3,4-dihydroisoquinolin-2(1H)-yl-C(O)- | H | HCl | Colorless powder<br>MS·APCI (m/z): 455 [M + H]+ |

TABLE 4

| Example No. | R²—X— | R¹ | Salt | Physical properties, etc. |
|---|---|---|---|---|
| 4-1 | O₂N-pyridin-2-yl-NH- (5-nitro) | H | 2HCl | Pale yellowish powder<br>MS · APCI (m/z): 391 [M + H]+ |
| 4-2 | pyridin-2-yl-NH- | H | 2HCl | Colorless powder<br>MS · APCI (m/z): 346 [M + H]+ |
| 4-3 | NC-pyridin-2-yl-NH- (5-cyano) | H | 2HCl | Pale yellowish powder<br>MS · APCI (m/z): 371 [M + H]+ |
| 4-4 | F₃C-pyridin-2-yl-NH- (5-CF₃) | H | 2HCl | Colorless powder<br>MS · APCI (m/z): 414 [M + H]+ |
| 4-5 | pyrimidin-2-yl-NH- | H | HCl | Colorless powder<br>Melting point: >300° C.<br>MS · APCI (m/z): 347 [M + H]+ |
| 4-6 | Br-pyrimidin-2-yl-NH- (5-Br) | H | 2HCl | Colorless powder<br>MS · APCI (m/z): 425 427 [M + H]+ |
| 4-7 | H₃C-S-pyrimidin-2-yl-NH- (5-SMe) | H | 2HCl | Colorless powder<br>MS · APCI (m/z): 393 [M + H]+ |
| 4-8 | Cl-pyrimidin-2-yl-NH- (5-Cl) | H | 2HCl | Colorless powder<br>MS · APCI (m/z): 381 |
| 4-9 | thiazol-2-yl-NH- | H | 2HCl | Colorless powder<br>MS · APCI (m/z): 352 [M + H]+ |
| 4-10 | O₂N-pyridin-2-yl-NH- (5-nitro) | H | 2HCl | Pale yellowish powder<br>MS · APCI (m/z): 391 [M + H]+ |
| 4-11 | O₂N-pyridin-2-yl-O- (5-nitro) | H | HCl | Colorless powder<br>MS · APCI (m/z): 392 [M + H]+ |
| 4-12 | NC-pyridin-2-yl-O- (5-cyano) | H | HCl | Colorless powder<br>MS · APCI (m/z): 372 [M + H]+ |

TABLE 4-continued

| Example No. | R²—X— | R¹ | Salt | Physical properties, etc. |
|---|---|---|---|---|
| 4-13 | 5-bromopyrimidin-2-yloxy | H | HCl | Colorless powder<br>MS · APCI (m/z): 426 [M + H]+ |
| 4-14 | 5-chloropyrimidin-2-yloxy | H | HCl | Colorless powder<br>MS · APCI (m/z): 382 [M + H]+ |
| 4-15 | 5-(methylthio)pyrimidin-2-yloxy | H | HCl | Colorless powder<br>MS · APCI (m/z): 394 [M + H]+ |
| 4-16 | pyrimidin-2-yloxy | H | HCl | Colorless powder<br>Melting point: 80° C.-(Decomposed)<br>MS · APCI (m/z): 348 [M + H]+ |
| 4-17 | 5-(2-furyl)pyrimidin-2-yloxy | H | HCl | Colorless powder<br>MS · APCI (m/z): 414 [M + H]+ |
| 4-18 | 4-nitrophenoxy | H | HCl | Pale yellowish powder<br>MS · APCI (m/z): 391 [M + H]+ |
| 4-19 | 3-pyridylaminocarbonylmethyl | H | 2HCl | Colorless powder<br>MS · APCI (m/z): 374 [M + H]+ |
| 4-20 | H₂N-C(O)- | H | HCl | Colorless purified powder<br>MS · APCI (m/z): 297 [M + H]+ |
| 4-21 | (CH₃)₂N-C(O)- | H | HCl | Purified powder<br>MS · APCI (m/z): 325 [M + H]+ |
| 4-22 | ethoxycarbonylmethyl(methyl)aminocarbonyl | H | HCl | Colorless purified powder<br>MS · APCI (m/z): 397 [M + H]+ |
| 4-23 | 4-(ethoxycarbonyl)piperazin-1-ylcarbonyl | H | HCl | Colorless powder<br>MS · APCI (m/z): 438 [M + H]+ |

TABLE 4-continued

| Example No. | R²—X— | R¹ | Salt | Physical properties, etc. |
|---|---|---|---|---|
| 4-24 | methyl piperidine-4-carboxylate, N-acyl | H | HCl | Colorless powder<br>MS · APCI (m/z): 423 [M + H]+ |
| 4-25 | 4-(3-methoxyphenyl)piperidine, N-acyl | H | HCl | Colorless.purified powder<br>MS · APCI (m/z): 471 [M + H]+ |
| 4-26 | morpholine, N-acyl | H | HCl | Colorless powder<br>MS · APCI (m/z): 367 [M + H]+ |
| 4-27 | pyrrolidine, N-acyl | H | HCl | Colorless powder<br>MS · APCI (m/z): 351 [M + H]+ |
| 4-28 | isoindoline, N-acyl | H | HCl | Colorless powder<br>MS · APCI (m/z): 399 [M + H]+ |
| 4-29 | 5-amino-isoindoline, N-acyl | H | 2HCl | Colorless powder<br>MS · APCI (m/z): 414 [M + H]+ |
| 4-30 | 5-(hydroxymethyl)isoindoline, N-acyl | H | HCl | Colorless powder<br>MS · APCI (m/z): 429 [M + H]+ |
| 4-31 | 5-nitro-isoindoline, N-acyl | H | HCl | Colorless powder<br>MS · APCI (m/z): 444 [M + H]+ |
| 4-32 | 4-(N,N-dimethylcarbamoyloxy)isoindoline, N-acyl | H | HCl | Colorless powder<br>MS · APCI (m/z): 486 [M + H]+ |

TABLE 5

R²—X—[cyclohexane]—R¹, NH₂

| Reference Example No. | R²—X— | R¹ | Salt | Physical properties, etc. |
|---|---|---|---|---|
| 3-1 | O₂N-pyridin-2-yl-NH— | H | Free form | Yellowish crystal<br>Melting point: 156–158° C. |
| 3-2 | pyridin-2-yl-NH— | H | Free form | Pale brownish crystal<br>Melting point: 110–122° C. |
| 3-3 | NC-pyridin-2-yl-NH— | H | Free form | Colorless crystal<br>Melting point: 152–154° C. |
| 3-4 | CF₃-pyridin-2-yl-NH— | H | Free form | Pale brownish crystal<br>Melting point: 77–80° C. |
| 3-5 | 3-CN-pyridin-2-yl-NH— | H | Free form | Pale yellowish needle-like crystal<br>Melting point: 107–108° C. |
| 3-6 | 3-NO₂-pyridin-2-yl-NH— | H | Free form | Yellowish needle-like crystal<br>Melting point: 84° C.- |
| 3-7 | pyrimidin-2-yl-NH— | H | Free form | Colorless crystal<br>Melting point: 128–129° C. |
| 3-8 | 5-Br-pyrimidin-2-yl-NH— | H | Free form | Colorless crystal<br>Melting point: 140–141° C. |
| 3-9 | 5-(H₃C-S)-pyrimidin-2-yl-NH— | H | Free form | Pale yellowish crystal<br>Melting point: 116–118° C. |
| 3-10 | 5-Cl-pyrimidin-2-yl-NH— | H | 2HCl | Colorless crystal<br>Melting point: >300° C. |
| 3-11 | pyrazin-2-yl-NH— | H | Free form | Pale yellowish needle-like crystal<br>Melting point: 92–94° C. |
| 3-12 | thiazol-2-yl-NH— | H | Free form | Brownish crystal<br>Melting point: 120–123° C. |

TABLE 5-continued
| | | | | |
|---|---|---|---|---|
| 3-13 | 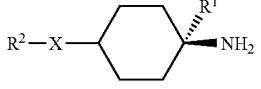 | H | Free form | Powder MS · APCI (m/z): 228, 226 |
| 3-14 | 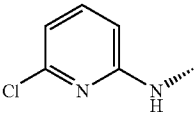 | H | Free form | Oil MS · APCI (m/z): 228, 226 |
| 3-15 | 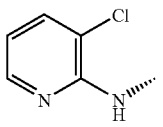 | H | Free form | Oil MS · APCI (m/z): 228, 226 |
| 3-16 | 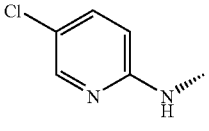 | H | Free form | Oil |
| 3-17 | 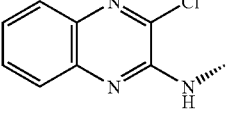 | H | Free form | Powder MS · APCI (m/z): 261 |
| 3-18 |  | H | Free form | Oil MS · APCI (m/z): 221 |
| 3-19 | 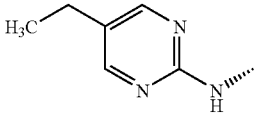 | H | Free form | Powder MS · APCI (m/z): 218 |
| 3-20 | 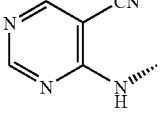 | H | Free form | Powder MS · APCI (m/z): 218 |
| 3-21 | 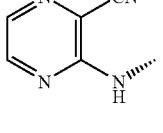 | H | Free form | Yellowish oil MS · APCI (m/z): 239 [M + H]+ |

TABLE 5-continued
| | | | | |
|---|---|---|---|---|
| 3-22 | 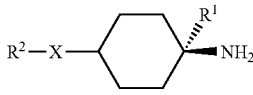 | H | Free form | Yellowish foam MS · APCI (m/z): 311 [M + H]+ |
| 3-23 | 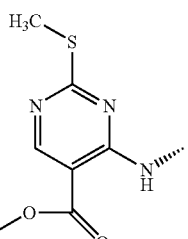 | H | Free form | Yellowish oil MS · APCI (m/z): 312 [M + H]+ |
| 3-24 | 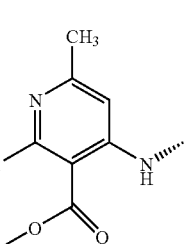 | H | Free form | Colorless oil |
| 3-25 | 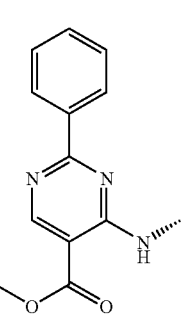 | H | Free form | Colorless oil |
| 3-26 | 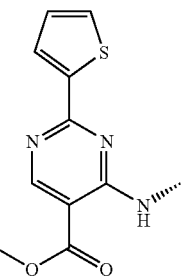 | H | Free form | Powder MS · APCI (m/z): 269 |
| 3-27 | 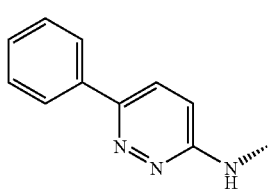 | H | Free form | Yellowish oil MS · APCI (m/z): 259 [M + H]+ |

TABLE 5-continued
| | R² group | R¹ | Form | Properties |
|---|---|---|---|---|
| 3-28 | 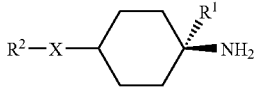 | H | Free form | Oil MS · APCI (m/z): 250 |
| 3-29 |  | H | Free form | Powder MS · APCI (m/z): 236 |
| 3-30 | 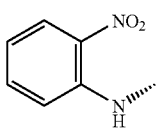 | H | Free form | Powder MS · APCI (m/z): 234 |
| 3-31 | 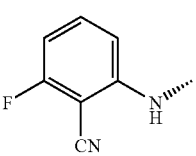 | H | Free form | Oil MS · APCI (m/z): 234 |
| 3-32 | 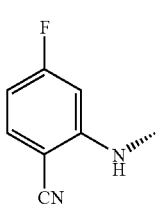 | H | Free form | Powder MS · APCI (m/z): 284 |
| 3-33 | 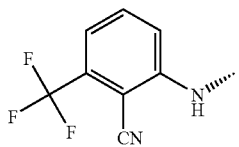 | H | Free form | Powder MS · APCI (m/z): 231 |
| 3-34 | 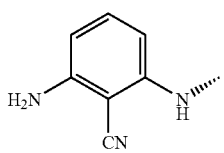 | H | Free form | Powder MS · APCI (m/z): 234 |
| 3-35 | 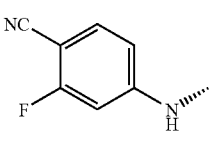 | H | Free form | Pale brownish crystal Melting point: 99–102° C. MS · APCI (m/z): 216 [M + H] |
| 3-36 | 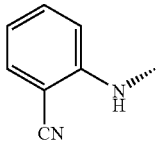 | H | Free form | Yellowish resin MS · APCI (m/z): 234 [M + H] |

TABLE 5-continued

| Reference Example No. | R¹—X—Y— | R² | Salt | Physical properties, etc. |
|---|---|---|---|---|
| 3-37 | 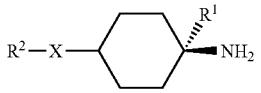 | H | Free form | Pale reddish brownish powder MS · APCI (m/z): 296, 294 [M + H] |
| 3-38 | 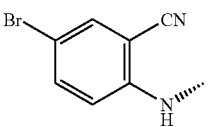 | H | Free form | Pale reddish brownish powder MS · APCI (m/z): 246 [M + H] |
| 3-39 | 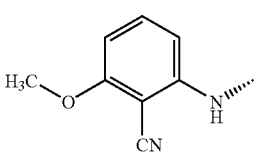 | H | Free form | Oil |
| 3-40 | 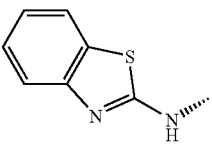 | H | Free form | Oil |
| 3-41 | 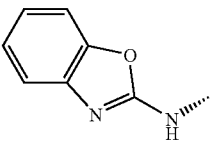 | H | Free form | Yellowish crystal Melting point: 135–136.5° C. |
| 3-42 | 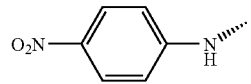 | H | Free form | Yellowish powder MS · APCI (m/z): 242 [M + H]+ |
| 3-43 | 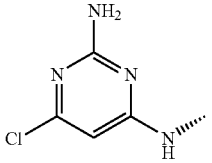 | H | Free form | Yellowish crystal Melting point: 81.5–83.5° C. |
| 3-44 | 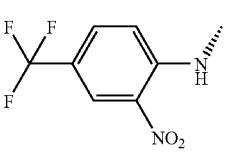 | H | Free form | Reddish liquid MS · APCI (m/z): 266 [M + H]+ |
| 3-45 | 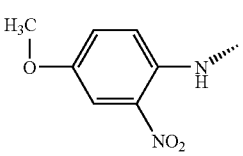 | H | Free form | Dark reddish powder MS · APCI (m/z): 253 [M + H]+ |

TABLE 5-continued

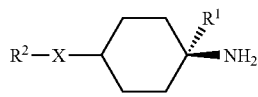

| Reference Example No. | R²—X— | R¹ | Salt | Physical properties, etc. |
|---|---|---|---|---|
| 3-46 | (6-chloropyridazin-3-yl)amino | H | Free form | Powder MS · APCI (m/z): 229, 227 |
| 3-47 | (2-chloro[1]benzofuro[3,2-d]pyrimidin-4-yl)amino | H | Free form | Oil |
| 3-48 | (pyridazin-3-yl)amino | H | Free form | Powder MS · APCI (m/z): 193 |
| 3-49 | ([1]benzofuro[3,2-d]pyrimidin-4-yl)amino | H | Free form | Oil |
| 3-50 | [5-(ethoxycarbonyl)-2-morpholin-4-ylpyrimidin-4-yl]amino | H | Free form | Colorless oil |

| Reference Example No. | R²—X— | R¹ | Salt | Physical properties, etc. |
|---|---|---|---|---|
| 3-51 | 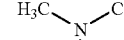 | H | Free form | Colorless oil |

TABLE 5-continued

| | R² —X— [cyclohexyl with R¹ and NH₂] | R¹ | Form | Appearance |
|---|---|---|---|---|
| 3-52 | ethyl 2-(pyrrolidin-1-yl)-4-(NH-)pyrimidine-5-carboxylate | H | Free form | Colorless oil |
| 3-53 | N,N-dimethyl 2-(morpholin-4-yl)-4-(NH-)pyrimidine-5-carboxamide | H | Free form | Yellowish oil |
| 3-54 | [2-(pyrrolidin-1-yl)-4-(NH-)pyrimidin-5-yl](morpholin-4-yl)methanone | H | Free form | Colorless oil |
| 3-55 | [2-(dimethylamino)-4-(NH-)pyrimidin-5-yl](morpholin-4-yl)methanone | H | Free form | Colorless oil |
| 3-56 | [2-(methylthio)-4-(NH-)pyrimidin-5-yl](morpholin-4-yl)methanone | H | Free form | Yellowish oil |

TABLE 5-continued

| No. | R²—X— | R¹ | Form | Properties |
|---|---|---|---|---|
| 3-57 | (2-methylthio-4-(methylamino)-5-(pyrrolidin-1-ylcarbonyl)pyrimidine) | H | Free form | Colorless foam |
| 3-58 | (2-methylthio-4-(methylamino)-5-(N,N-dimethylcarbamoyl)pyrimidine) | H | Free form | Colorless oil |
| 3-59 | (2-phenyl-4-(methylamino)-5-(morpholin-4-ylcarbonyl)pyrimidine) | H | Free form | Colorless oil |
| 4 | (5-nitro-2-(methylamino)pyridine) | H | Free form | Pale yellowish solid Melting point: 153–155° C. |
| 5-1 | (3-nitro-2-(methylamino)pyridine) | H | 2HCl | Yellowish crystal Melting point: 219–222° C. |
| 5-2 | (5-cyano-2-(methylamino)pyrimidine) | H | 2HCl | Colorless powder MS·APCI (m/z): 217 [M + H]+ |
| 5-3 | (3-cyano-2-(methylamino)pyridine) | H | 2HCl | Colorless crystal Melting point: 215–218° C. |
| 5-4 | (2-(methylamino)pyrimidine) | H | 2HCl | Colorless crystal Melting point: 245–250° C. |

TABLE 5-continued

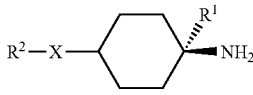

| | | R¹ | | |
|---|---|---|---|---|
| 5-5 | 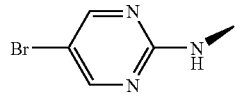 | H | 2HCl | Colorless crystal Melting point: 303° C. |
| 5-6 | 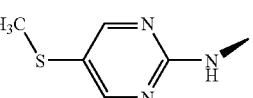 | H | 2HCl | Yellowish crystal Melting point: 234–237° C. |
| 7-1 | 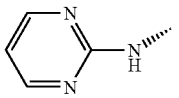 | Me | Free form | Colorless crystal Melting point: 121–123° C. |
| 7-2 | 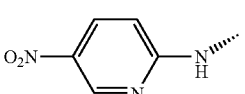 | Me | Free form | Yellowish crystal Melting point: 164–166° C. |
| 7-3 | 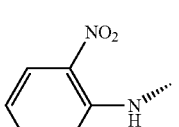 | Me | Free form | Yellowish crystal Melting point: 40–43° C. |
| 7-4 | 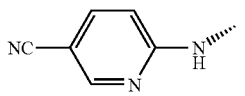 | Me | Free form | Pale yellowish crystal Melting point: 147–148° C. |
| 7-5 | 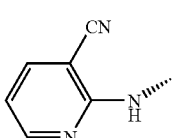 | Me | Free form | Colorless crystal Melting point: 111–112° C. |
| 7-6 | 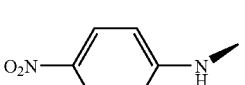 | Me | Free form | Pale brownish crystal Melting point: 121–124° C. |
| 7-7 | 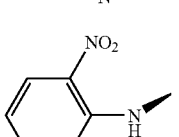 | Me | Free form | Yellowish crystal Melting point: 58–59° C. |
| 7-8 | 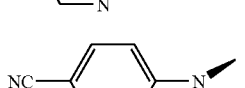 | Me | Free form | Colorless crystal Melting point: 182–184° C. |
| 7-9 | 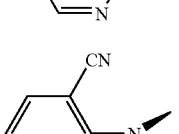 | Me | Free form | Pale brownish crystal Melting point: 76–79° C. |
| 7-10 | 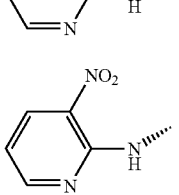 | CH₂OH | 2HCl | Pale yellowish solid MS · APCI (m/z): 267 [M + H]+ |

TABLE 5-continued

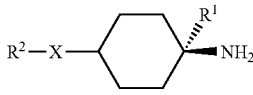

| 7-11 | 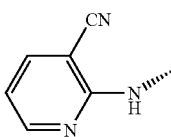 | CH₂OH | 2HCl | Colorless solid<br>MS · APCI (m/z):<br>247 [M + H]+ |
| --- | --- | --- | --- | --- |
| 7-12 | 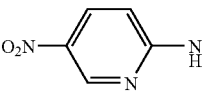 | CH₂OH | 2HCl | Yellowish powder<br>MS · APCI (m/z):<br>267 [M + H]+ |
| 7-13 | 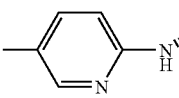 | CH₂OH | Free form | Colorless oil<br>MS · APCI (m/z):<br>247 [M + H]+ |
| 7-14 | 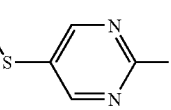 | CH₂OH | 2HCl | Pale yellowish solid<br>MS · APCI (m/z):<br>269 [M + H]+ |
| 7-15 | 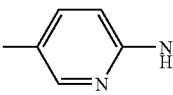 | CH₂OH | 2HCl | Colorless powder<br>MS · APCI (m/z):<br>247 [M + H]+ |
| 7-16 | 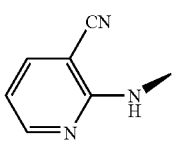 | CH₂OH | 2HCl | Colorless solid<br>MS · APCI (m/z):<br>247 [M + H]+ |
| 7-17 | 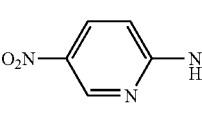 | CH₂OH | 2HCl | Yellowish powder<br>MS · APCI (m/z):<br>267 [M + H]+ |
| 7-18 | 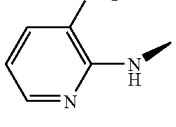 | CH₂OH | 2HCl | Pale yellowish solid<br>MS · APCI (m/z):<br>267 [M + H]+ |
| 7-19 | 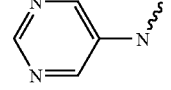 | Me | 2HCl | Colorless resin state<br>MS · APCI (m/z):<br>207 [M + H]+ |
| 7-20 | 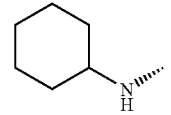 | Me | Free form | Powder<br>MS · APCI (m/z): 311 |
| 7-21 | 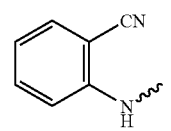 | Me | | |
| 7-22 | 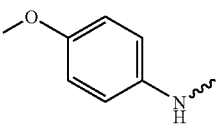 | Me | | |

TABLE 5-continued

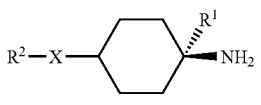

| | R²—X— | R¹ | | Physical properties, etc. |
|---|---|---|---|---|
| 7-23 | 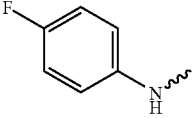 | Me | | |
| 8-1 | 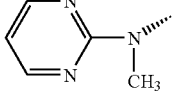 | H | Free form | Colorless resin MS · APCI (m/z): 207 [M + H]+ |
| 8-2 | 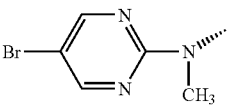 | H | Free form | Colorless crystal Melting point: 109–112° C. |
| 8-3 | 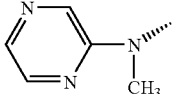 | H | Free form | Pale brownish resin MS · APCI (m/z): 207 [M + H]+ |
| 8-4 | 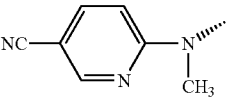 | H | Free form | Colorless crystal Melting point: 85–87° C. |

TABLE 6

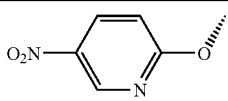

| Reference Example No. | R²—X— | R¹ | Salt | Physical properties, etc. |
|---|---|---|---|---|
| 9-1 | 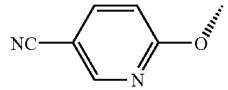 | H | HCl | Colorless crystal Melting point: 271° C. |
| 9-2 | 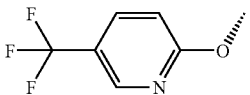 | H | HCl | Colorless crystal Melting point: 289° C. |
| 9-3 | 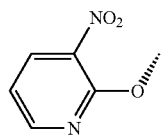 | H | HCl | Colorless crystal Melting point: 253–254° C. |
| 9-4 | NO₂ structure | H | HCl | Pale yellowish crystal Melting point: 230° C. |

TABLE 6-continued

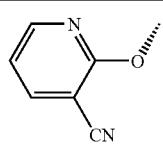

| Reference Example No. | R²—X— | R¹ | Salt | Physical properties, etc. |
|---|---|---|---|---|
| 9-5 | 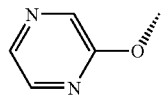 | H | Free form | Colorless crystal Melting point: 70–72° C. |
| 9-6 | 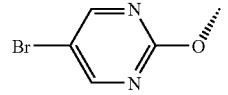 | H | Free form | Colorless crystal Melting point: 58–59° C. |
| 9-7 | 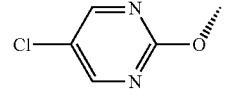 | H | HCl | Colorless crystal Melting point: 284° C. (decomposed) |
| 9-8 | 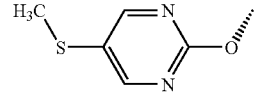 | H | HCl | Colorless crystal Melting point: 279–280° C. (decomposed) |
| 9-9 | 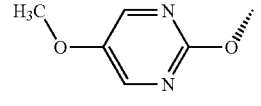 | H | HCl | Colorless crystal Melting point: 275° C. (decomposed) |
| 9-10 | 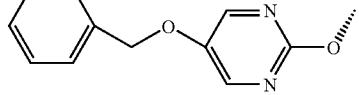 | H | HCl | Colorless crystal Melting point: 275–276° C. (decomposed) |
| 9-11 | 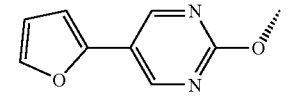 | H | HCl | Colorless crystal Melting point: 194° C. |
| 9-12 | 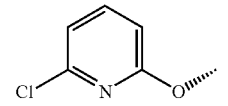 | H | Free form | Pale yellowish crystal Melting point: 222–223° C. |
| 9-13 | 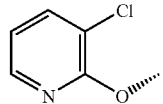 | H | Free form | Crystal Melting point: 91–94° C. MS # APCI (m/z): 229, 227 |
| 9-14 | 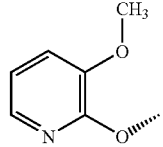 | H | Free form | Powder MS # APCI (m/z): 229, 227 |
| 9-15 |  | H | Free form | Powder MS # APCI (m/z): 223 |

TABLE 6-continued

| Reference Example No. | R²—X— | R¹ | Salt | Physical properties, etc. |
|---|---|---|---|---|
| 9-16 | (pyridin-2-yloxy) | H | Free form | Powder MS # APCI (m/z): 193 |
| 9-17 | (5-chloropyridin-2-yloxy) | H | Free form | Powder MS # APCI (m/z): 229, 227 |
| 9-18 | (6-methoxypyridin-2-yloxy, NH) | H | | |
| 9-19 | (pyrimidin-4-yloxy) | H | Free form | Oil |
| 9-20 | (6-chloropyrazin-2-yloxy) | H | | |
| 9-21 | (3-cyanopyrazin-2-yloxy) | H | | |
| 9-22 | (2-methylthiopyrimidin-4-yloxy) | H | Free form | Colorless powder MS # APCI (m/z): 240 (M + H+)+ |
| 9-23 | (4-trifluoromethylpyrimidin-2-yloxy) | H | | |
| 9-24 | (5-ethylpyrimidin-2-yloxy) | H | Free form | Powder MS # APCI (m/z): 222 |
| 9-25 | (3-cyanopyrazin-2-yloxy) | H | Free form | Oil |
| 9-26 | (6-chloropyridazin-3-yloxy) | H | Free form | Powder MS # APCI (m/z): 262, 260 |

TABLE 6-continued

| Reference Example No. | R²—X— | R¹ | Salt | Physical properties, etc. |
|---|---|---|---|---|
| 9-27 | pyridazin-3-yloxy | H | Free form | Powder<br>MS # APCI (m/z): 194 |
| 9-28 | N,N-diisopropyl-2-(oxy)nicotinamide | H | Free form | Oil<br>MS # APCI (m/z): 320 |
| 9-29 | 5-bromo-4-(thiophen-2-yl)pyrimidin-2-yloxy | H | Free form | Powder<br>MS # APCI (m/z): 356, 354 |
| 9-30 | 6-phenylpyridazin-3-yloxy | H | Free form | Powder<br>MS # APCI (m/z): 270 |
| 9-31 | quinolin-2-yloxy | H | Free form | Powder<br>MS # APCI (m/z): 243 |
| 9-32 | benzothiazol-2-yloxy | H | Free form | Oil |
| 9-33 | 2-nitrophenoxy | H | Free form | Powder<br>MS # APCI (m/z): 237 |
| 9-34 | 2-cyanophenoxy | H | HCl | Colorless crystal<br>Melting point:<br>215–218° C.<br>MS # APCI (m/z): 217 [M + H] |
| 9-35 | 2-cyano-3-fluorophenoxy | H | Free form | Yellowish oil |

TABLE 6-continued

R²—X—[cyclohexane]—R¹, NH₂

| Reference Example No. | R²—X— | R¹ | Salt | Physical properties, etc. |
|---|---|---|---|---|
| 9-36 | 3-fluoro-2-cyanophenyl (2-F, 6-CN phenoxy) | H | Free form | Yellowish oil |
| 9-37 | 3-(trifluoromethyl)-2-cyanophenoxy | H | Free form | Yellowish oil |
| 9-38 | 4-cyano-3-fluorophenoxy | H | Free form | Colorless oil |
| 9-39 | 2-cyano-4-fluorophenoxy | H | Free form | Colorless oil |
| 9-40 | 2-cyano-4-methylphenoxy | H | HCl | Colorless crystal<br>Melting point: 253–254° C.<br>MS # APCI (m/z): 231 [M + H] |
| 9-41 | 2-cyano-4-fluorophenoxy | H | HCl | Pale green<br>melting point: 270–285° C.<br>MS # APCI (m/z): 235 [M + H] |
| 9-42 | 2-cyano-4-bromophenoxy | H | HCl | Colorless crystal<br>melting point: 283–284° C.<br>MS # APCI (m/z): 297, 295 [M + H] |
| 9-43 | 2-cyano-3-methoxyphenoxy | H | HCl | Colorless crystal<br>melting point: 246–247° C.<br>MS # APCI (m/z): 247 [M + H] |
| 9-44 | 3-chloro-2-cyanophenoxy | H | HCl | Colorless crystal<br>melting point: 285–294° C.<br>MS # APCI (m/z): 251 [M + H] |

TABLE 6-continued

| Reference Example No. | R²—X— | R¹ | Salt | Physical properties, etc. |
|---|---|---|---|---|
| 9-45 | 4-bromo-2-(oxy)-benzonitrile | H | HCl | Colorless crystal melting point: >300° C. MS # APCI (m/z): 297, 295 [M + H] |
| 9-46 | pyrimidin-2-yloxy | H | Free form | Pale brownish semi-solid MS # APCI (m/z): 194 [M + H] IR(cm⁻¹): 3351 |
| 9-47 | 4-nitrophenoxy | H | HCl | Yellow brownish crystal melting point: 238–240° C. |
| 9-48 | 3-amino-pyridin-2-yloxy | H | HCl | Pale brownish crystal melting point: 180° C. (decomposed) |
| 9-49 | ethyl 2-(methylthio)-4-(oxy)pyrimidine-5-carboxylate | H | Free form | |
| 9-50 | ethyl 2-(dimethylsulfonio)-4-(oxy)pyrimidine-5-carboxylate | H | Free form | |
| 9-51 | ethyl 2-(methylamino)-4-(oxy)pyrimidine-5-carboxylate | H | Free form | |

TABLE 6-continued

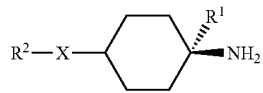

| Reference Example No. | R²—X— | R¹ | Salt | Physical properties, etc. |
|---|---|---|---|---|
| 9-52 | ethyl 2-morpholino-4-(oxy)pyrimidine-5-carboxylate group | H | | Free form |
| 9-53 | ethyl 4-pyrrolidinyl-2-(oxy)benzoate group | H | | Free form |
| 9-54 | ethyl 2-amino-4-(oxy)pyrimidine-5-carboxylate group | H | | Free form |
| 9-55 | 2-(dimethylamino)-N,N-dimethyl-4-(oxy)pyrimidine-5-carboxamide group | H | | Free form |
| 9-56 | 2-(dimethylamino)-4-(oxy)-5-(morpholine-4-carbonyl)pyrimidine group | H | | Free form |

TABLE 6-continued

| Reference Example No. | R²—X— | R¹ | Salt | Physical properties, etc. |
|---|---|---|---|---|
| 9-57 | [2-(dimethylamino)-4-methoxy-5-(pyrrolidine-1-carbonyl)pyrimidine] | H | Free form | |
| 9-58 | 5-nitro-2-pyridyloxy | H | HCl | Pale brownish powder<br>MS # APCI (m/z): 238 [M + H]+ |
| 9-59 | 5-cyano-2-pyridyloxy | H | HCl | Colorless powder<br>MS # APCI (m/z): 218 [M + H]+ |
| 9-60 | 5-trifluoromethyl-2-pyridyloxy | H | HCl | Colorless crystal<br>melting point: 234–235° C. (decomposed) |
| 9-61 | 3-cyano-2-pyridyloxy | H | HCl | Colorless crystal<br>melting point: 126° C. |
| 9-62 | 5-bromo-2-pyrimidinyloxy | H | HCl | Pale yellowish crystal<br>melting point: 206–207° C. (decomposed) |
| 9-63 | 5-methylthio-2-pyrimidinyloxy | H | HCl | Pale yellowish crystal<br>melting point: 148–150° C. (decomposed) |
| 9-64 | 2-pyrazinyloxy | H | HCl | Colorless crystal<br>melting point: 189–191° C. (decomposed) |
| 10-2 | 3-nitro-2-pyridyloxy | Me | Free form | Colorless liquid<br>MS # APCI (m/z): 252 [M + H]+ |
| 10-3 | 5-cyano-2-pyridyloxy | Me | Free form | Colorless crystal<br>Melting point: 73–76° C. |

TABLE 6-continued

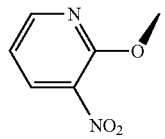

| Reference Example No. | R²—X— | R¹ | Salt | Physical properties, etc. |
|---|---|---|---|---|
| 10-4 | 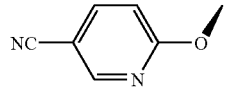 | Me | Free form | Colorless liquid<br>MS.AFCI(m/z):<br>252 [M + H]+ |
| 10-5 | 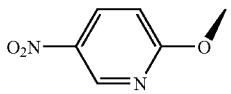 | Me | Free form | Colorless crystal<br>Melting point:<br>88–89° C. |
| 10-6 | 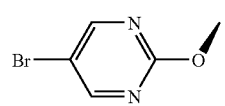 | Me | Free form | Colorless crystal<br>Melting point:<br>90–94° C. |
| 10-7 | 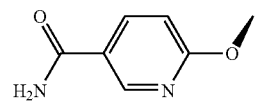 | Me | Free form | Colorless crystal<br>Melting point:<br>97–100° C. |
| 10-8 | 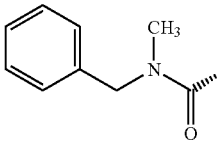 | Me | Free form | Colorless crystal<br>Melting point:<br>150–154° C. |

TABLE 7

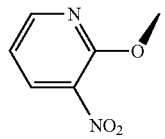

| Reference Example No. | R²—X— | R¹ | Salt | Physical properties, etc. |
|---|---|---|---|---|
| 11-1 | 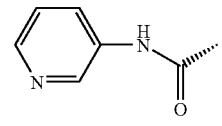 | H | HCl | Colorless solid<br>Melting point:<br>150–153° C.<br>MS # APCI (m/z): 247<br>[M + H]+ |
| 11-2 | 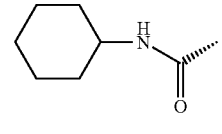 | H | 2HCl | Colorless crystal<br>Melting point: 294–295° C. |
| 11-3 | 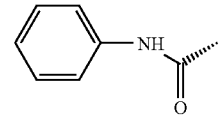 | H | Free form | Colorless crystal<br>Melting point:<br>185.5–186° C. |
| 11-4 | 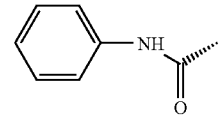 | H | HCl | Colorless solid<br>Melting point: >300° C.<br>MS # APCI (m/z): 219<br>[M + H]+ |

TABLE 7-continued

R²—X—[cyclohexane]—R¹, NH₂

| Reference Example No. | R²—X— | R¹ | Salt | Physical properties, etc. |
|---|---|---|---|---|
| 11-5 | piperidine-N-NH-C(=O)- | H | Free form | Colorless solid<br>Melting point:<br>163–166° C. |
| 11-6 | cyclohexyl-N(CH₃)-C(=O)- | H | Free form | Colorless liquid<br>MS # APCI (m/z): 239<br>[M + H] |
| 11-7 | 2-pyridyl-CH₂CH₂-N(CH₃)-C(=O)- | H | Free form | Colorless liquid<br>MS # APCI (m/z): 262<br>[M + H] |
| 11-8 | piperidine-N-CH₂CH₂-N(CH₃)-C(=O)- | H | Free form | Colorless liquid |
| 11-9 | 3,4-methylenedioxybenzyl-N(CH₃)-C(=O)- | H | Free form | Colorless liquid |
| 11-10 | (H₃C)₂N-C(=O)- | H | Free form | Liquid<br>MS # APCI (m/z): 171<br>[M + H] |
| 11-11 | H₃C-CH₂CH₂CH₂-N(CH₃)-C(=O)- | H | Free form | Pale yellowish oil<br>MS # APCI (m/z): 213 |
| 11-12 | H₃C-(CH₂)₄-N(CH₃)-C(=O)- | H | Free form | Colorless oil<br>MS # APCI (m/z): 241<br>[M + H]+ |
| 11-13 | (H₃C)₃C-N(CH₂CH₃)-C(=O)- | H | Free form | Pale yellowish oil<br>MS # APCI (m/z): 213 |

TABLE 7-continued

Structure: R²—X—[cyclohexane]—R¹, NH₂

| Reference Example No. | R²—X— | R¹ | Salt | Physical properties, etc. |
|---|---|---|---|---|
| 11-14 | H₃C-CH₂-N(CH₂-CH₃)-C(=O)- (N,N-dipropyl amide) | H | HCl | Colorless liquid<br>MS # APCI (m/z): 227[M + H]+ |
| 11-15 | H₃C-N(CH₂CH₂-O-CH₃)-C(=O)- | H | Free form | Pale yellowish oil<br>MS # APCI (m/z): 229 |
| 11-16 | H₃C-N(cyclohexyl)-C(=O)- | H | Free form | Colorless oil<br>MS # APCI (m/z): 253 [M + H]+ |
| 11-17 | H₂N-C(=O)- | H | HI | Colorless powder<br>MS # APCI (m/z): 143[M + H]+ |
| 11-18 | H₃C-NH-C(=O)- | H | Free form | Colorless crystal<br>MS # APCI (m/z): 157 |
| 11-19 | H₃C-CH₂-NH-C(=O)- | H | Free form | Colorless crystal<br>MS # APCI (m/z): 171 |
| 11-20 | H₃C-CH₂-CH₂-CH₂-NH-C(=O)- | H | Free form | Colorless crystal<br>MS # APCI (m/z): 199 |
| 11-21 | (H₃C)(CH₃)CH-NH-C(=O)- | H | Free form | Colorless crystal<br>MS # APCI (m/z): 185 |
| 11-22 | (H₃C)(H₃C)(CH₃)C-NH-C(=O)- | H | Free form | Colorless crystal<br>Melting point: 142° C. (Decomposed)<br>MS # APCI (m/z): 199[M + H]+ |
| 11-23 | (H₃C)(H₃C-CH₂)N-C(=O)- | H | Free form | Colorless oil<br>MS # APCI (m/z): 185 |
| 11-24 | (H₃C)(H₃C-CH₂-CH₂)N-C(=O)- | H | Free form | Colorless oil<br>MS # APCI (m/z): 199 |

TABLE 7-continued

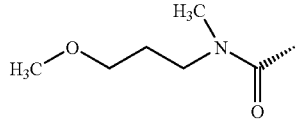

| Reference Example No. | R²—X— | R¹ | Salt | Physical properties, etc. |
|---|---|---|---|---|
| 11-25 | 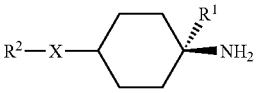 | H | Free form | Colorless resin<br>MS # APCI (m/z): 229 [M + H]+ |
| 11-26 | 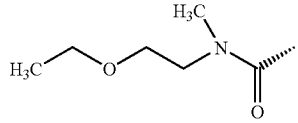 | H | Free form | Colorless resin<br>MS # APCI (m/z): 229 [M + H]+ |
| 11-27 | 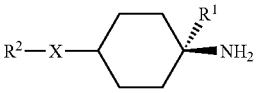 | H | Free form | Colorless resin<br>MS # APCI (m/z): 243 [M + H]+ |
| 11-28 | 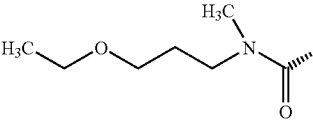 | H | Free form | Colorless oil<br>MS # APCI (m/z): 215 |
| 11-29 | 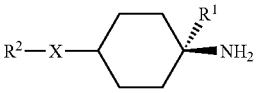 | H | Free form | Colorless oil<br>MS # APCI (m/z): 215 |
| 11-30 | 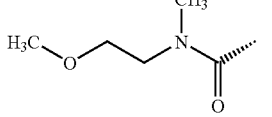 | H | Free form | Colorless resin<br>MS # APCI (m/z): 229 [M + H]+ |
| 11-31 | 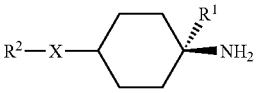 | H | Free form | Colorless resin<br>MS # APCI (m/z): 271 [M + H]+ |
| 11-32 | 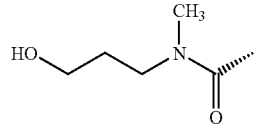 | H | Free form | Colorless resin<br>MS # APCI (m/z): 243 [M + H]+ |
| 11-33 | 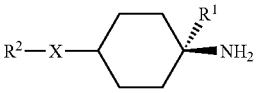 | H | Free form | Colorless resin<br>MS # APCI (m/z): 197 [M + H]+ |
| 11-34 | 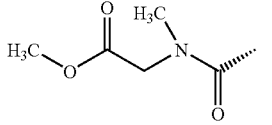 | H | Free form | Pale brownish resin |

TABLE 7-continued

R²—X—[cyclohexane]—R¹, NH₂

| Reference Example No. | R²—X— | R¹ | Salt | Physical properties, etc. |
|---|---|---|---|---|
| 11-35 | [6-methoxy-pyridin-2-yl with N(CH₃)C(O)–] | H | Free form | Pale brownish resin |
| 11-36 | [indan-2-yl with N(CH₃)C(O)–] | H | Free form | Pale brownish resin |
| 11-37 | [indan-2-yl with N(CH₂CH₃)C(O)–] | H | Free form | Pale brownish resin |
| 11-38 | [indan-2-yl with NHC(O)–] | H | Free form | Pale brownish resin |

TABLE 8

R²—X—[cyclohexane]—R¹, NH₂

| Reference Example No. | R²—X— | R¹ | Salt | Physical properties, etc. |
|---|---|---|---|---|
| 12-1 | pyrrolidin-1-yl-C(O)– | H | Free form | Colorless oil<br>MS # APCI (m/z): 197 [M + H]+ |
| 12-2 | 2-(hydroxymethyl)pyrrolidin-1-yl-C(O)– | H | Free form | Colorless liquid |
| 12-3 | 2-(methoxymethyl)pyrrolidin-1-yl-C(O)– | H | Free form | Pale yellowish oil<br>MS # APCI (m/z): 241 |
| 12-4 | azepan-1-yl-C(O)– | H | Free form | Colorless oil<br>MS # APCI (m/z): 225 [M + H]+ |

TABLE 8-continued

R²—X— [cyclohexane with R¹ and NH₂]

| Reference Example No. | R²—X— | R¹ | Salt | Physical properties, etc. |
|---|---|---|---|---|
| 12-5 | piperidine-N-C(O)- | H | Free form | Colorless oil<br>MS # APCI (m/z): 211 [M + H]+ |
| 12-6 | 4-methylpiperidine-N-C(O)- | H | Free form | Colorless oil<br>MS # APCI (m/z): 225 [M + H]+ |
| 12-7 | 3,3-dimethylpiperidine-N-C(O)- | H | Free form | Colorless oil<br>MS # APCI (m/z): 239 [M + H]+ |
| 12-8 | 4-tert-butylpiperidine-N-C(O)- | H | Free form | Colorless liquid<br>MS # APCI (m/z): 267 [M + H]+ |
| 12-9 | 4-(methoxycarbonyl)piperidine-N-C(O)- | H | Free form | Colorless liquid<br>MS # APCI (m/z): 269 [M + H]+ |
| 12-10 | 3-(carbamoyl)piperidine-N-C(O)- | H | Free form | Colorless oil<br>MS # APCI (m/z): 254 |
| 12-11 | 4-(carbamoyl)piperidine-N-C(O)- | H | HCl | Colorless oil<br>MS # APCI (m/z): 254 [M + H]+ |
| 12-12 | 4-(dimethylamino)piperidine-N-C(O)- | H | 2HCl | Colorless powder<br>MS # APCI (m/z): 254 [M + H]+ |
| 12-13 | 4-(N,N-diethylcarbamoyl)piperidine-N-C(O)- | H | HCl | Colorless resin<br>MS # APCI (m/z): 310 [M + H]+ |
| 12-14 | 4-ethylpiperazine-N-C(O)- | H | Free form | Colorless solid<br>MS # APCI (m/z): 240 |
| 12-15 | 4-isopropylpiperazine-N-C(O)- | H | 2HCl | Colorless powder<br>MS # APCI (m/z): 254 [M + H]+ |

TABLE 8-continued

| Reference Example No. | R²—X— | R¹ | Salt | Physical properties, etc. |
|---|---|---|---|---|
| 12-16 | H₃C-CH₂CH₂CH₂-N(piperazine)- | H | 2HCl | Colorless powder<br>MS # APCI (m/z): 268 [M + H]+ |
| 12-17 | HO-CH₂CH₂-N(piperazine)-C(=O)- | H | 2HCl | Colorless powder<br>MS # APCI (m/z): 256 [M + H]+ |
| 12-18 | CH₃-C(=O)-N(piperazine)-C(=O)- | H | Free form | Colorless powder<br>MS # APCI (m/z): 254 [M + H] |
| 12-19 | CH₃CH₂-C(=O)-N(piperazine)-C(=O)- | H | Free form | Colorless solid<br>Melting point: 93–96° C. |
| 12-20 | (CH₃)₂CH-C(=O)-N(piperazine)-C(=O)- | H | Free form | Colorless solid<br>Melting point: 242–245° C. |
| 12-21 | CH₃-C(=O)-N(2,6-dimethylpiperazine)-C(=O)- | H | Free form | Colorless liquid<br>MS # APCI (m/z): 282 [M + H] |
| 12-22 | (CH₃)₃C-C(=O)-N(piperazine)-C(=O)- | H | Free form | Colorless solid<br>Melting point: 173–176° C. |
| 12-23 | (CH₃)₂CH-CH₂-C(=O)-N(piperazine)-C(=O)- | H | Free form | Colorless solid<br>Melting point: 135–137° C. |
| 12-24 | CH₃CH₂-O-C(=O)-N(piperazine)-C(=O)- | H | Free form | Colorless crystal<br>Melting point: 90–92° C. |
| 12-25 | CH₃-S(=O)₂-N(piperazine)-C(=O)- | H | Free form | Colorless crystal<br>Melting point: 152–153° C. |

TABLE 8-continued

R²—X—[cyclohexane]—R¹, NH₂

| Reference Example No. | R²—X— | R¹ | Salt | Physical properties, etc. |
|---|---|---|---|---|
| 12-26 | 2,6-dimethylmorpholine-N-C(O)— | H | Free form | Colorless liquid<br>MS # APCI (m/z): 241 [M + H] |
| 12-27 | morpholine-N-C(O)— | H | Free form | Colorless crystal<br>Melting point: 75–80° C. |
| 12-28 | isoindoline-N-C(O)— | H | Free form | Colorless crystal<br>Melting point: 170–173° C. |
| 12-29 | 5-nitroisoindoline-N-C(O)— | H | Free form | Colorless oil<br>MS # APCI (m/z): 290 [M + H]+ |
| 12-30 | indoline-N-C(O)— | H | HCl | Pale brownish solid<br>Melting point: 230–233° C. |
| 12-31 | 6,7-dihydro-5H-pyrrolo[3,4-b]pyridine-N-C(O)— | H | 2HCl | Pale yellowish solid<br>MS # APCI (m/z): 246 [M + H]+ |
| 12-32 | 1,2,3,4-tetrahydroisoquinoline-N-C(O)— | H | Free form | Colorless solid<br>Melting point: 150–155° C. |
| 12-33 | 4,5,6,7-tetrahydrothieno[3,2-c]pyridine-N-C(O)— | H | Free form | Colorless solid<br>Melting point: 65–69° C. |
| 12-34 | 4-phenylpiperidine-N-C(O)— | H | Free form | Colorless solid<br>Melting point: 166–170° C. |
| 12-35 | 4-(thiophen-2-yl)piperidine-N-C(O)— | H | Free form | Colorless oil<br>MS # APCI (m/z): 293 [M + H]+ |
| 12-36 | 4-(4-methoxyphenyl)-3,6-dihydro-2H-pyridine-N-C(O)— | H | Free form | Colorless powder<br>MS # APCI (m/z): 315 [M + H]+ |

TABLE 8-continued

| Reference Example No. | R²—X— | R¹ | Salt | Physical properties, etc. |
|---|---|---|---|---|
| 12-37 | (phenyl-piperazine-C(O)-) | H | Free form | Colorless solid<br>Melting point: 185–189° C. |
| 12-38 | (2-methylphenyl-piperazine-C(O)-) | H | Free form | Colorless liquid<br>MS # APCI (m/z): 302 [M + H] |
| 12-39 | (4-chlorophenyl-piperazine-C(O)-) | H | Free form | Colorless crystal<br>Melting point: 131–132° C. |
| 12-40 | (4-methoxyphenyl-piperazine-C(O)-) | H | Free form | Colorless solid<br>Melting point: 81–83° C. |
| 12-41 | (2-pyridyl-piperazine-C(O)-) | H | Free form | Colorless solid<br>Melting point: 185–189° C. |
| 12-42 | (2-pyrimidinyl-piperazine-C(O)-) | H | 2HCl | Colorless powder<br>MS # APCI (m/z): 290 [M + H]+ |
| 12-43 | (1,3-dioxoindan-2-yl-piperidine-C(O)-) | H | HCl | Colorless solid<br>MS # APCI (m/z): 356 [M + H]+ |
| 12-44 | (cyclohexylmethyl-piperazine-C(O)-) | H | Free form | Colorless crystal<br>Melting point: 59–60° C. |
| 12-45 | (benzyl-piperazine-C(O)-) | H | Free form | Colorless liquid<br>MS # APCI (m/z): 302 |
| 12-46 | (benzyl-2,6-dimethylpiperazine-C(O)-) | H | Free form | Colorless liquid<br>MS # APCI (m/z): 330 [M + H] |
| 12-47 | (4-benzylpiperidine-C(O)-) | H | Free form | Colorless powder<br>MS # APCI (m/z): 301 |

TABLE 8-continued

| Reference Example No. | R²—X— | R¹ | Salt | Physical properties, etc. |
|---|---|---|---|---|
| 12-48 | 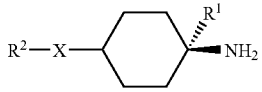 | H | Free form | Colorless liquid<br>MS # APCI (m/z): 358 |
| 12-49 | 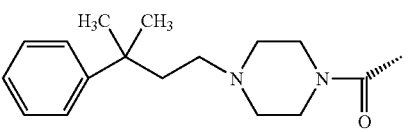 | H | Free form | Colorless crystal<br>Melting point:<br>120–121° C. |
| 12-50 | 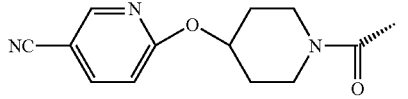 | H | Free form | Pale yellowish crystal<br>Melting point:<br>119–120° C. |
| 12-51 | 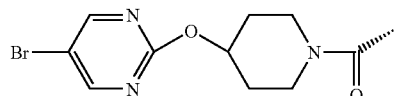 | H | Free form | Colorless crystal<br>Melting point:<br>144–145° C. |
| 12-52 | 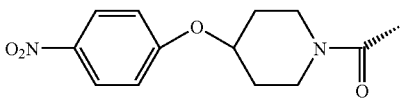 | H | Free form | Yellowish crystal<br>Melting point:<br>140–141° C. |
| 12-53 | 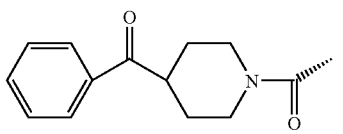 | H | Free form | Colorless crystal<br>Melting point:<br>110–111° C. |
| 12-54 | 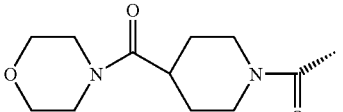 | H | HCl | Colorless crystal<br>Melting point: 97–° C.<br>MS # APCI (m/z): 324<br>[M + H]+ |
| 12-55 | 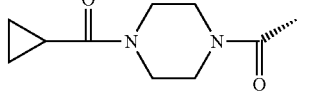 | H | Free form | Colorless solid<br>Melting point:<br>245–248° C. |
| 12-56 | 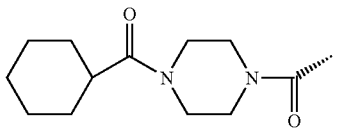 | H | Free form | Colorless solid<br>Melting point:<br>202–205° C. |
| 12-57 | 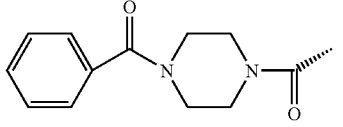 | H | Free form | Colorless crystal<br>Melting point:<br>150–153° C. |

TABLE 8-continued

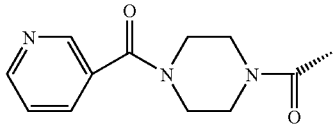

| Reference Example No. | R²—X— | R¹ | Salt | Physical properties, etc. |
|---|---|---|---|---|
| 12-58 | 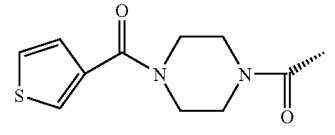 | H | Free form | Colorless liquid MS # APCI (m/z): 317 [M + H] |
| 12-59 | 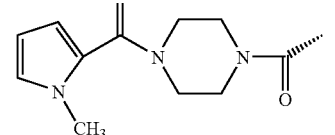 | H | Free form | Colorless crystal Melting point: 158–162° C. |
| 12-60 | 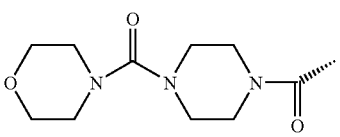 | H | Free form | Colorless liquid MS # APCI (m/z): 319 [M + H] |
| 12-61 | 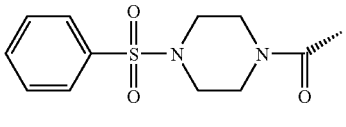 | H | HCl | Colorless powder MS # APCI (m/z): 325 [M + H]+ |
| 12-62 | 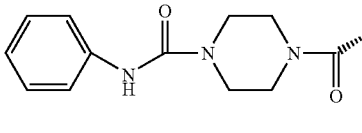 | H | Free form | Colorless crystal Melting point: 148–150° C. |
| 12-63 | 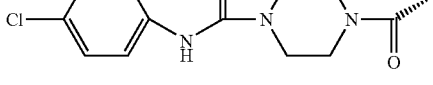 | H | Free form | Colorless powder MS # APCI (m/z): 331 [M + H]+ |
| 12-64 | 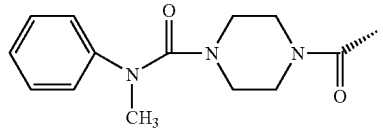 | H | Free form | Colorless resin MS # APCI (m/z): 364 [M + H]+ |
| 12-65 | 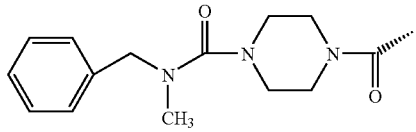 | H | Free form | Colorless oil MS # APCI (m/z): 345 [M + H]+ |
| 12-66 | 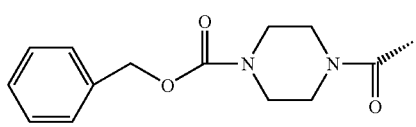 | H | Free form | Colorless oil MS # APCI (m/z): 358 [M + H]+ |
| 12-67 | | H | Free form | Colorless crystal Melting point: 70° C. |

TABLE 8-continued

| Reference Example No. | R²—X— | R¹ | Salt | Physical properties, etc. |
|---|---|---|---|---|
| 12-68 | 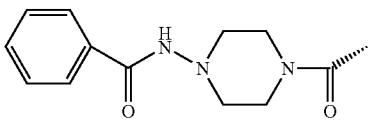 | H | Free form | Colorless crystal Melting point: 188–190° C. |
| 12-69 | 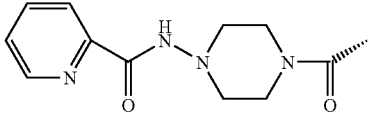 | H | 2HCl | Colorless crystal Melting point: 180° C. (Decomposed) MS # APCI (m/z): 331 [M + H]+ |
| 12-70 | 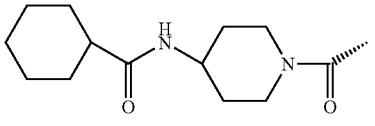 | H | Free form | SligHtly brownish crystal Melting point: 214–216° C. |
| 12-71 | 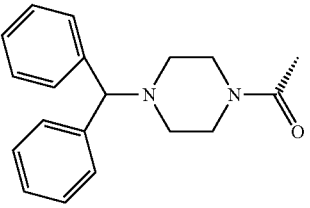 | H | Free form | Colorless liquid MS # APCI (m/z): 378 [M + H]+ |
| 12-72 | 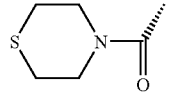 | H | HCl | Colorless powder MS # APCI (m/z): 229 [M + H]+ |
| 12-73 | 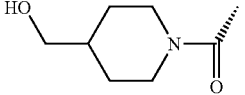 | H | Free form | Colorless oil MS # APCI (m/z): 241 |
| 12-74 | 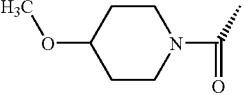 | H | Free form | Colorless crystal MS # APCI (m/z): 241 |
| 12-75 | 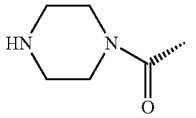 | H | Free form | |
| 12-76 | 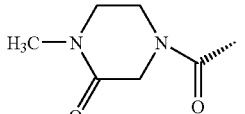 | H | Free form | Colorless oil MS # APCI (m/z): 240 |
| 12-77 | 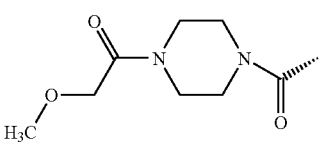 | H | Free form | Colorless powder MS # APCI (m/z): 284 [M + H]+ |

TABLE 8-continued

| Reference Example No. | R²—X— | R¹ | Salt | Physical properties, etc. |
|---|---|---|---|---|
| 12-78 | (4-(dimethylcarbamoyl)piperazin-1-yl)carbonyl- | H | Free form | Pale yellowish crystal Melting point: 99–104° C. MS # APCI (m/z): 283[M + H]+ |
| 12-79 | 4-(ethoxycarbonyl)phenoxymethyl-(1-acetylpiperidin-4-yl) | H | Free form | Colorless resin MS # APCI (m/z): 389 [M + H]+ |
| 12-80 | 4-(3-methoxyphenyl)-1-acetylpiperidin-4-yl | H | Free form | Colorless resin MS # APCI (m/z): 317 [M + H]+ |
| 12-81 | 4-methoxy-2-acetylisoindolin-yl | H | Free form | Colorless powder MS # APCI (m/z): 275 [M + H]+ |
| 12-82 | 5-amino-2-acetylisoindolin-yl | H | Free form | Colorless foam |
| 12-83 | 5-(2-(dimethylamino)acetamido)-2-acetylisoindolin-yl | H | Free form | Pale brownish resin |
| 12-84 | 5-(methanesulfonamido)-2-acetylisoindolin-yl | H | Free form | Pale brownish resin |
| 12-85 | 5-(hydroxymethyl)-2-acetylisoindolin-yl | H | Free form | Pale brownish resin |
| 12-86 | 5-methoxy-2-acetylisoindolin-yl | H | Free form | Colorless powder MS # APCI (m/z): 275 [M + H]+ |
| 12-87 | 5-ethoxy-2-acetylisoindolin-yl | H | Free form | Colorless powder MS # APCI (m/z): 289 [M + H]+ |

TABLE 8-continued

| Reference Example No. | R²—X— | R¹ | Salt | Physical properties, etc. |
|---|---|---|---|---|
| 12-88 | (6-hydroxyisoindolin-2-yl)carbonyl | H | HCl | Colorless solid<br>MS # APCI (m/z): 261 [M + H]+ |
| 12-89 | (5-sulfamoylisoindolin-2-yl)carbonyl | H | HCl | Colorless solid<br>Melting point: 277–279° C.<br>MS # APCI (m/z): 324 [M + H]+ |
| 12-90 | (8-methoxy-3,4-dihydroisoquinolin-2(1H)-yl)carbonyl | H | HCl | Colorless solid<br>MS # APCI (m/z): 289 [M + H]+ |
| 12-91 | (3-oxo-3,4-dihydroquinoxalin-1(2H)-yl)carbonyl | H | Free form | Colorless crystal<br>MS # APCI (m/z): 274 |
| 12-92 | (5-(ethoxymethyl)isoindolin-2-yl)carbonyl | H | Free form | Pale brownish resin |
| 12-93 | (5-(methoxymethyl)isoindolin-2-yl)carbonyl | H | Free form | Pale brownish resin |
| 12-94 | (5-(isopropoxymethyl)isoindolin-2-yl)carbonyl | H | Free form | Pale brownish resin |
| 12-95 | (5-(methoxycarbonylamino)isoindolin-2-yl)carbonyl | H | Free form | Pale brownish resin |
| 12-96 | (5-acetamidoisoindolin-2-yl)carbonyl | H | Free form | Pale brownish resin |
| 12-97 | (1,1-dioxothiomorpholin-4-yl)carbonyl | H | Free form | Colorless crystal<br>Melting point: 152–153° C. |

TABLE 8-continued

| Reference Example No. | R²—X— | R¹ | Salt | Physical properties, etc. |
|---|---|---|---|---|
| 13-1 | pyrimidin-2-yl-NH-C(=O)- | H | Free form | Brownish oil MS # APCI (m/z): 221 [M + H]+ |
| 13-2 | pyrazin-2-yl-NH-C(=O)- | H | Free form | Pale yellowish powder MS # APCI (m/z): 221 [M + H]+ |
| 13-3 | 1-ethyl-1H-pyrazol-5-yl-NH-C(=O)- | H | Free form | Pale yellowish oil MS # APCI (m/z): 237 [M + H]+ |
| 13-4 | thiazol-2-yl-NH-C(=O)- | H | Free form | Brownish powder MS # APCI (m/z): 226 [M + H]+ |
| 13-5 | 4-methylthiazol-2-yl-NH-C(=O)- | H | Free form | Brownish oil MS # APCI (m/z): 240 [M + H]+ |
| 13-6 | 1,3,4-thiadiazol-2-yl-NH-C(=O)- | H | Free form | Brownish oil MS # APCI (m/z): 227 [M + H]+ |
| 13-7 | 5-hydroxyindolin-1-yl-C(=O)- | H | HBr | Pale brownish powder MS # APCI (m/z): 261 [M + H]+ |
| 13-8 | phenyl-C(=O)- | H | HI | Yellowish powder MS # APCI (m/z): 204 [M + H] |
| 13-9 | 4-cyanophenyl-C(=O)- | H | HI | Yellowish powder MS # APCI (m/z): 229 [M + H] |
| 13-10 | 4-chlorophenyl-C(=O)- | H | HI | Yellowish powder MS # APCI (m/z): 238 [M + H] |

TABLE 8-continued

R²—X—[cyclohexane]—R¹, NH₂

| Reference Example No. | R²—X— | R¹ | Salt | Physical properties, etc. |
|---|---|---|---|---|
| 13-11 | 2-nitrophenyl-C(=O)– | H | Free form | Yellowish powder MS # APCI (m/z): 249 [M + H] |
| 13-12 | 4-isopropylphenyl-C(=O)– | H | Free form | Yellowish powder MS # APCI (m/z): 246 [M + H] |
| 13-13 | furan-3-yl-C(=O)– | H | HI | Yellowish powder MS # APCI (m/z): 194 [M + H] |
| 13-14 | thiophen-3-yl-C(=O)– | H | HI | Yellowish powder MS # APCI (m/z): 210 [M + H] |
| 13-15 | benzothiophen-2-yl-C(=O)– | H | HI | Yellowish powder MS # APCI (m/z): 260 [M + H] |
| 13-16 | pyridin-3-yl-C(=O)– | H | 2HI | Yellowish powder MS # APCI (m/z): 205 [M + H] |
| 13-17 | morpholin-4-yl-C(=O)– | Me | HI | Yellowish powder MS # APCI (m/z): 227 [M + H] |
| 13-18 | 4-(methoxycarbonyl)piperazin-1-yl-C(=O)– | H | Free form | Colorless semi-solid MS # APCI (m/z): 270 [M + H] |
| 13-19 | 4-(butoxycarbonyl)piperazin-1-yl-C(=O)– | H | Free form | Colorless semi-solid MS # APCI (m/z): 312 [M + H] |

TABLE 8-continued

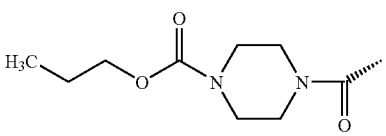

| Reference Example No. | R²—X— | R¹ | Salt | Physical properties, etc. |
|---|---|---|---|---|
| 13-20 | 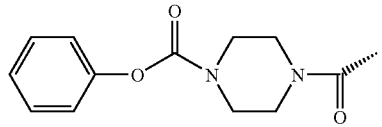 | H | Free form | Colorless resin<br>MS # APCI (m/z): 298 [M + H] |
| 13-21 | 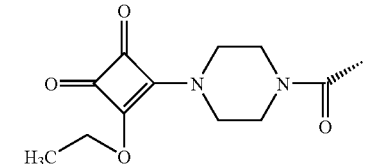 | H | Free form | Colorless oil<br>MS # APCI (m/z): 332 [M + H] |
| 13-22 | 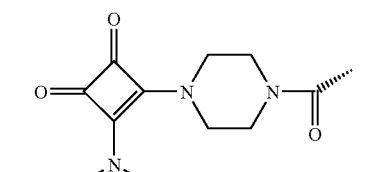 | H | HCl | Colorless powder<br>Melting point: >300° C.<br>MS # APCI (m/z): 336 [M + H] |
| 13-23 | 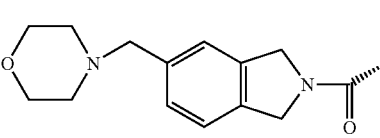 | H | HI | Brownish powder |
| 13-24 | 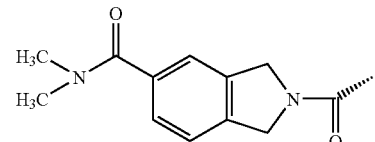 | H | Free form | Pale brownish resin |
| 13-25 | 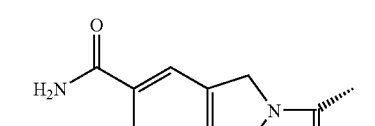 | H | Free form | Pale brownish resin |
| 13-26 | 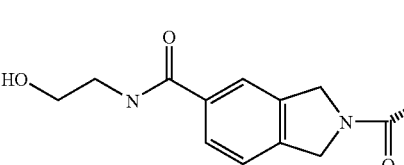 | H | Free form | Pale brownish resin |
| 13-27 |  | H | Free form | Pale brownish resin |

TABLE 8-continued
| Reference Example No. | R²—X— | R¹ | Salt | Physical properties, etc. |
|---|---|---|---|---|
| 13-28 | 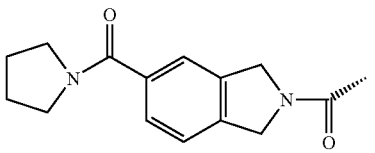 | H | Free form | Pale brownish resin |
| 13-29 | 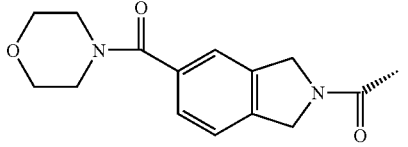 | H | Free form | Pale brownish resin |
| 13-30 | 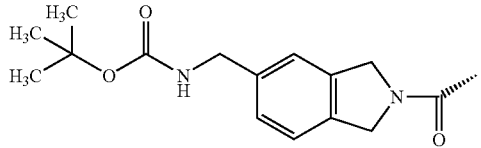 | H | Free form | Pale brownish resin |
| 13-31 | 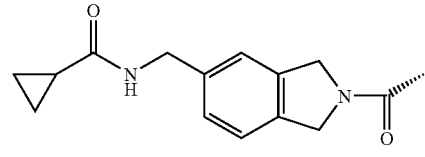 | H | Free form | Colorless powder<br>MS # APCI (m/z): 342 [M + H]+ |
| 13-32 | 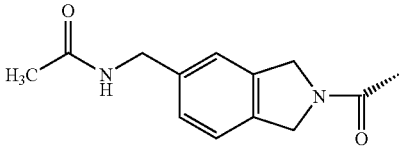 | H | HI | Colorless powder<br>MS # APCI (m/z): 315 [M + H]+ |
| 13-33 | 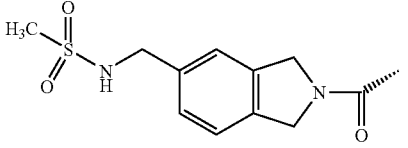 | H | HI | Colorless powder<br>MS # APCI (m/z): 352 [M + H]+ |
| 13-34 | 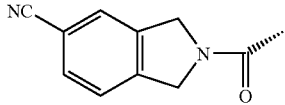 | H | HI | Pale brownish powder |
| 13-35 | 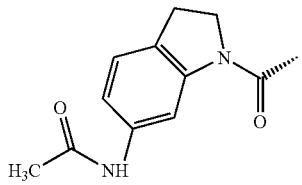 | H | Free form | Brownish oil |

TABLE 8-continued

| Reference Example No. | R²—X— | R¹ | Salt | Physical properties, etc. |
|---|---|---|---|---|
| 13-36 | (1-acetylindolin-6-yl)-NH-C(O)-N(CH₃)₂ | H | Free form | Brownish oil |
| 13-37 | (1-acetylindolin-6-yl)-NH-C(O)-OCH₃ | H | Free form | Brownish oil |
| 13-38 | (1-acetylindolin-6-yl)-NH-S(O)₂-CH₃ | H | Free form | Brownish oil |
| 13-39 | (1-acetylindolin-6-yl)-NH-C(O)-CH₂-N(CH₃)₂ | H | Free form | Brownish oil |
| 13-40 | (1-acetylindolin-6-yl)-N(CH₃)₂ | H | Free form | Brownish oil |
| 13-41 | (1-acetylindolin-5-yl)-NH-C(O)-CH₃ | H | Free form | |
| 13-42 | (1-acetylindolin-5-yl)-NH-C(O)-N(CH₃)₂ | H | HI | Brownish powder |

TABLE 8-continued

| Reference Example No. | R²—X— | R¹ | Salt | Physical properties, etc. |
|---|---|---|---|---|
| 13-43 | 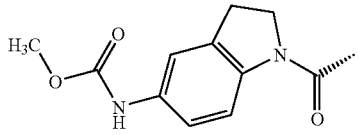 | H | Free form | |
| 13-44 | 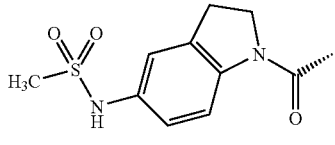 | H | Free form | |
| 13-45 | 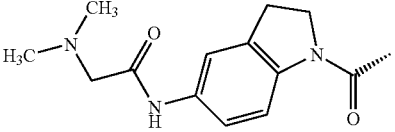 | H | HI | Brownish powder |
| 13-46 | 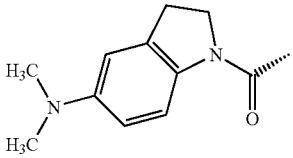 | H | Free form | |
| 13-47 | 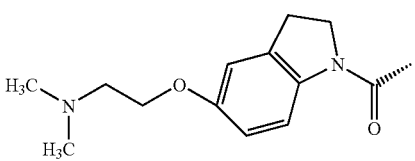 | H | Free form | Colorless crystal Melting point: 199–202° C. MS # APCI (m/z): 332 [M + H]+ |
| 13-48 | 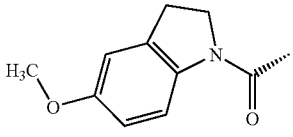 | H | Free form | Pale brownish powder MS # APCI (m/z): 275 [M + H]+ |
| 13-49 | 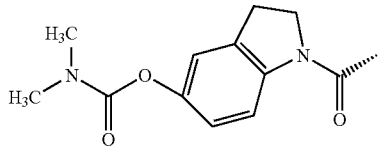 | H | Free form | Colorless powder MS # APCI (m/z): 332 [M + H]+ |
| 13-50 | 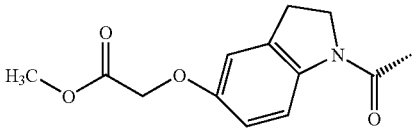 | H | Free form | Colorless powder MS # APCI (m/z): 332 [M + H]+ |
| 13-51 | 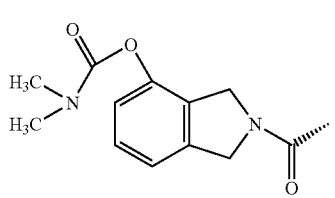 | H | Free form | Colorless powder MS # APCI (m/z): 332 [M + H]+ |

TABLE 8-continued

| Reference Example No. | R²—X— | R¹ | Salt | Physical properties, etc. |
|---|---|---|---|---|
| 13-52 | methyl (2-acetylisoindolin-4-yl)oxyacetate group | H | Free form | Colorless powder<br>MS # APCI (m/z): 333 [M + H]+ |
| 14-1 | 4-hydroxypiperidin-1-yl-carbonyl | H | HCl | Colorless resin<br>MS # APCI (m/z): 227 [M + H]+ |
| 14-2 | morpholin-4-yl-carbonyl | H | HCl | Colorless powder<br>MS # APCI (m/z): 213 [M + H]+ |
| 14-3 | isoindolin-2-yl-carbonyl | H | Free form | Pale reddish crystal<br>Melting point: 144–145° C. |
| 14-4 | 3-(hydroxymethyl)-1,2,3,4-tetrahydroisoquinolin-2-yl-carbonyl | H | Free form | Colorless oil<br>MS # APCI (m/z): 289 [M + H]+ |
| 14-5 | N,N-diethylcarbamoyl | H | HCl | Colorless powder<br>MS # APCI (m/z): 199 [M + H]+ |
| 14-6 | N,N-dimethylcarbamoyl | H | Free form | Pale yellowish oil<br>MS # APCI (m/z): 171 [M + H]+ |
| 14-7 | 4-(pyridin-2-yl)piperazin-1-yl-carbonyl | H | Free form | Colorless oil<br>MS # APCI (m/z): 289 [M + H]+ |
| 14-8 | 4-(piperidin-1-yl)piperidin-1-yl-carbonyl | H | 2HCl | Brownish powder<br>MS # APCI (m/z): 294 [M + H]+ |

TABLE 8-continued

| Reference Example No. | R²—X— | R¹ | Salt | Physical properties, etc. |
|---|---|---|---|---|
| 14-9 | | H | Free form | Colorless powder<br>MS # APCI (m/z): 303<br>[M + H]+ |
| 14-10 | | H | Free form | Colorless oil<br>MS # APCI (m/z): 302<br>[M + H]+ |
| 14-11 | | H | Free form | Colorless oil<br>MS # APCI (m/z) |
| 14-12 | | H | Free form | Colorless crystal<br>Melting point:<br>188–193° C. |
| 14-13 | | H | Free form | Pale yellowish crystal<br>Melting point:<br>194–196° C. |
| 14-14 | | H | Free form | Slightly yellowish resin<br>MS # APCI (m/z): 356<br>[M + H]+ |
| 14-15 | | H | Free form | Slightly yellowish resin<br>MS # APCI (m/z): 356<br>[M + H]+ |
| 14-16 | | H | Free form | Brownish oil<br>MS # APCI (m/z): 316<br>[M + H]+ |

The invention claimed is:

1. A method for treating a disease in a patient selected from among diabetes, hyperglycemia, hyperinsulinemia, diabetes complications, obesity, overeating, and disorders of lipid metabolism comprising administering to a patient in need thereof a pharmaceutical formulation comprising a compound represented by the formula:

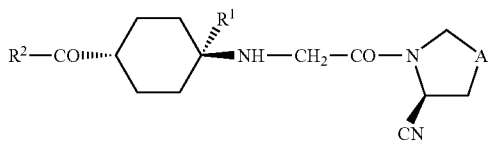

[I]

wherein A represents —CH$_2$— or —S—,

R$^1$ represents a hydrogen atom, a lower alkyl group, a hydroxy lower alkyl group or a lower alkoxy lower alkyl group, and R$^2$ represents:
(1) a cyclic group which may be substituted, where the cyclic group portion represents
    (i) a monocyclic, bicyclic or tricyclic hydrocarbon group, or
    (ii) a monocyclic, bicyclic or tricyclic heterocyclic group; or
(2) an amino group which may be substituted;
or a pharmaceutically acceptable salt thereof;
and one or more pharmaceutically acceptable excipients.

2. The method according to claim 1, wherein the disease is diabetes.

3. The method according to claim 1, wherein the disease is type-2 diabetes.

4. The method according to any one of claims 1, 2, or 3, wherein R$^2$ is
(1) a cyclic group which may have 1 to 3 substituents which are the same or different and are selected from the substituents of Group A listed below, where the cyclic group portion is (i) a monocyclic, bicyclic or tricyclic hydrocarbon group, or (ii) a monocyclic, bicyclic or tricyclic heterocyclic group, or
(2) an amino group which may have 1 or 2 substituents which are the same or different and selected from the substituents of Group B listed below;

Substituents of Group A:
a halogen atom; cyano group; nitro group; oxo group; hydroxy group; carboxy group;
oxidyl group; amino group; carbamoyl group; aminosulfonyl group; lower alkyl group;
lower alkoxy group; lower alkanoyl group; lower alkoxycarbonyl group; lower alkoxy-substituted lower alkanoyl group;
lower alkoxycarbonyl-substituted lower alkoxy group;
lower alkoxycarbonyl-substituted lower alkoxycarbonyl group;
lower alkylthio group;
lower alkylsulfonyl group;
di-lower alkylamino-substituted lower alkoxy group;
di-lower alkylaminocarbonyloxy group;
lower alkyl group substituted by one or more groups selected from an amino group, carbamoyl group, halogen atom, hydroxy group, carboxy group, lower alkoxy group and mono- or di-substituted amino group;
mono- or di-substituted amino group;
mono- or di-substituted carbamoyl group;
substituted or unsubstituted lower cycloalkyl group;
substituted or unsubstituted lower cycloalkyl-CO—;
substituted or unsubstituted lower cycloalkyl-lower alkyl group;
substituted or unsubstituted phenyl group;
substituted or unsubstituted phenyl-O—;
substituted or unsubstituted phenyl-CO—;
substituted or unsubstituted phenyl-lower alkyl group;,
substituted or unsubstituted phenyl-O-lower alkyl group;
substituted or unsubstituted phenylsulfonyl group;
substituted or unsubstituted phenyl-lower alkoxy group;
substituted or unsubstituted phenyl-lower alkoxycarbonyl group;
substituted or unsubstituted lower cycloalkenyl group;
substituted or unsubstituted bicyclic heterocyclic group;
substituted or unsubstituted monocyclic 5- or 6-membered heterocyclic group;
substituted or unsubstituted monocyclic 5- or 6-membered heterocyclic group-O—;
substituted or unsubstituted monocyclic 5- or 6-membered heterocyclic group-CO—;
substituted or unsubstituted monocyclic 5- or 6-membered heterocyclic group-CO-lower alkyl group; and
substituted or unsubstituted monocyclic 5- or 6-membered heterocyclic group-lower alkyl group;

Substituents of Group B:
lower alkyl group; lower alkoxy-substituted lower alkyl group; lower alkoxycarbonyl-substituted lower alkyl group; a hydroxy lower alkyl group; a carboxy lower alkyl group;
substituted or unsubstituted lower cycloalkyl group;
substituted or unsubstituted lower cycloalkyl-lower alkyl group;
substituted or unsubstituted phenyl group;
substituted or unsubstituted phenyl-lower alkyl group;
substituted or unsubstituted bicyclic hydrocarbon group;
substituted or unsubstituted monocyclic 5- or 6-membered heterocyclic group;
substituted or unsubstituted monocyclic 5- or 6-membered heterocyclic group-lower alkyl group; and
substituted or unsubstituted bicyclic heterocyclic group-lower alkyl group.

5. The method according to any one of claims 1, 2, or 3, wherein when the substituent selected from the substituents of Group A is a mono- or di-substituted amino lower alkyl group, a mono- or di-substituted amino group, or a mono- or di-substituted carbamoyl group, then the substituent has one or more substituents selected from the substituents of Group C mentioned below; and when the substituent selected from the substituents of Group A is a substituted lower cycloalkyl group, a substituted lower cycloalkyl-CO—, a substituted lower cycloalkyl-lower alkyl group, a substituted phenyl group, a substituted phenyl-O—, a substituted phenyl-CO—, a substituted phenyl-lower alkyl group, a substituted phenyl-O-lower alkyl group, a substituted phenylsulfonyl group, a substituted phenyl-lower alkoxy group, a substituted phenyl-lower alkoxycarbonyl group, a substituted lower cycloalkenyl group, a substituted bicyclic heterocyclic group, a substituted monocyclic 5- or 6-membered heterocyclic group, a substituted monocyclic 5- or 6-membered heterocyclic group-O—, a substituted monocyclic 5- or 6-membered heterocyclic group-CO—, a substituted monocyclic 5- or 6-membered heterocyclic group-CO-lower alkyl group or a substituted monocyclic 5- or 6-membered heterocyclic group-lower alkyl group, then the substituent has one or more substituents selected from a halogen atom, cyano group, nitro group, oxo group and the substituents of Group C mentioned below; and when the substituent selected from the substituents of Group B is a substituted lower cycloalkyl group, a substituted lower cycloalkyl-lower alkyl group, a substituted phenyl group, a substituted phenyl-lower alkyl group, a substituted bicyclic hydrocarbon group, a substituted monocyclic 5- or 6-membered heterocyclic group, a substituted monocyclic 5- or 6-membered heterocyclic group-lower alkyl group or a substituted bicyclic heterocyclic group-lower alkyl group, then the substituent has substituent(s) selected from the substituents of Group C mentioned below;

Substituents of Group C:

a lower alkyl group; a hydroxy-lower alkyl group; a lower alkanoyl group; a lower cycloalkylcarbonyl group; a lower alkoxy group; a lower alkoxycarbonyl group; a lower alkylsulfonyl group; a di-lower alkyl-substituted carbamoyl group; a di-lower alkylamino-substituted lower alkanoyl group;

a substituted or unsubstituted phenyl group;
a substituted or unsubstituted phenyl-O—;
a substituted or unsubstituted phenyl-CO—;
a substituted or unsubstituted phenyl-lower alkanoyl group;
a substituted or unsubstituted phenyl-lower alkyl group;
a substituted or unsubstituted phenyl-lower alkoxy group;
a substituted or unsubstituted monocyclic 5- or 6-membered heterocyclic group;
a substituted or unsubstituted monocyclic 5- or 6-membered heterocyclic group-O—;
a substituted or unsubstituted monocyclic 5- or 6-membered heterocyclic group-CO—; and
a substituted or unsubstituted monocyclic 5- or 6-membered heterocyclic group-substituted amino group;

(in the substituents of Group C, a substituent in the substituted phenyl group portion or the substituted monocyclic 5- or 6-membered heterocyclic group portion is selected from a halogen atom, cyano group, nitro group, oxo group, a lower alkyl group, a lower alkoxy group, a lower alkanoyl group and a lower alkoxycarbonyl group).

6. The method according to any one of claims 1, 2, or 3, wherein $R^2$ is
   (1) a cyclic group which may be substituted, where the cyclic group portion is a group selected from the following (i) to (iv)
      (i) a monocyclic hydrocarbon group having 3 to 7 carbon atoms,
      (ii) a bicyclic hydrocarbon group having 9 to 11 carbon atoms,
      (iii) a monocyclic heterocyclic group containing 1 or 2 hetero atoms selected from nitrogen atom, oxygen atom and sulfur atom, and
      (iv) a bicyclic heterocyclic group containing 1 to 3 hetero atoms selected from nitrogen atom, oxygen atom and sulfur atom and comprising two 5- to 7-membered rings being fused; or
   (2) a substituted amino group.

7. The method according to any one of claims 1, 2, or 3, wherein $R^2$ is
   (1) a cyclic group which may be substituted, where the cyclic group portion is a group selected from
      phenyl group, cyclohexyl group, cyclopentyl group, cyclobutyl group, cyclopropyl group, an indanyl group, an indenyl group, a naphthyl group, tetrahydronaphthyl, a pyrrolidinyl group, an imidazolidinyl group, a pyrazolidinyl group, an oxolanyl group, a thiolanyl group, a pyrrolinyl group, an imidazolinyl group, a pyrazolinyl group, a pyrrolyl group, an imidazolyl group, a pyrazolyl group, a triazolyl group, a tetrazolyl group, a furyl group, an oxazolyl group, an isoxazolyl group, an oxadiazolyl group, a thienyl group, a thiazolyl group, an isothiazolyl group, a thiadiazolyl group, a piperidyl group, a piperazinyl group, a morpholinyl group, a thiomorpholinyl group, a pyridyl group, a pyrimidinyl group, a pyrazinyl group, a pyridazinyl group, a pyranyl group, a tetrahydropyridyl group, a dihydropyridazinyl group, a perhydroazepinyl group, a perhydrothiazepinyl group, an indolinyl group, an isoindolinyl group, an indolyl group, an indazolyl group, an isoindolyl group, a benzimidazolyl group, a benzothiazolyl group, a benzoxazolyl group, a benzodioxolanyl group, a benzothienyl group, a benzofuryl group, a thienopyridyl group, a thiazolopyridyl group, a pyrrolopyridyl group, a dihydropyrrolopyridyl group, a quinolyl group, an isoquinolyl group, a quinoxalinyl group, a quinazolinyl group, a phthalazinyl group, a cinnolinyl group, a chromanyl group, an isochromanyl group, a naphthyridinyl group and partially or completely saturated cyclic groups thereof; or
   (2) a substituted amino group.

8. The method according to any one of claims 1, 2, or 3, wherein $R^2$ is
   (1) a cyclic group which may be substituted, where the cyclic group portion is a group selected from the group consisting of phenyl group, cyclohexyl group, a pyrrolidinyl group, a tetrazolyl group, a furyl group, a thienyl group, a thiazolyl group, a piperidyl group, a piperazinyl group, a morpholinyl group, a thiomorpholinyl group, a pyridyl group, a pyrimidinyl group, a pyrazinyl group, a pyridazinyl group, a perhydroazepinyl group, an indolinyl group, an isoindolinyl group, a benzothienyl group, a thienopyridyl group, a pyrrolopyridyl group, a dihydropyrrolopyridyl group, a quinolyl group, an isoquinolyl group, a quinoxalinyl group and partially or completely saturated cyclic groups thereof; or
   (2) a substituted amino group.

9. The method according to any one of claims 1, 2, or 3, wherein $R^2$ is
   (1) a cyclic group which may be substituted, where the cyclic group portion is a group selected from the group consisting of
      a pyrrolidinyl group, a piperidyl group, a piperazinyl group, a morpholinyl group, a thiomorpholinyl group, a pyridyl group, a pyrimidinyl group, an indolinyl group, an isoindolinyl group, a pyrrolopyridyl group, a dihydropyrrolopyridyl group and partially or completely saturated cyclic groups thereof; or
   (2) a substituted amino group.

10. The method according to any one of claims 1, 2, or 3, wherein $R^2$ is
   (1) a cyclic group which may have 1 to 3 substituents which are the same or different and selected from the substituents of Group A' mentioned below, where the cyclic group portion is selected from the group consisting of
      a pyrrolidinyl group, a piperidyl group, a piperazinyl group, a morpholinyl group, a thiomorpholinyl group, a pyridyl group, a pyrimidinyl group, an indolinyl group, an isoindolinyl group, a pyrrolopyridyl group, a dihydropyrrolopyridyl group and partially or completely saturated cyclic groups thereof; or (2) an amino group substituted by 1 or 2 substituents which are the same or different and selected from the substituents of Group B' mentioned below;

Substituents of Group A':

a halogen atom, cyano group, nitro group, oxo group, carbamoyl group, a lower alkyl group, a lower alkoxy group, a lower alkanoyl group, a lower alkoxycarbonyl group, a lower alkoxy-substituted lower alkyl group, a mono- or di-substituted amino group, a mono- or di-substituted carbamoyl group, a lower cycloalkyl-CO—, a substituted or unsubstituted phenyl group, a substituted or unsubstituted phenyl-lower alkyl group, a substituted or unsubstituted monocyclic 5- or 6-membered heterocyclic group, a substituted or unsubstituted monocyclic 5- or 6-membered heterocyclic group-O—, and a substituted or unsubstituted monocyclic 5- or 6-membered heterocyclic group-CO—;

Substituents of Group B':

a lower alkyl group, a lower cycloalkyl group, a lower alkoxy-substituted lower alkyl group, a pyrimidinyl group, a thiazolyl group and a thiadiazolyl group.

11. The method according to any one of claims 1, 2, or 3, wherein A is —CH$_2$—, and R$^1$ is hydrogen atom.

12. The method according to any one of claims 1, 2, or 3, wherein A is —CH$_2$—, R$^1$ is hydrogen atom, and R$^2$ is a cyclic group which may be substituted.

13. The method according to any one of claims 1, 2, or 3, wherein A is —CH$_2$—, R$^1$ is hydrogen atom, and R$^2$ is a substituted amino group.

14. The method according to any one of claims 1, 2, or 3, wherein the aliphatic nitrogen-containing 5-membered ring compound is selected from the group consisting of:

(S)-2-cyano-1-[trans-4-(dimethylaminocarbonyl)cyclohexylamino]acetylpyrrolidine;

(S)-2-cyano-1-[trans-4-(morpholinocarbonyl)cyclohexylamino]acetylpyrrolidine;

(S)-2-cyano-1-[trans-4-(N-ethyl-N-methoxyethylaminocarbonyl)cyclohexylamino]acetyl pyrrolidine;

(S)-2-cyano-1-[trans-4-(N-ethyl-N-isopropylaminocarbonyl)-cyclohexylamino]acetyl pyrrolidine;

(S)-2-cyano-1-[trans-4-(N-methyl-N-butylaminocarbonyl)-cyclohexylamino]acetyl pyrrolidine;

(S)-2-cyano-1-[trans-4-[(S)-2-methoxymethylpyrrolidin-1-ylcarbonyl]cyclohexylamino]acetylpyrrolidine;

(S)-2-cyano-1-[trans-4-(3-carbamoylpiperidinocarbonyl)cyclohexylamino]acetylpyrrolidine;

(S)-2-cyano-1-[trans-4-(4-acetylpiperazin-1-yl-carbonyl)cyclohexylamino]acetylpyrrolidine;

(S)-2-cyano-1-[trans-4-(2-isoindolinylcarbonyl)cyclohexylamino]acetylpyrrolidine;

(S)-2-cyano-1-[trans-4-[4-(3-pyridylcarbonyl)piperazin-1-ylcarbonyl]cyclohexylamino]acetylpyrrolidine;

(S)-2-cyano-1-{trans-4-[4-(3-thenoyl)piperazin-1-yl-carbonyl]cyclohexylamino}acetylpyrrolidine;

(S)-2-cyano-1-{trans-4-[4-(4-chlorophenyl)piperazin-1-ylcarbonyl]cyclohexylamino}acetylpyrrolidine;

(S)-2-cyano-1-[trans-4-(cis-2,6-dimethylmorpholinocarbonyl)cyclohexylamino]acetylpyrrolidine;

(S)-2-cyano-1-[trans-4-(5-nitro-2-isoindolinylcarbonyl)cyclohexylamino]acetylpyrrolidine;

(S)-2-cyano-1-[trans-4-(piperidinocarbonyl)cyclohexylamino]acetylpyrrolidine;

(S)-2-cyano-1-[trans-4-(4-carbamoylpiperidinocarbonyl)cyclohexylamino]acetylpyrrolidine;

(S)-2-cyano-1-[trans-4-(1-pyrrolidinylcarbonyl)cyclohexylamino]acetylpyrrolidine;

(S)-2-cyano-1-[trans-4-(4-cyclopropylcarbonylpiperazin-1-ylcarbonyl)cyclohexylamino]acetylpyrrolidine;

(S)-2-cyano-1-[trans-4-(4-propionylpiperazin-1-yl-carbonyl)cyclohexylamino]acetylpyrrolidine;

(S)-2-cyano-1-[trans-4-(1-indolinylcarbonyl)cyclohexylamino]acetylpyrrolidine;

(S)-2-cyano-1-[trans-4-(2,3-dihydro-1H-pyrrolo[3,4-b]pyridin-2-ylcarbonyl)cyclohexylamino]acetylpyrrolidine;

(S)-2-cyano-1-[trans-4-[4-(2-pyrimidinyloxy)-piperidinocarbonyl]cyclohexylamino]acetylpyrrolidine;

(S)-2-cyano-1-{trans-4-[4-(5-bromo-2-pyrimidinyloxy)-piperidinocarbonyl]cyclohexylamino}acetylpyrrolidine;

(S)-2-cyano-1-[trans-4-(cis-3,5-dimethyl-4-benzylpiperazin-1-ylcarbonyl)cyclohexylamino]acetylpyrrolidine;

(S)-2-cyano-1-[trans-4-(4-cyclohexylcarbonylaminopiperidinocarbonyl)cyclohexylamino]acetylpyrrolidine;

(S)-2-cyano-1-{trans-4-[4-(N-phenylcarbamoyl)piperazin-1-ylcarbonyl]cyclohexylamino}acetylpyrrolidine;

(S)-2-cyano-1-[trans-4-(4-ethoxycarbonylpiperazin-1-ylcarbonyl)cyclohexylamino]acetylpyrrolidine;

(S)-2-cyano-1-[trans-4-[4-(2-thienyl)piperidinocarbonyl]cyclohexylamino]acetylpyrrolidine;

(S)-2-cyano-1-[trans-4-(1,1-dioxoperhydro-1,4-thiazin-4-ylcarbonyl)cyclohexylamino]acetylpyrrolidine;

(R)-4-cyano-3-[trans-4-(dimethylaminocarbonyl)cyclohexylamino]acetylthiazolidine;

(R)-4-cyano-3-[trans-4-(2-isoindolinylcarbonyl)cyclohexylamino]acetylthiazolidine;

(R)-4-cyano-3-[trans-4-(morpholinocarbonyl)cyclohexylamino]acetylthiazolidine; and (R)-4-cyano-3-[trans-4-(pyrrolidinylcarbonyl)cyclohexylamino]acetylthiazolidine; or a pharmaceutically acceptable salt thereof.

* * * * *